United States Patent [19]

Wood et al.

[11] Patent Number: 5,439,934
[45] Date of Patent: Aug. 8, 1995

[54] METHOD AND COMPOSITIONS FOR HELMINTIC, ARTHROPOD ECTOPARASITIC AND ACARIDAL INFECTIONS WITH NOVEL AGENTS

[75] Inventors: Irwin B. Wood, Yardley, Pa.; John A. Pankavich, Trenton, N.J.

[73] Assignee: American Cyanamid Company, Wayne, N.J.

[21] Appl. No.: 123,778

[22] Filed: Sep. 20, 1993

Related U.S. Application Data

[60] Division of Ser. No. 712,777, Jun. 10, 1991, Pat. No. 5,317,030, which is a continuation of Ser. No. 732,251, May 10, 1985, Pat. No. 5,198,464, which is a continuation-in-part of Ser. No. 617,649, Jun. 5, 1984, Pat. No. 4,869,901.

[51] Int. Cl.$^6$ .................. A61K 35/00; A01N 43/02
[52] U.S. Cl. .................... 514/450; 424/116
[58] Field of Search .................. 514/450; 424/116

[56] References Cited

U.S. PATENT DOCUMENTS

| | | | |
|---|---|---|---|
| 3,950,360 | 4/1976 | Aoki et al. | 260/343.2 R |
| 4,200,581 | 4/1980 | Fisher et al. | 514/30 |
| 4,285,963 | 8/1981 | Arison et al. | 514/455 |
| 4,480,059 | 10/1983 | Smith, III et al. | 523/466 |

FOREIGN PATENT DOCUMENTS

| | | |
|---|---|---|
| 0058518 | 8/1982 | European Pat. Off. |
| 0073660 | 3/1983 | European Pat. Off. |
| 0102721 | 3/1984 | European Pat. Off. |

OTHER PUBLICATIONS

Mishima et al., J. Antibiotics, 36:980 (Aug. 1983).
Carter, Chem. Abstracts, vol. 85, No. 118436e (1976).
Carter, Chem. Abstracts, vol. 106, No. 32663e (1987).

*Primary Examiner*—Allen J. Robinson
*Attorney, Agent, or Firm*—Anne M. Rosenblum

[57] ABSTRACT

The present invention relates to methods and compositions for the control and prevention of helmintic, arthropod ectoparasitic and acaridal infections, in warm-blooded animals, such as meat-producing animals, and poultry, by administering to said animals a therapeutically or prophylactically-effective amount of new agents designated LL-F28249$\alpha$, $\beta$, $\gamma$, $\delta$, $\epsilon$, $\xi$, $\eta$, $\theta$, $\iota$, $\kappa$, $\lambda$, $\mu$, $\nu$ and $\omega$, or mixtures thereof. The invention also relates to methods for the control of plant nematode infestations and other insecticidal activities. These novel agents are produced via a controlled conditioned microbiological fermentation using *Streptomyces cyaneogriseus* ssp. *noncyanogenus*, designated LL-F28249 and having deposit accession number NRRL 15773.

49 Claims, 57 Drawing Sheets

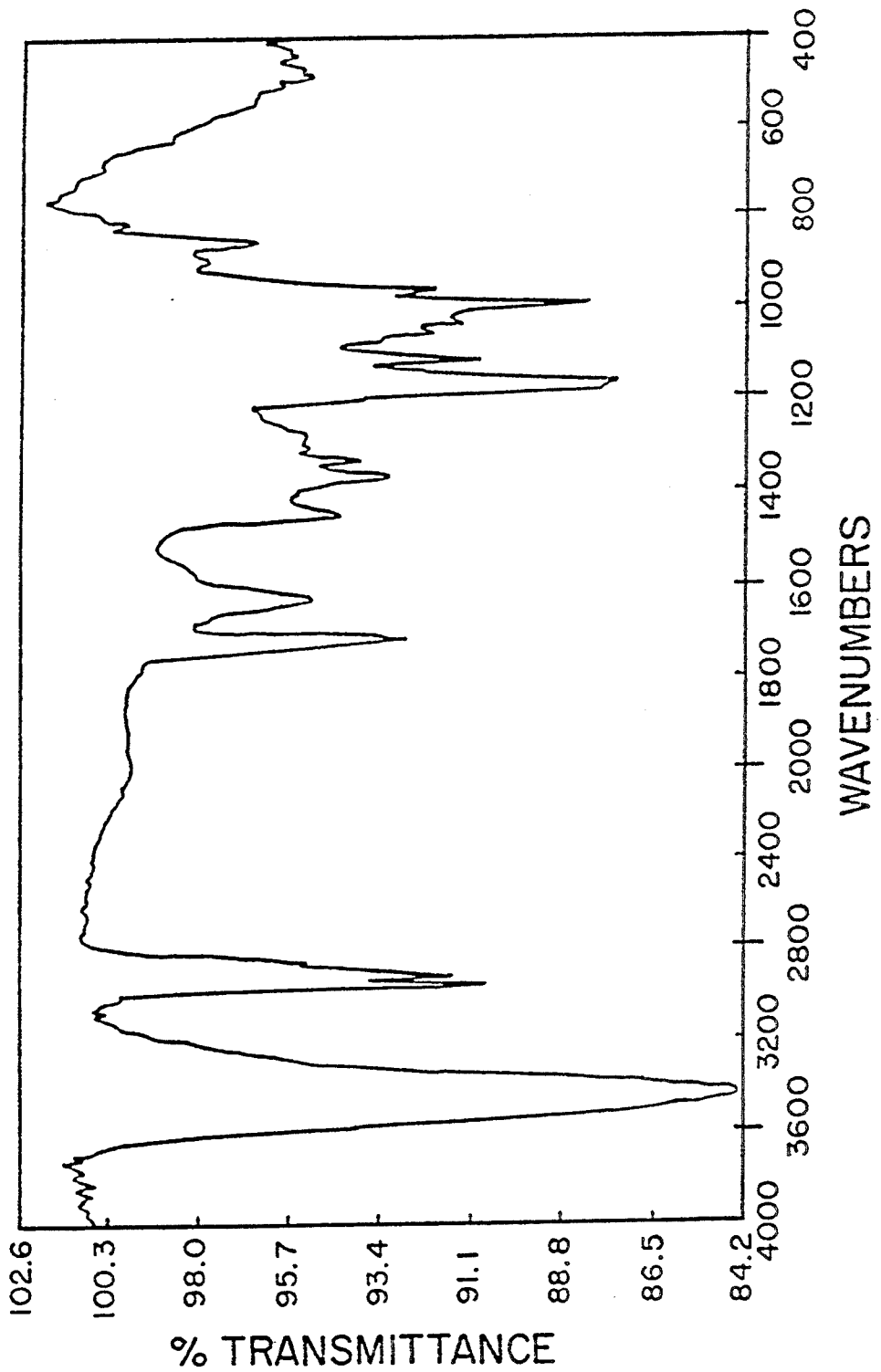
FIG. II

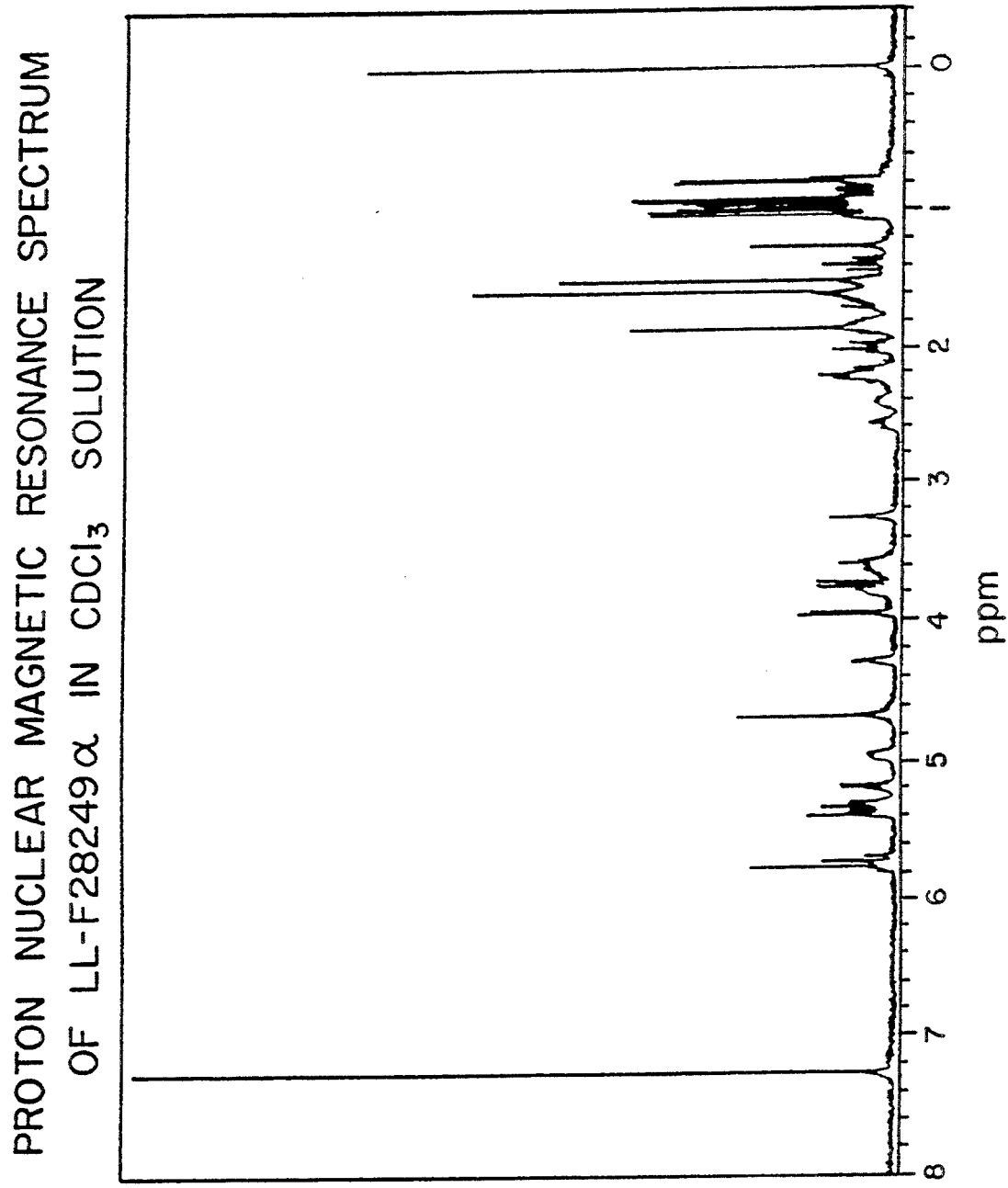
FIG. III

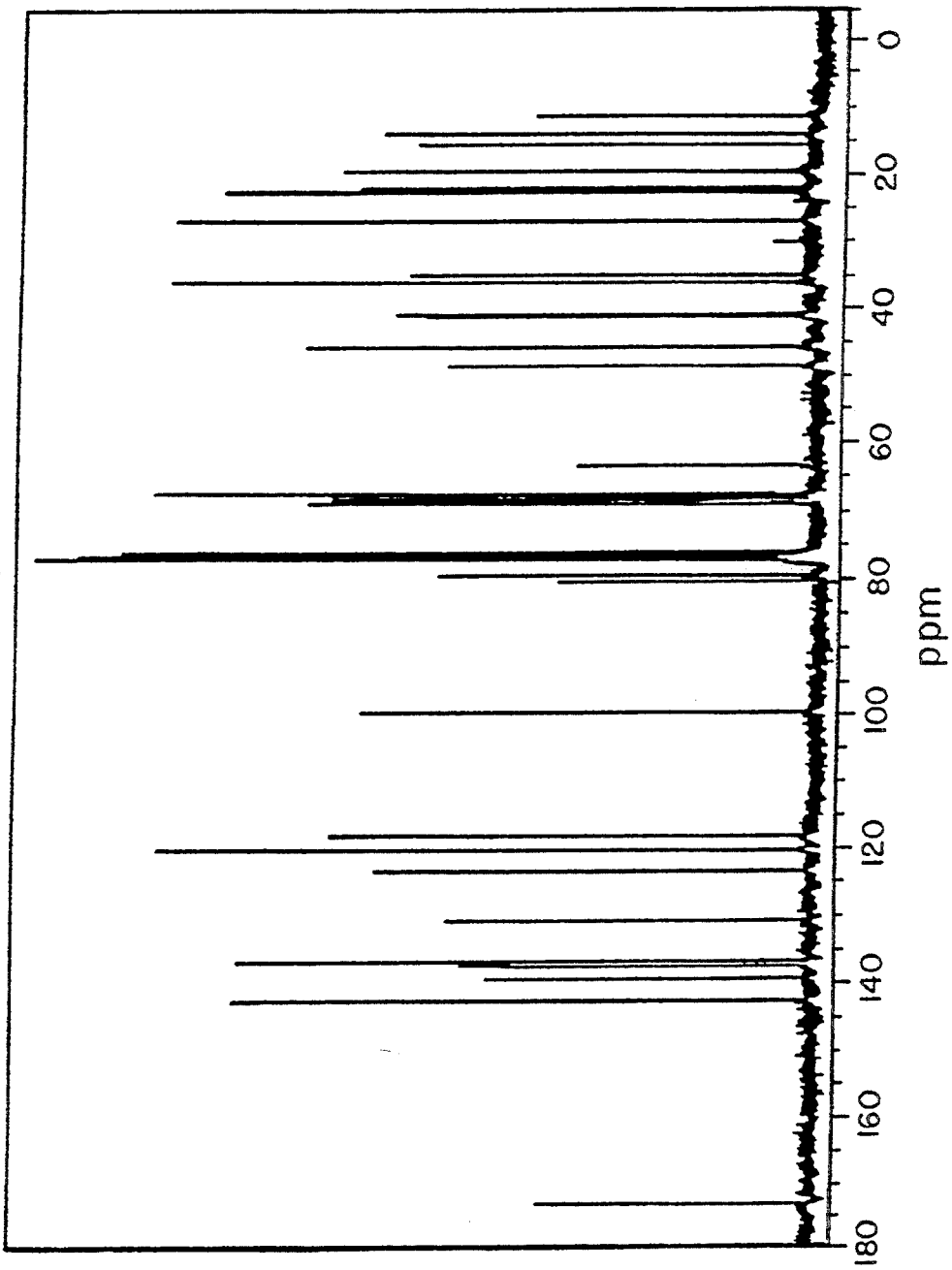
FIG. IV

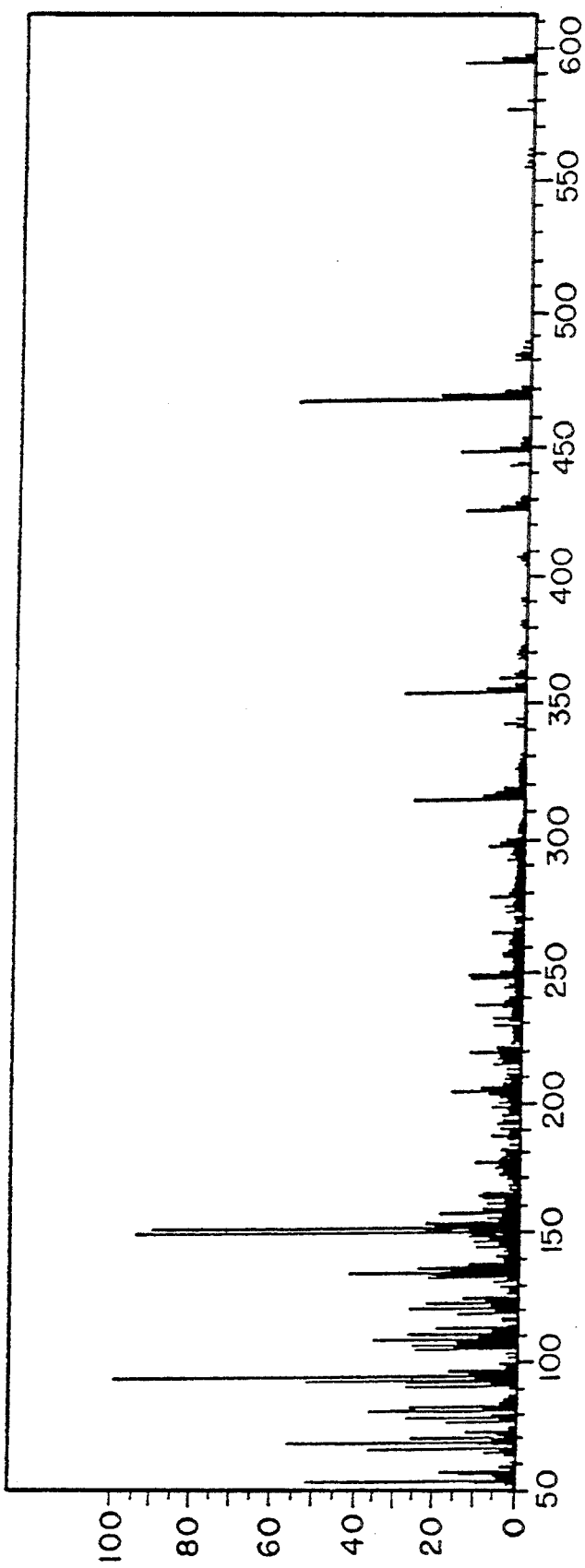
FIG. V

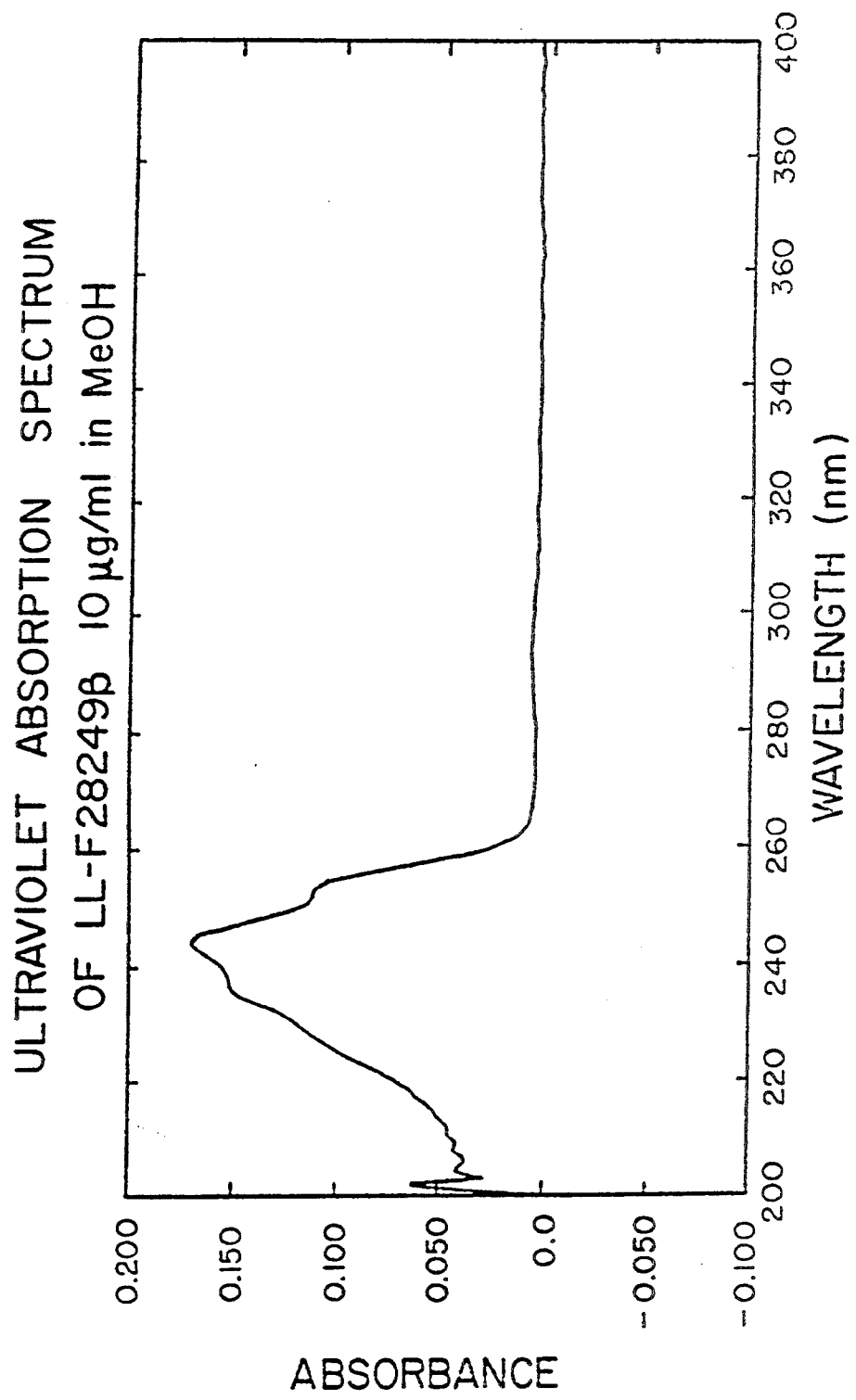

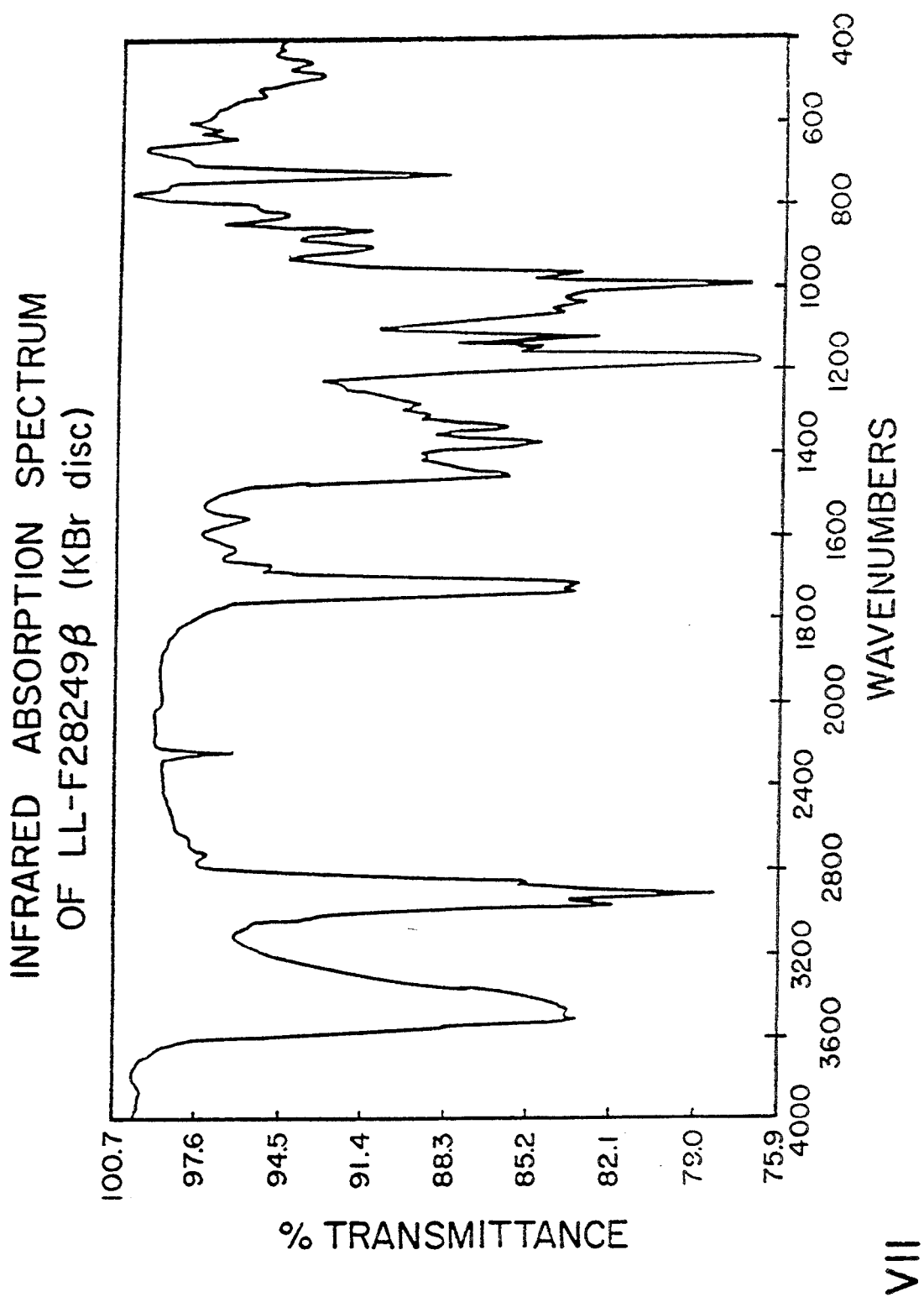
FIG. VII

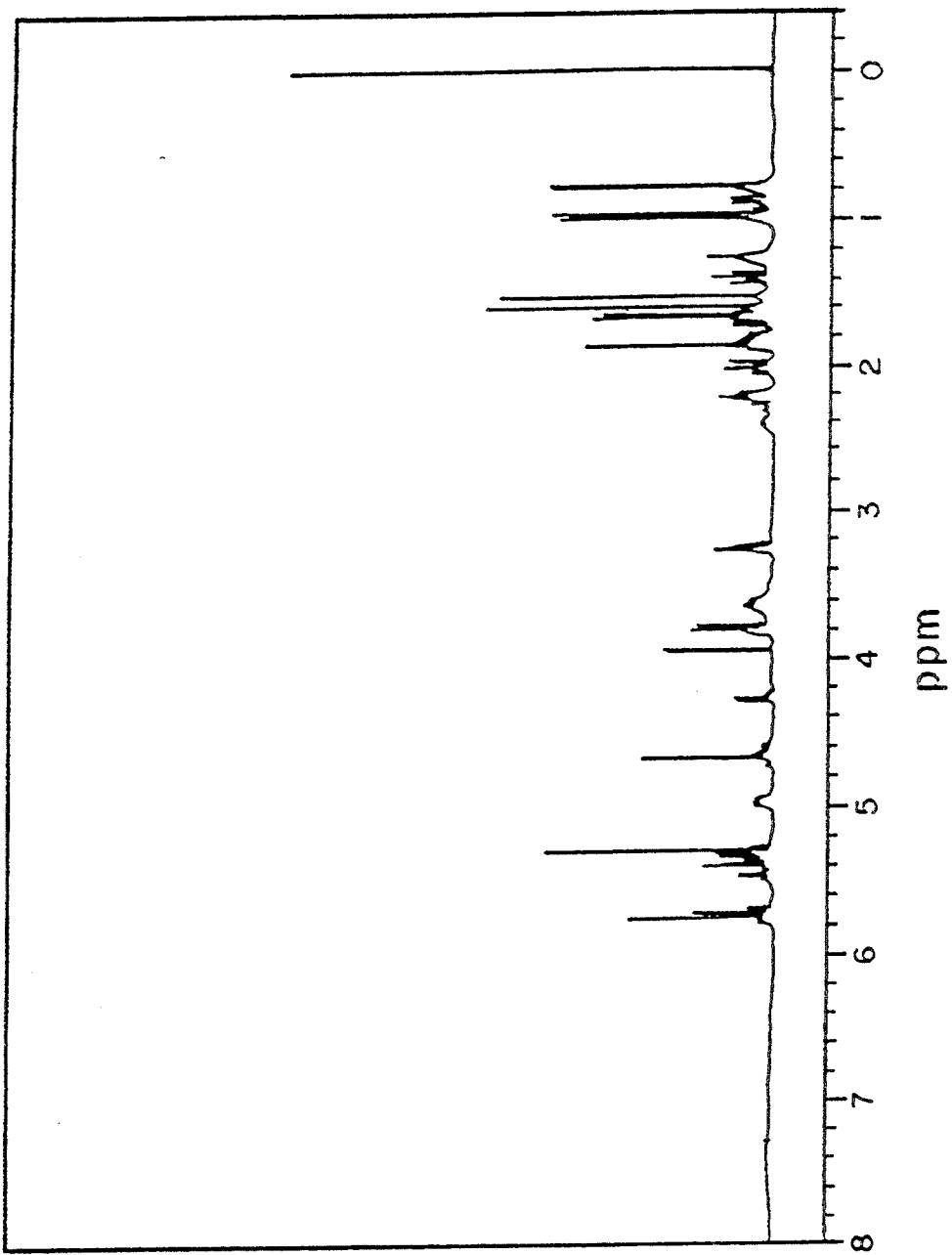
FIG. VIII

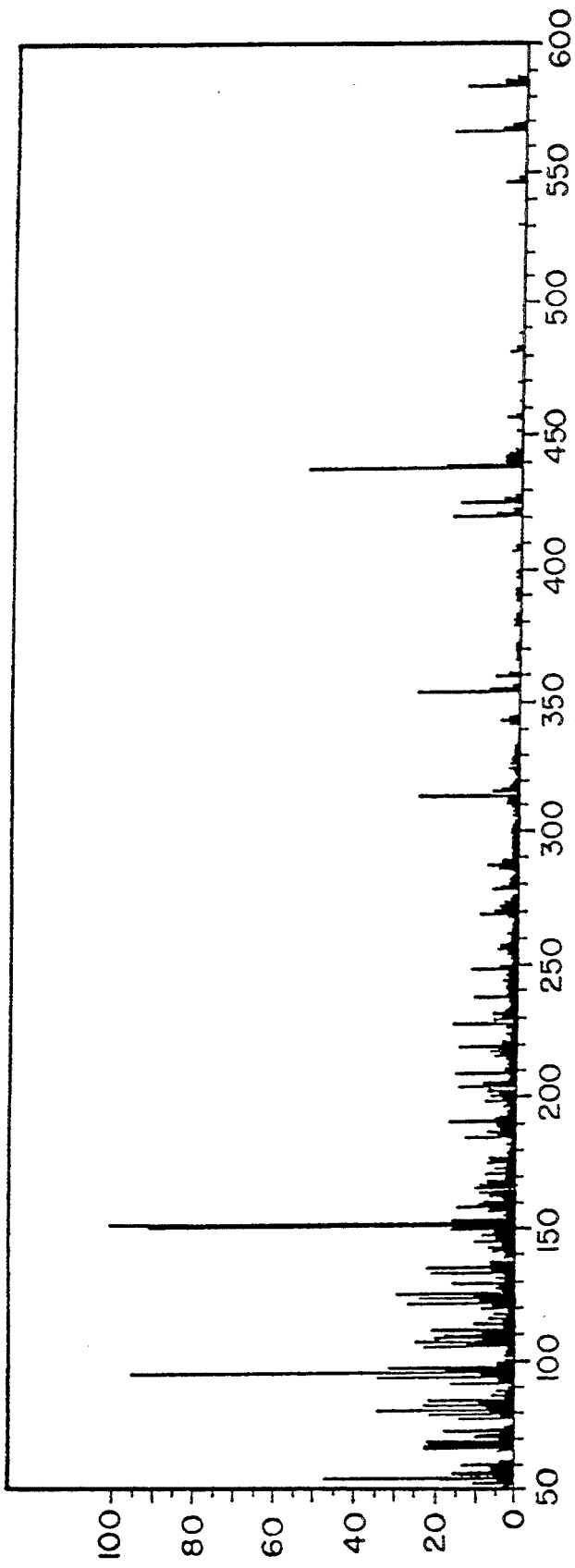
FIG. IX

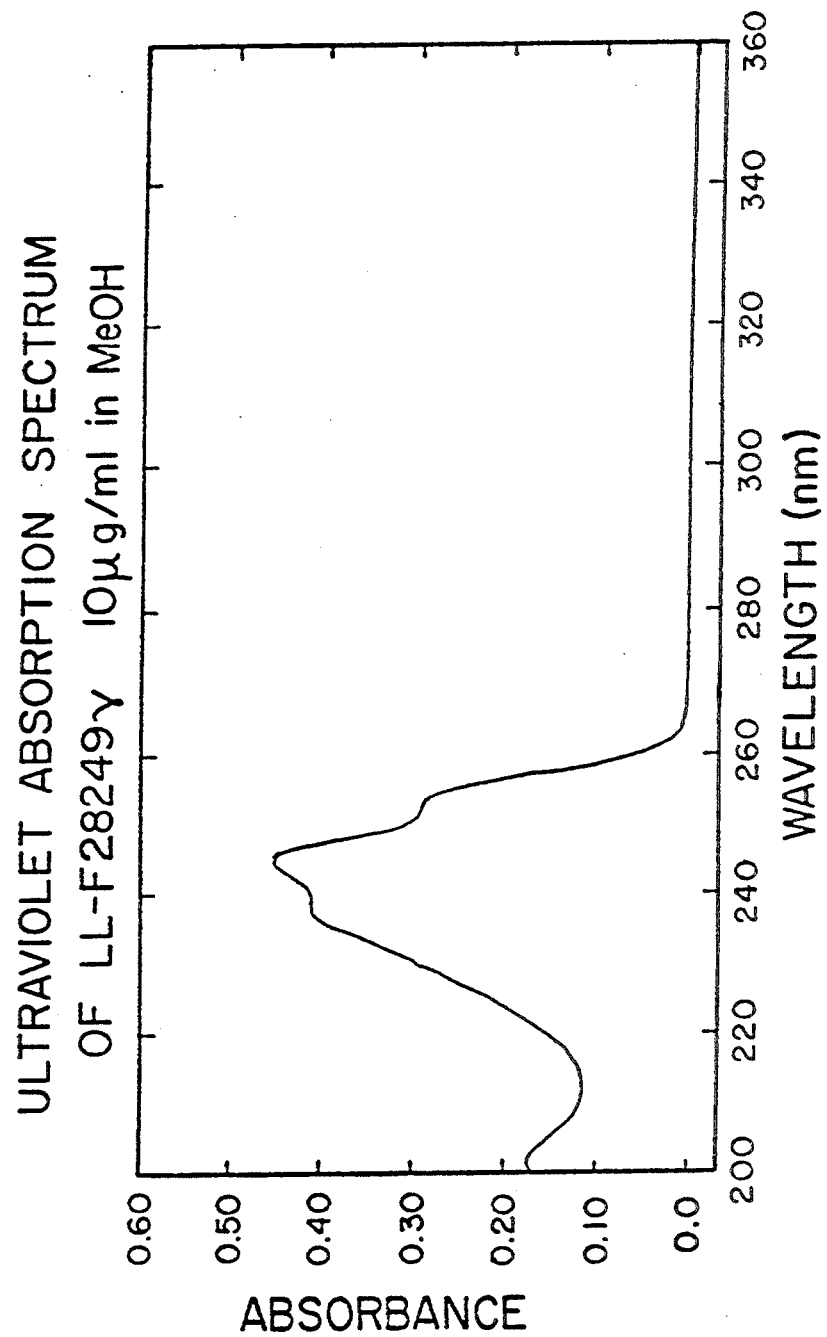
FIG. X

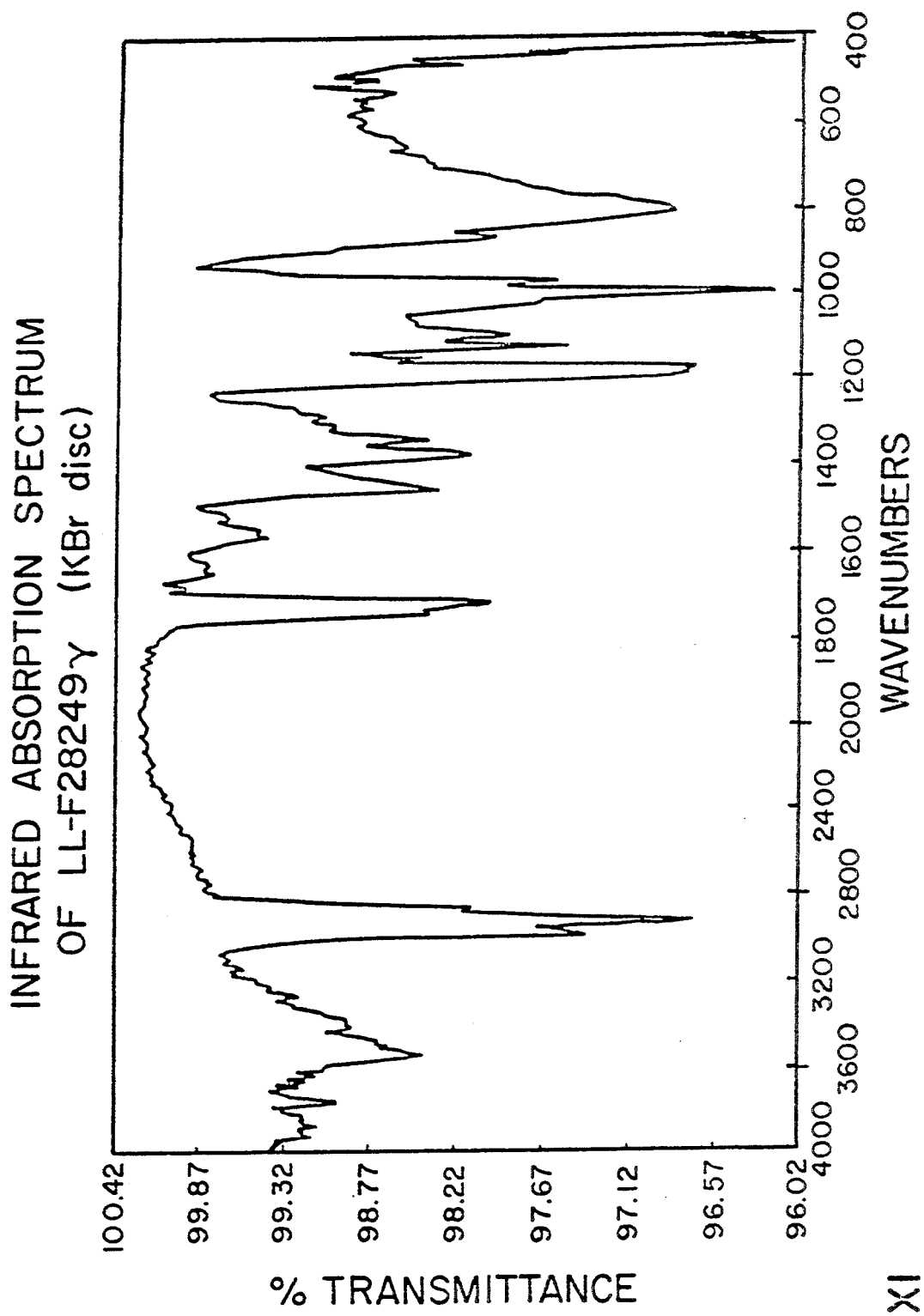

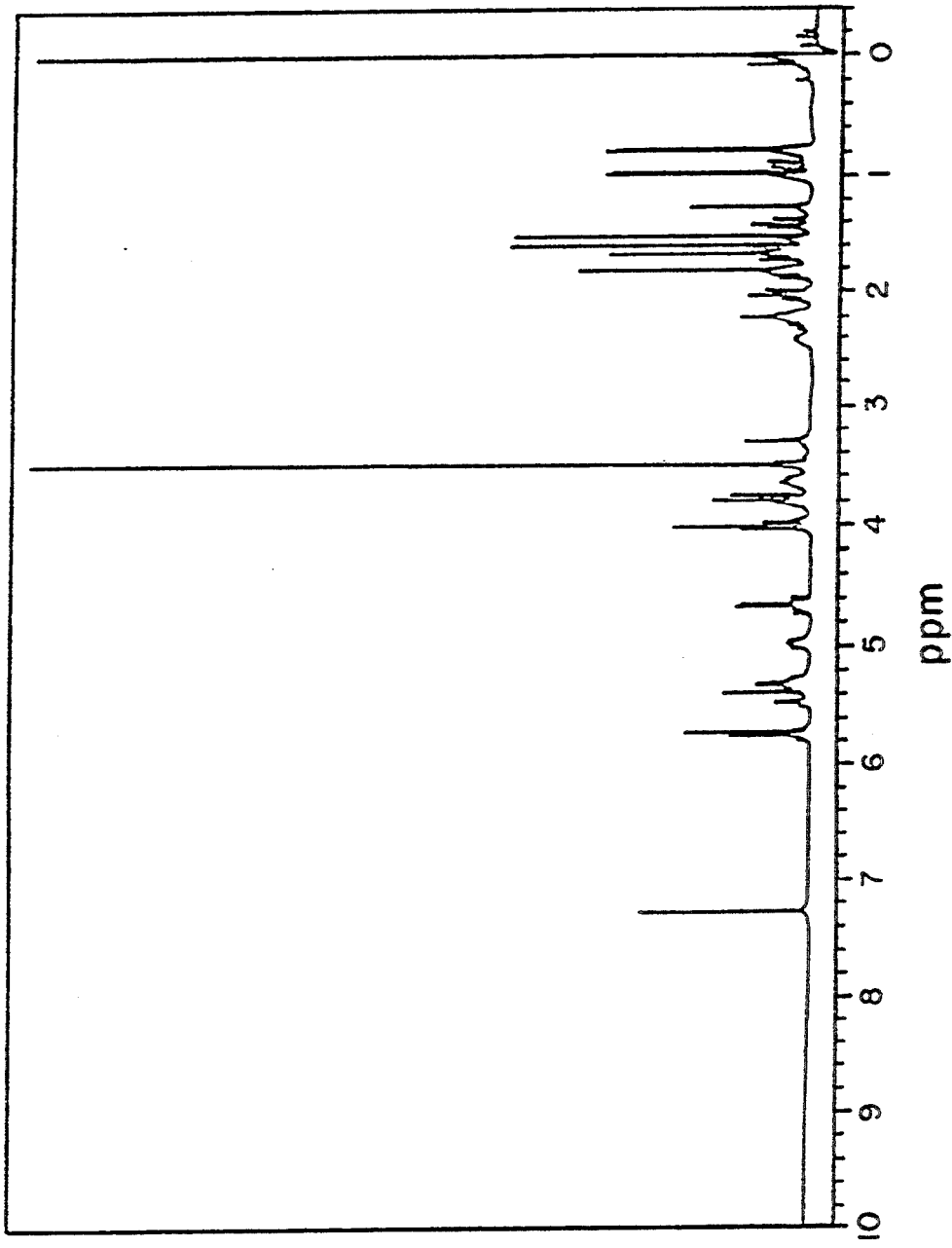

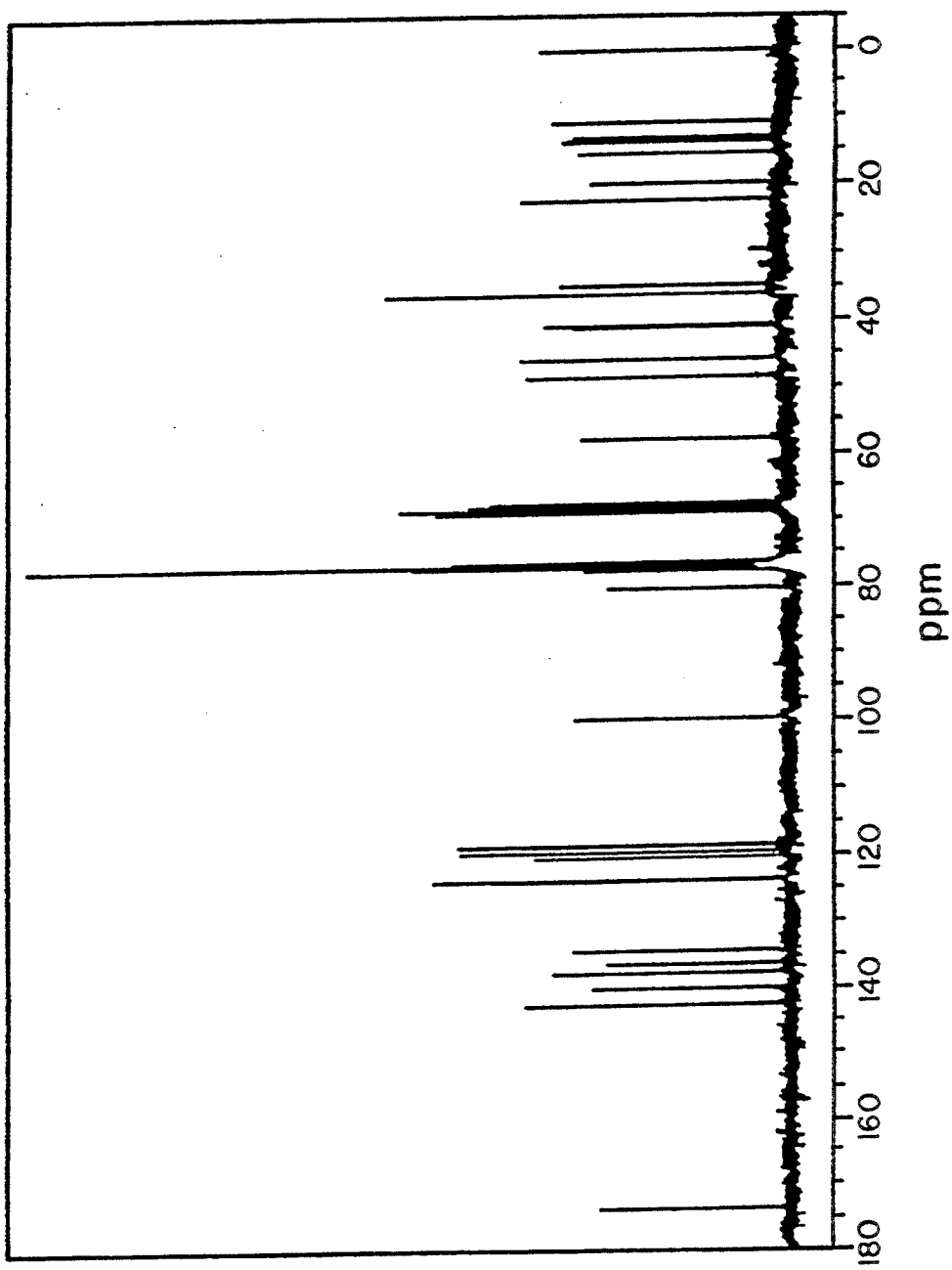
FIG. XIII

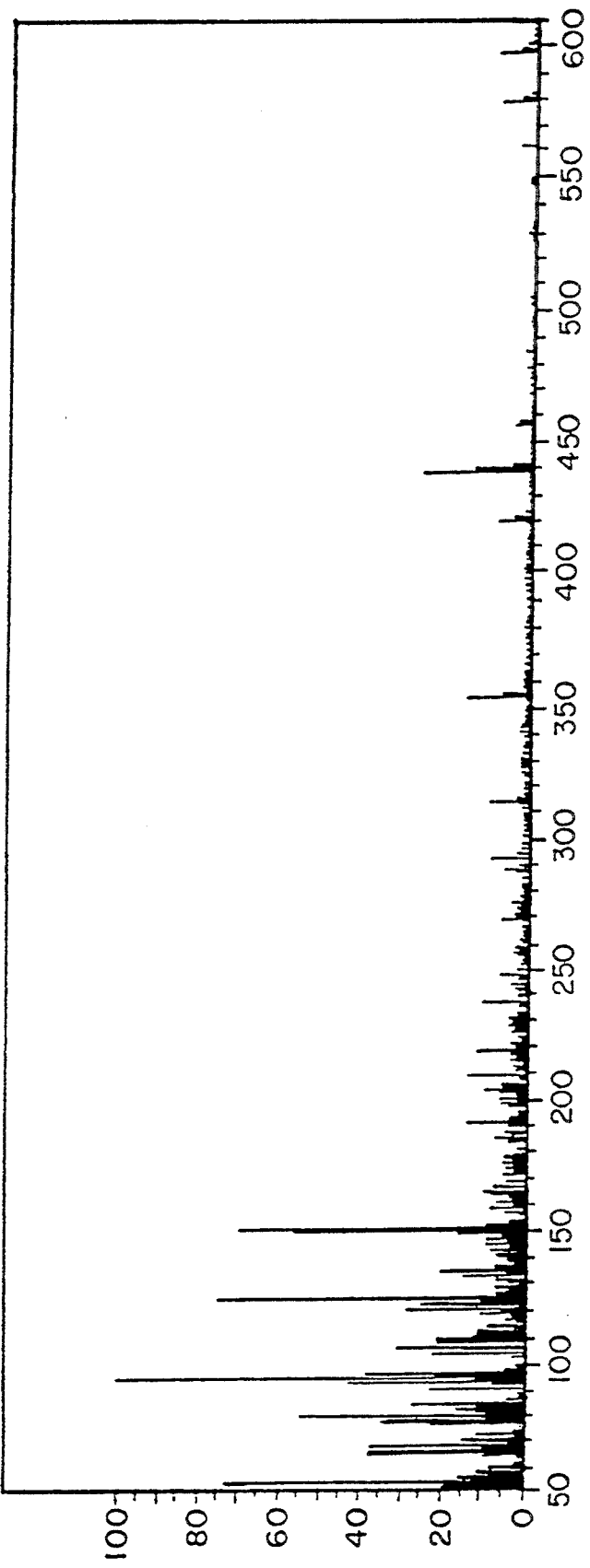
FIG. XIV

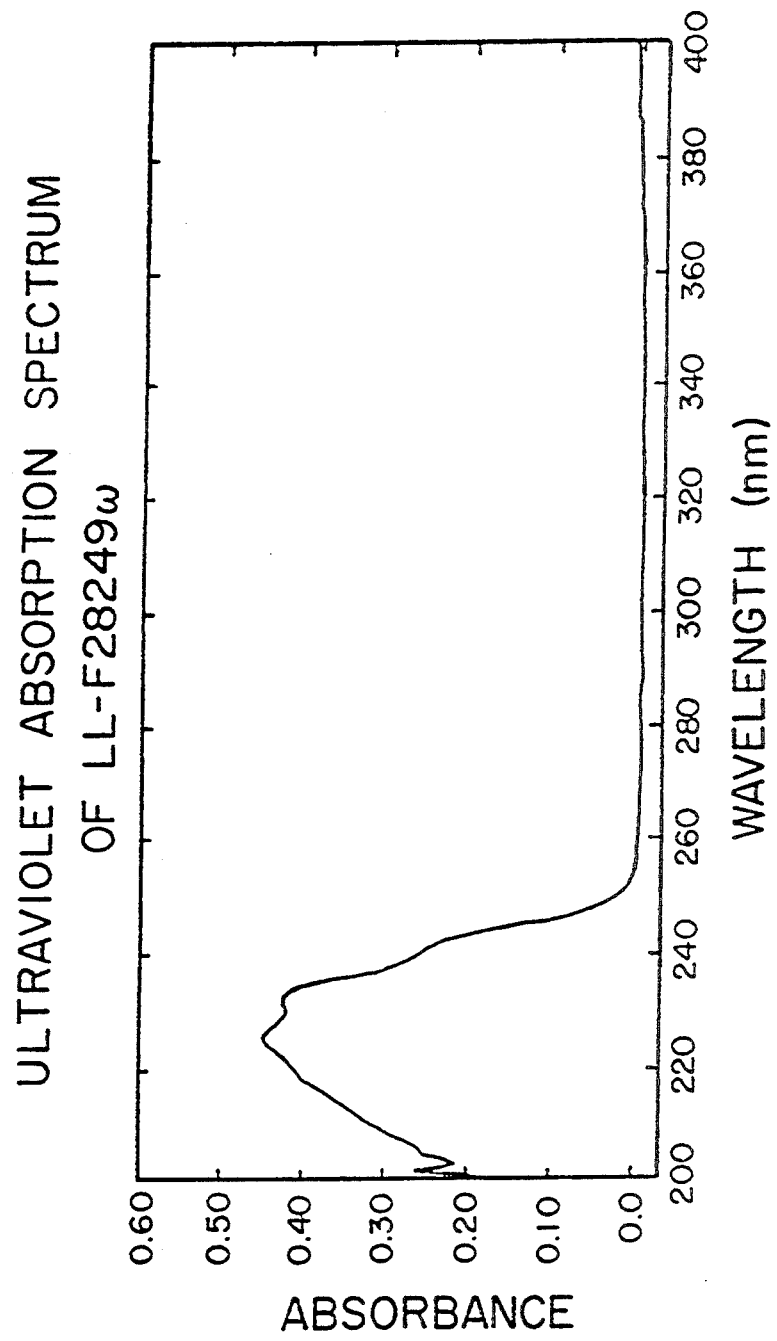
FIG. XV

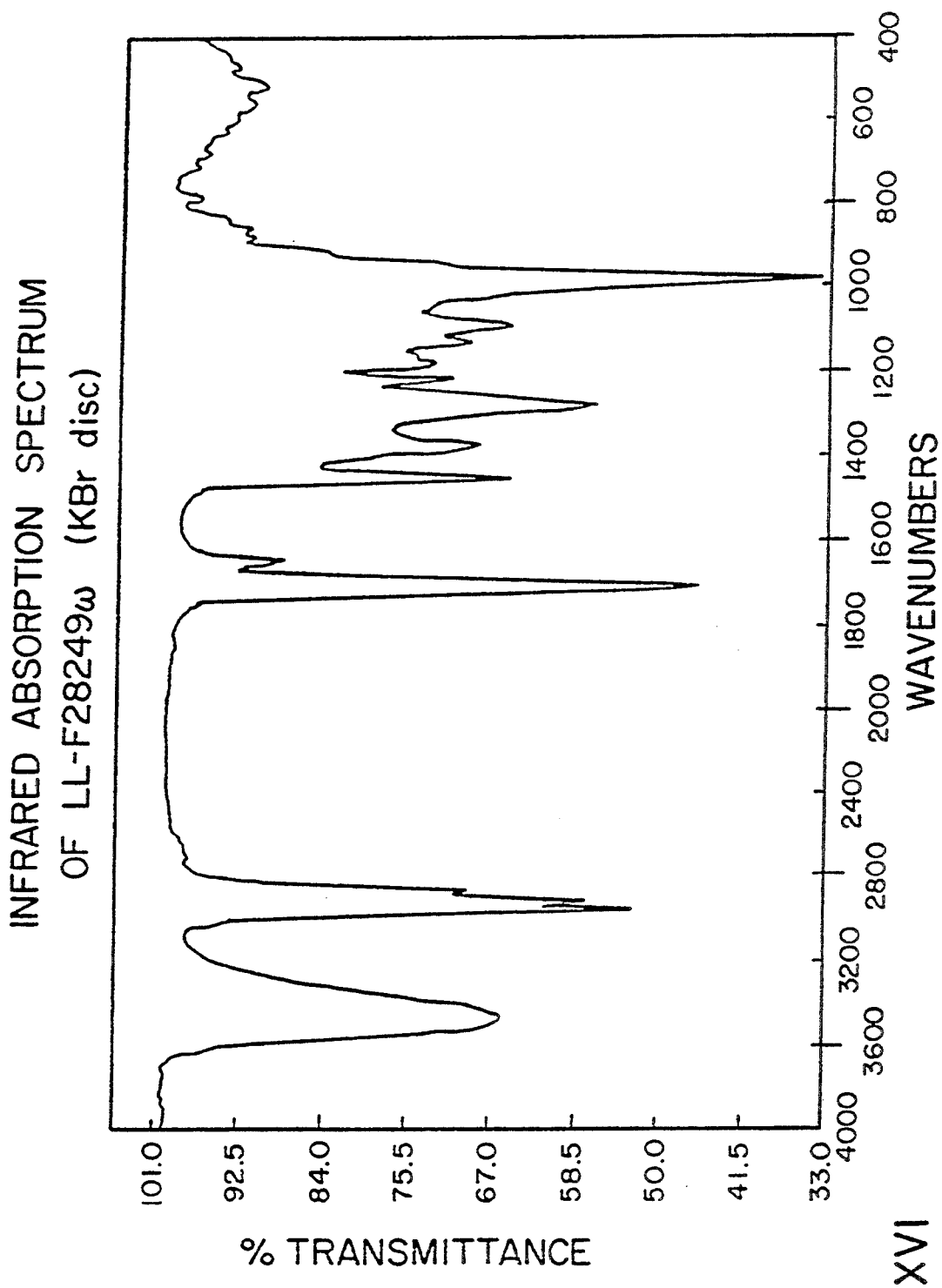
FIG. XVI

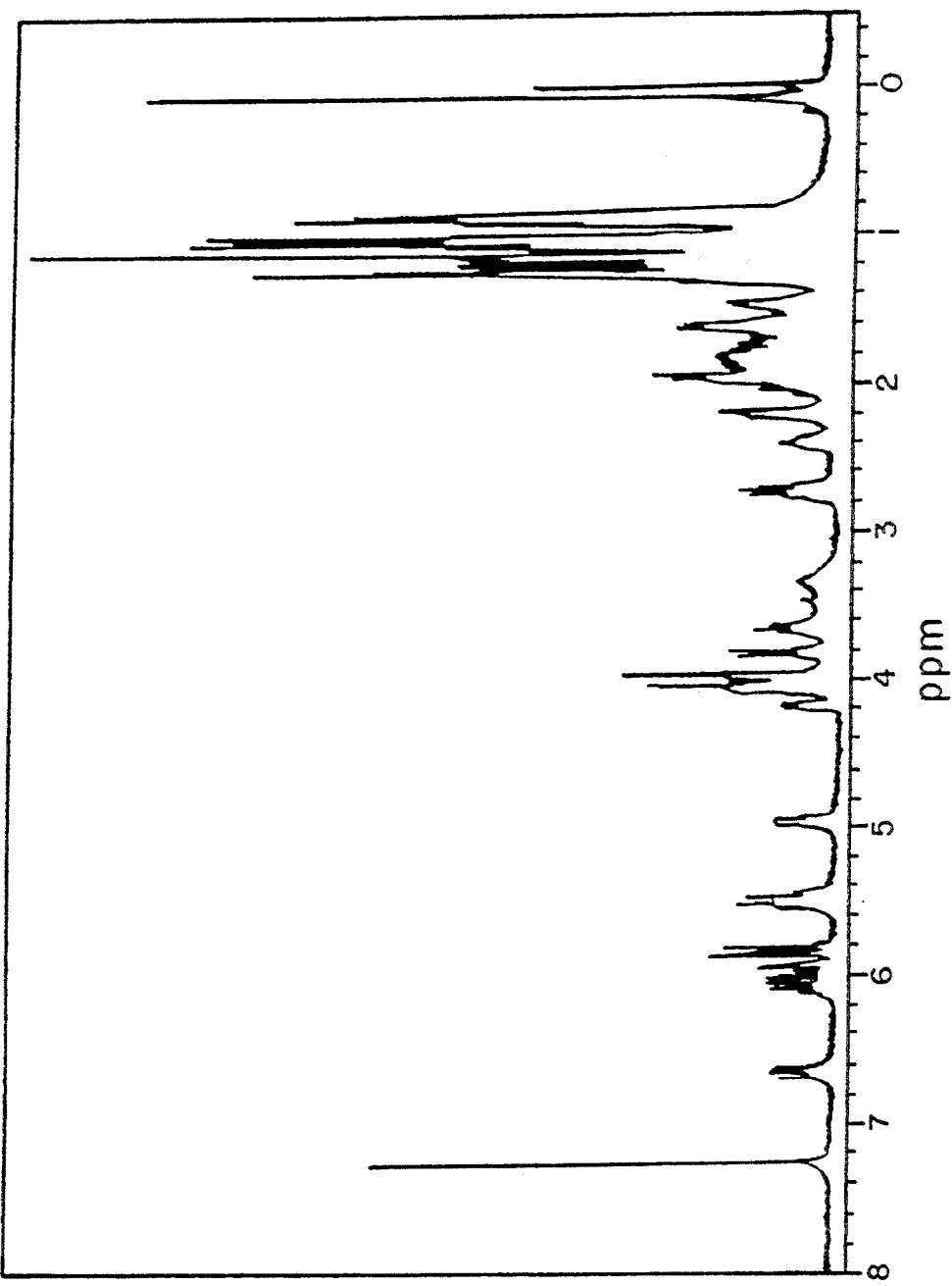

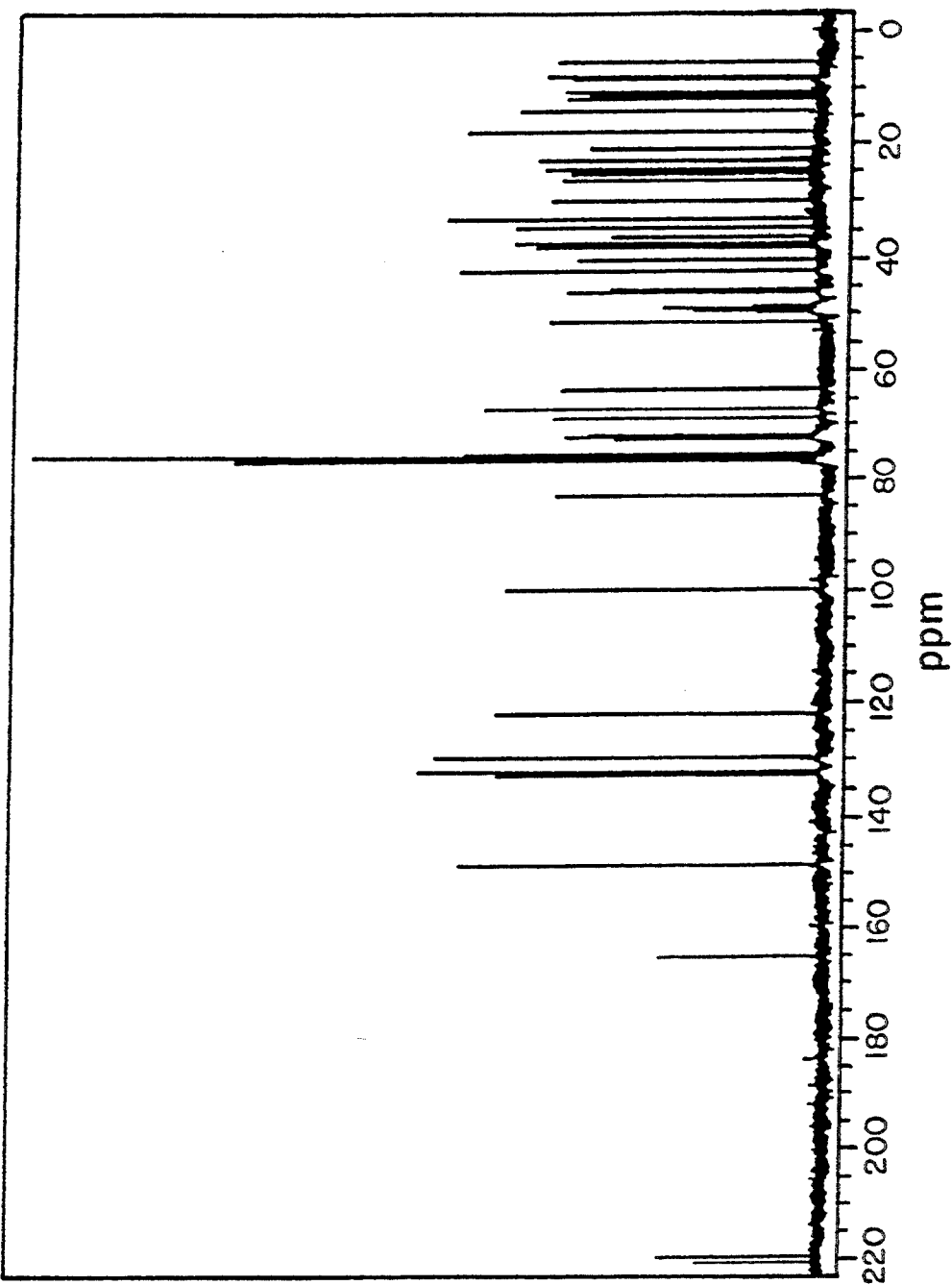
FIG. XVIII

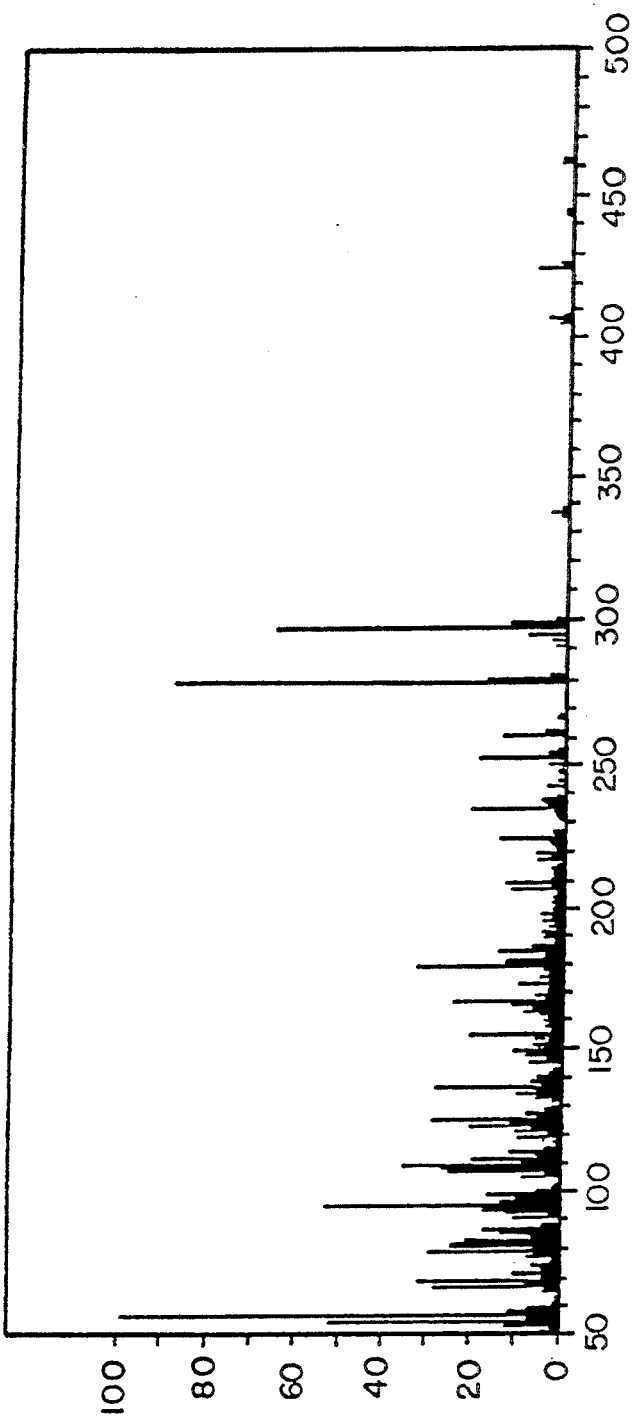
FIG. XIX

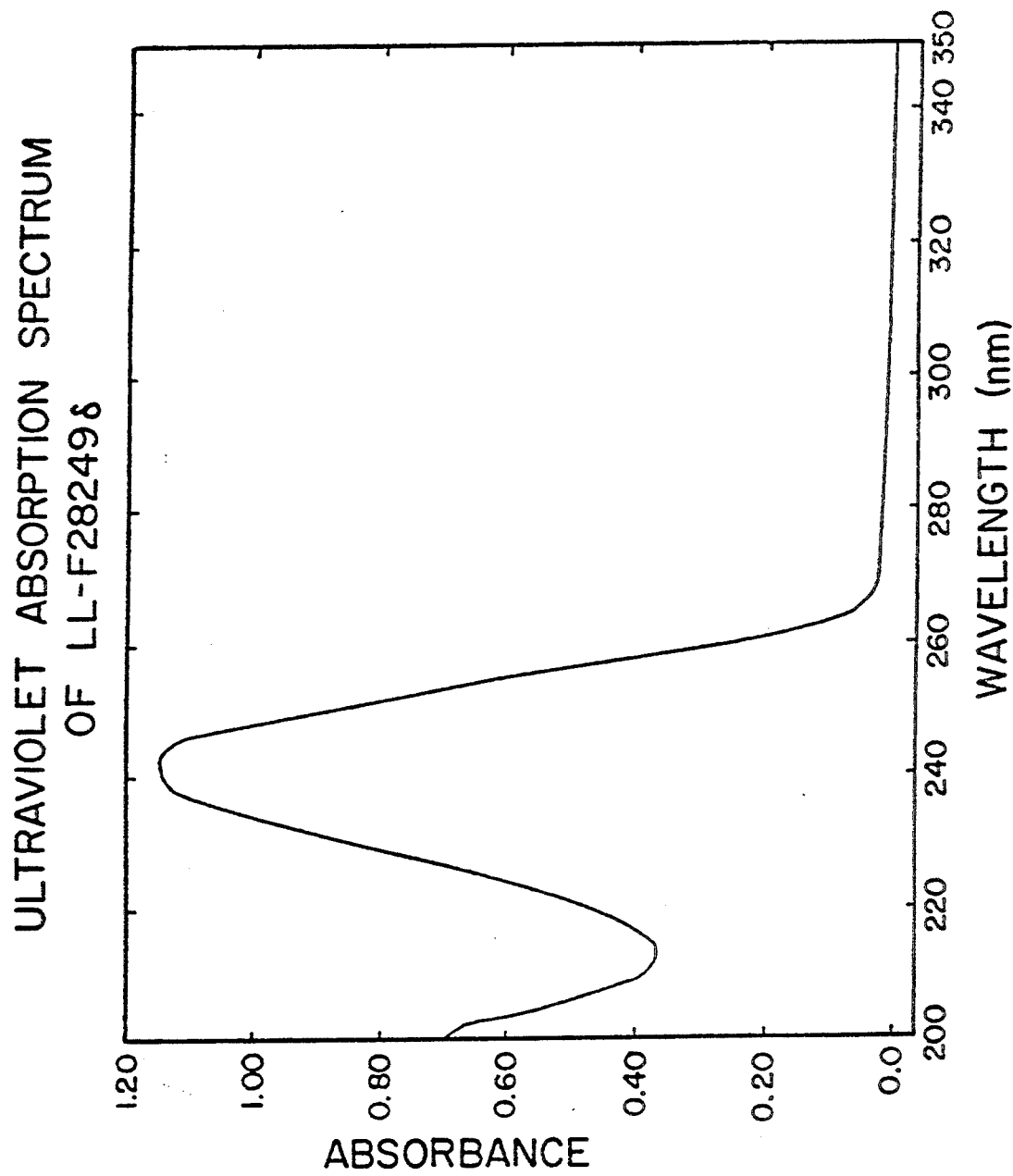
FIG. XX

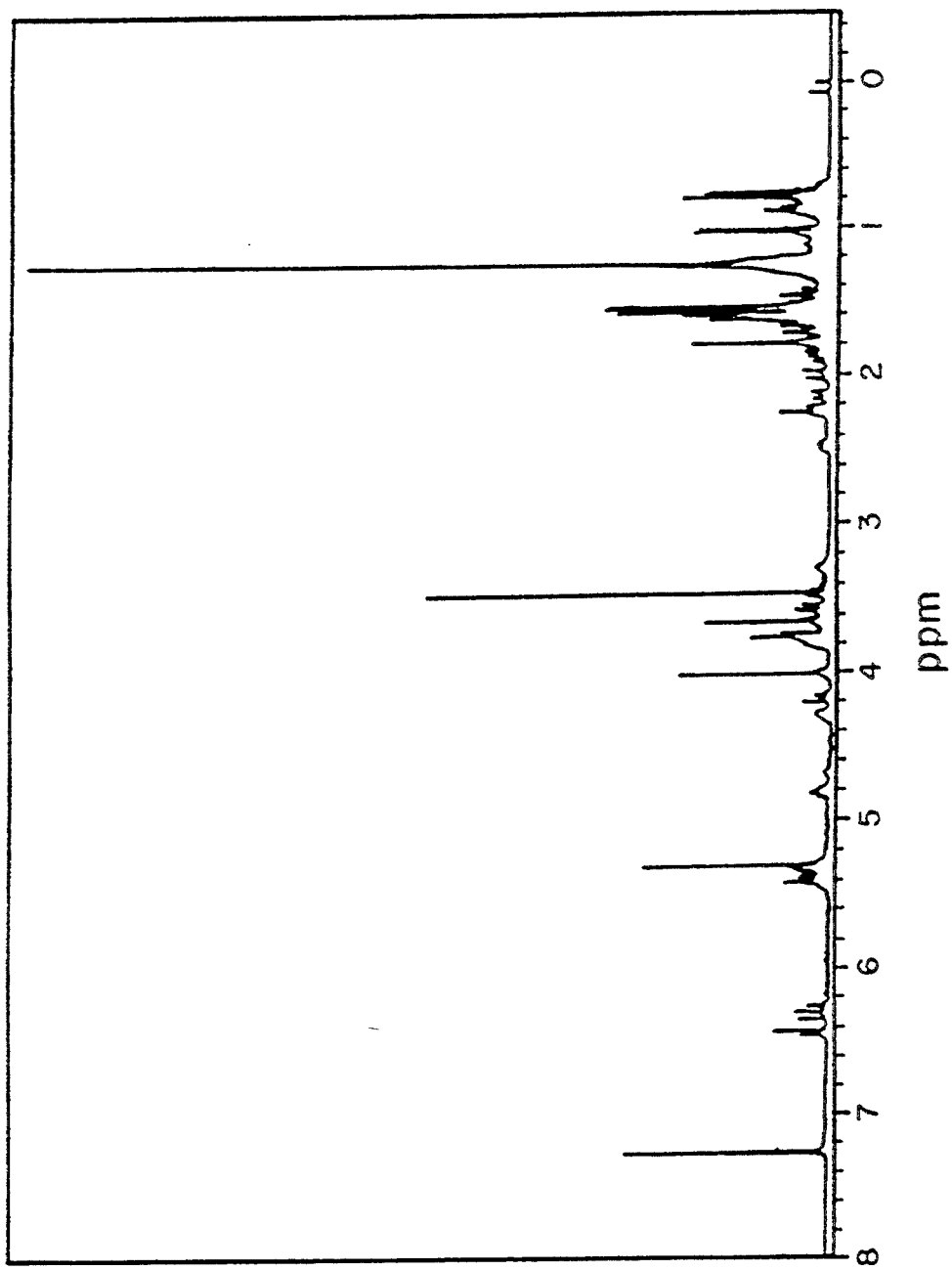
FIG. XXI

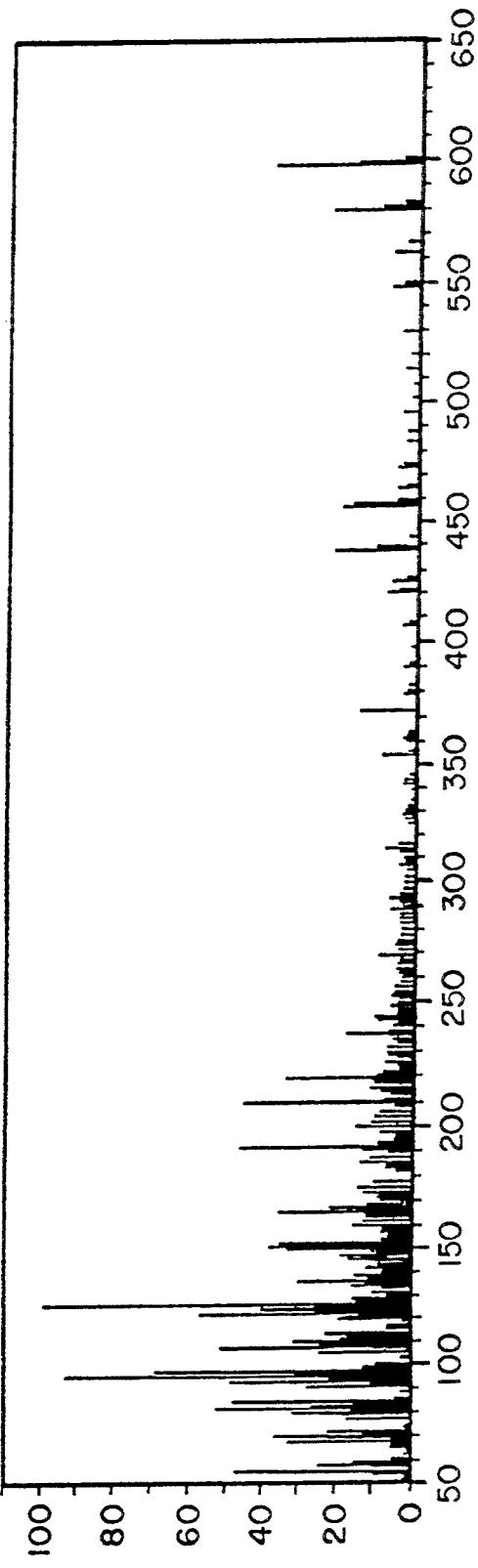
FIG. XXII — ELECTRON IMPACT MASS SPECTRUM OF LL-F28249 δ

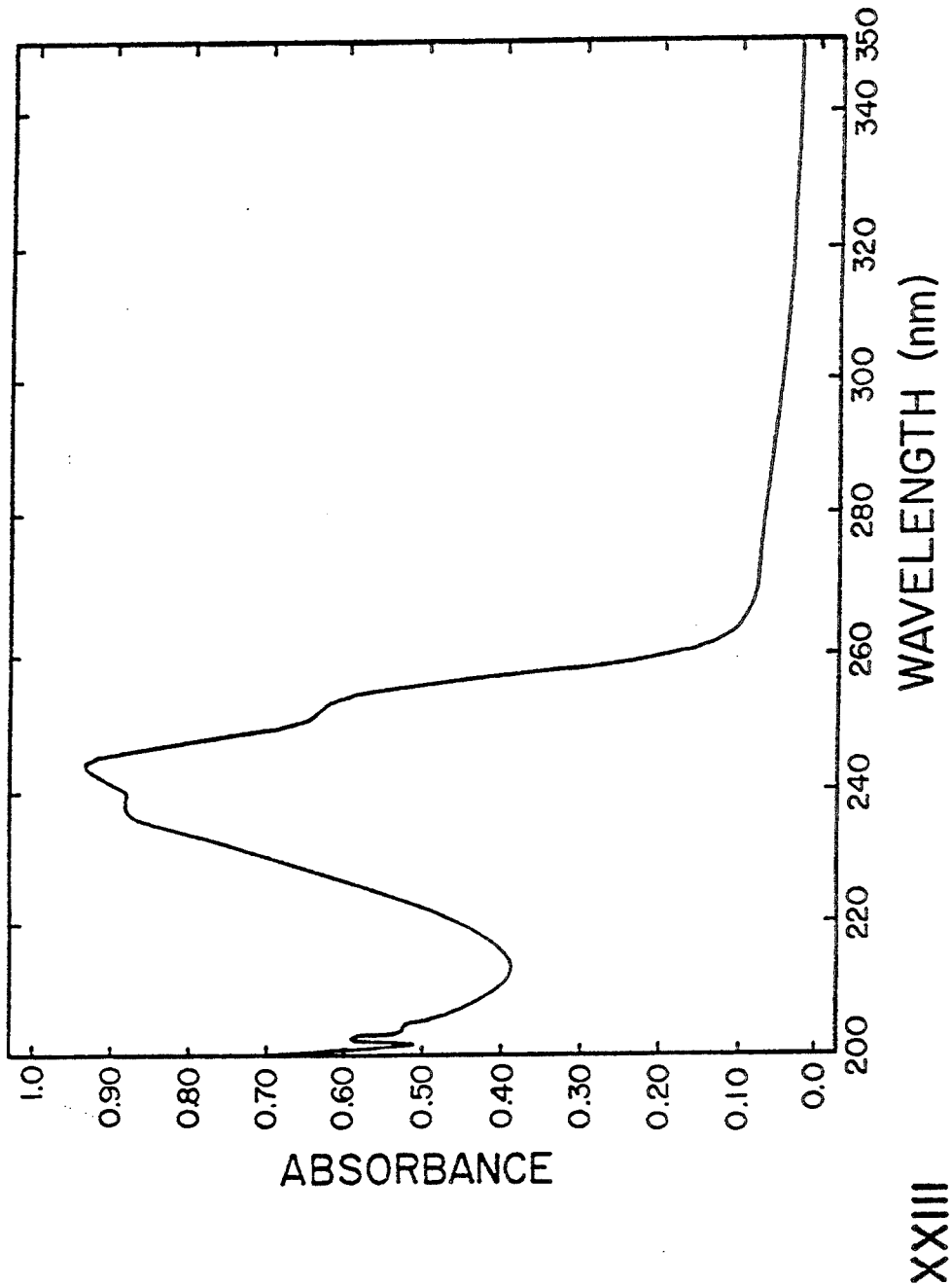
FIG. XXIII

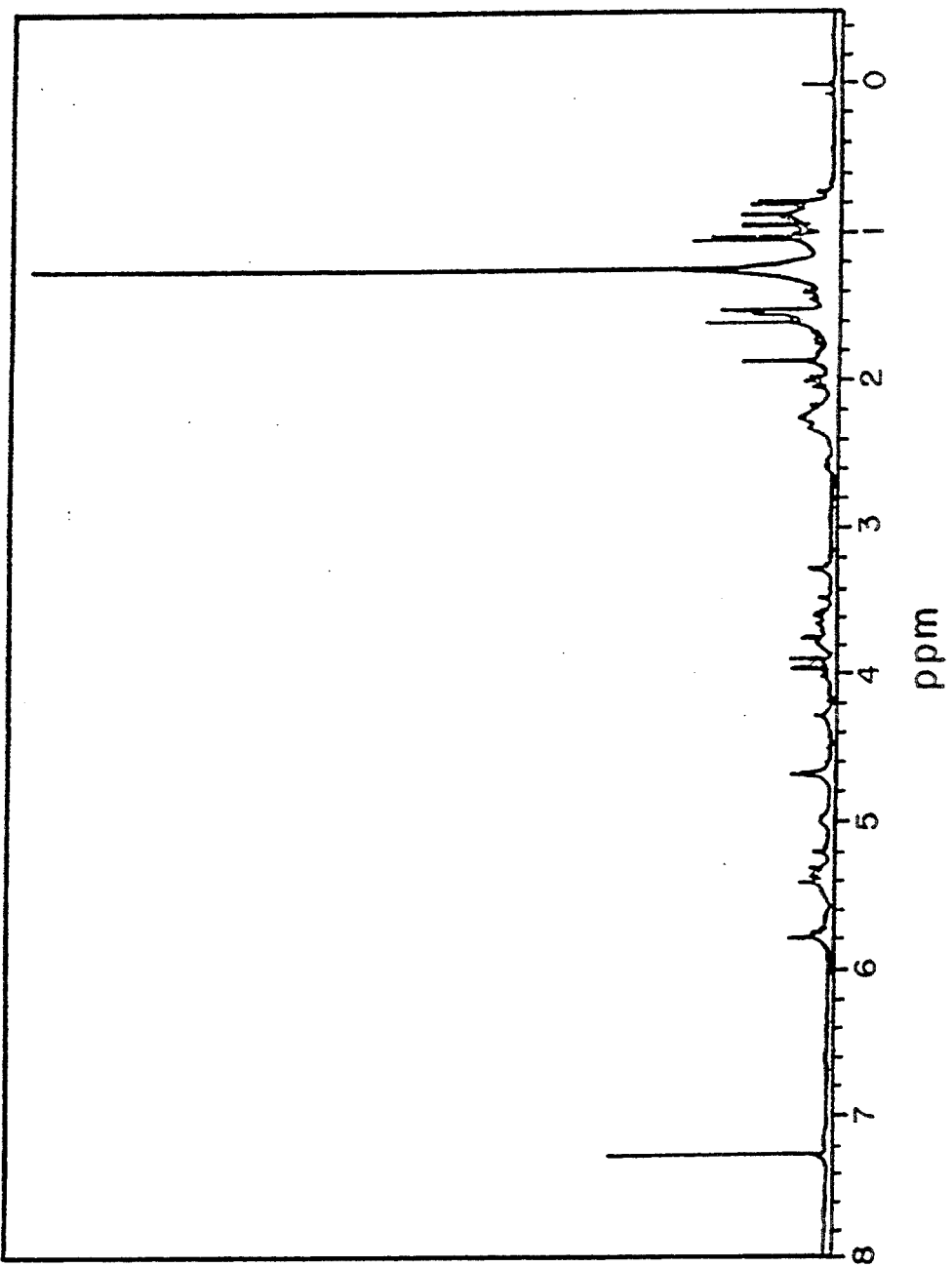
FIG. XXIV

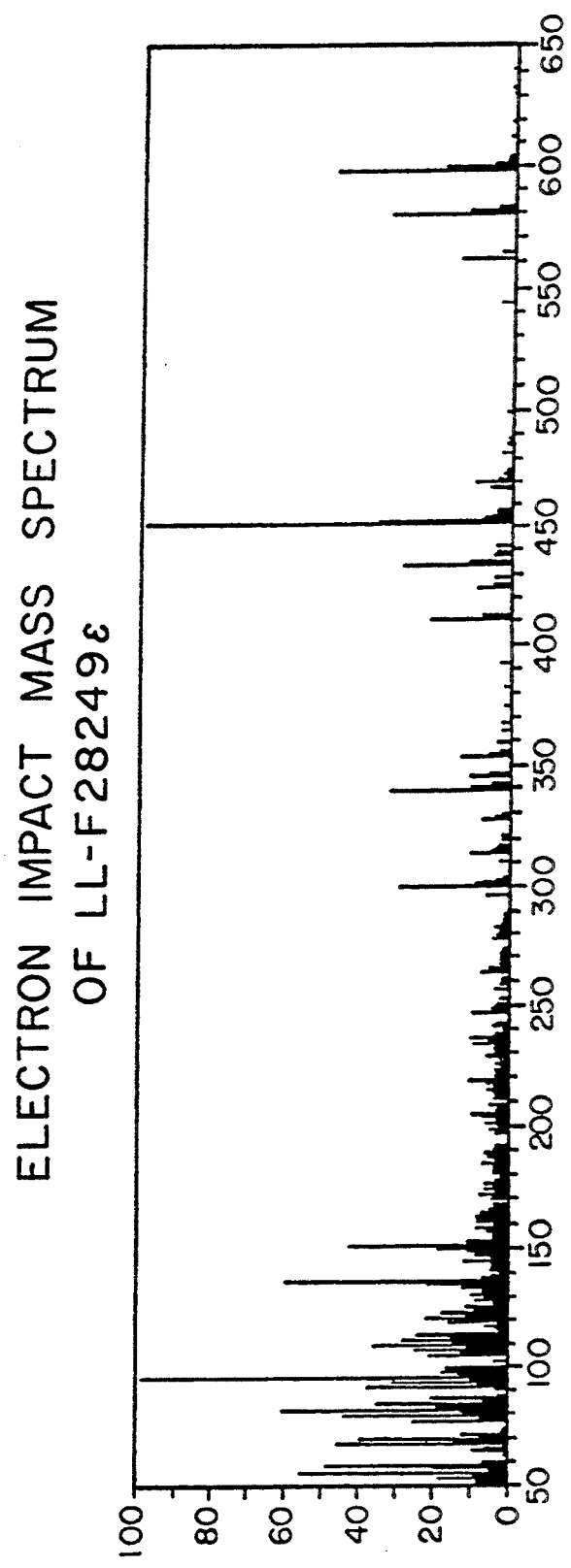
FIG. XXV

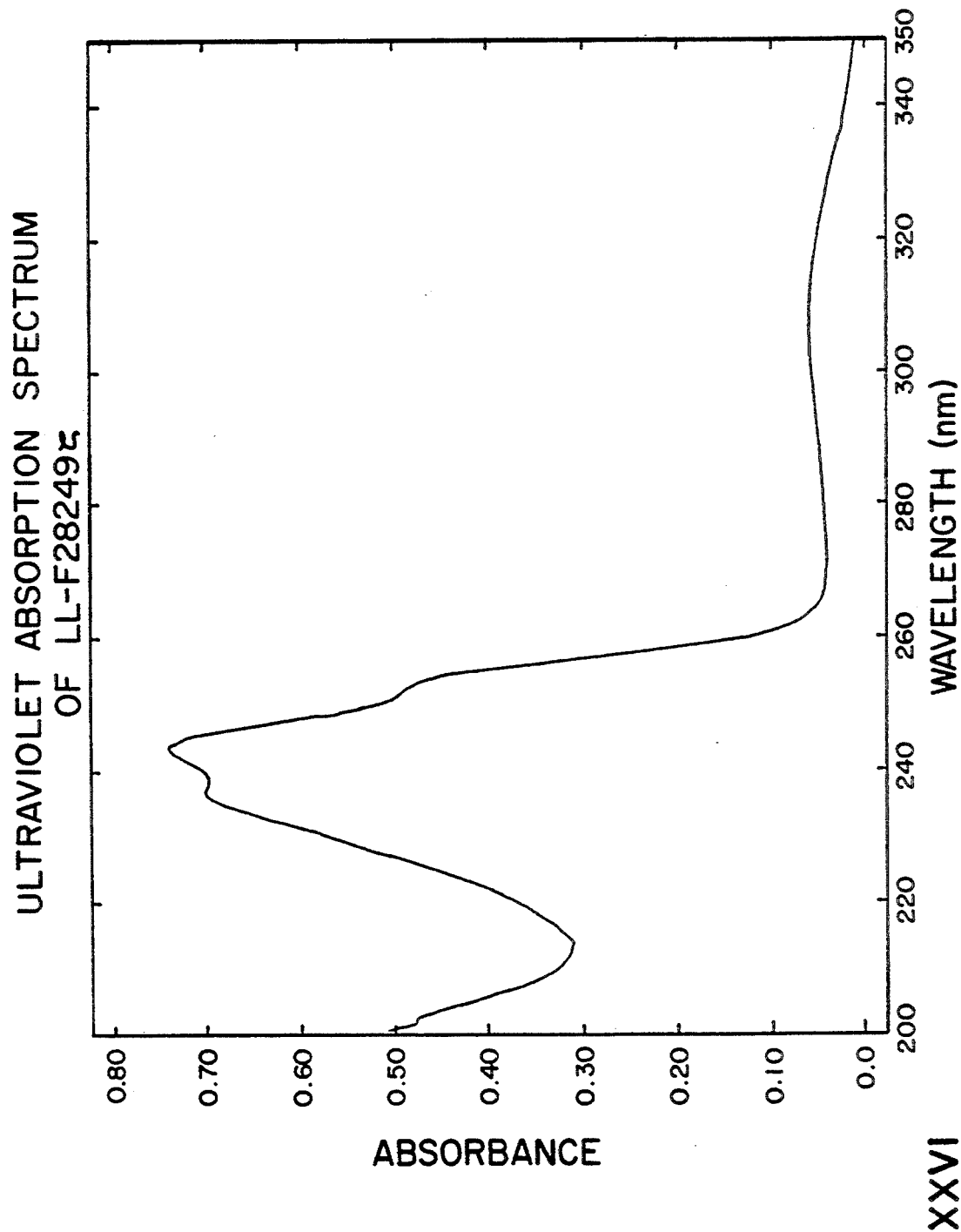
FIG. XXVI

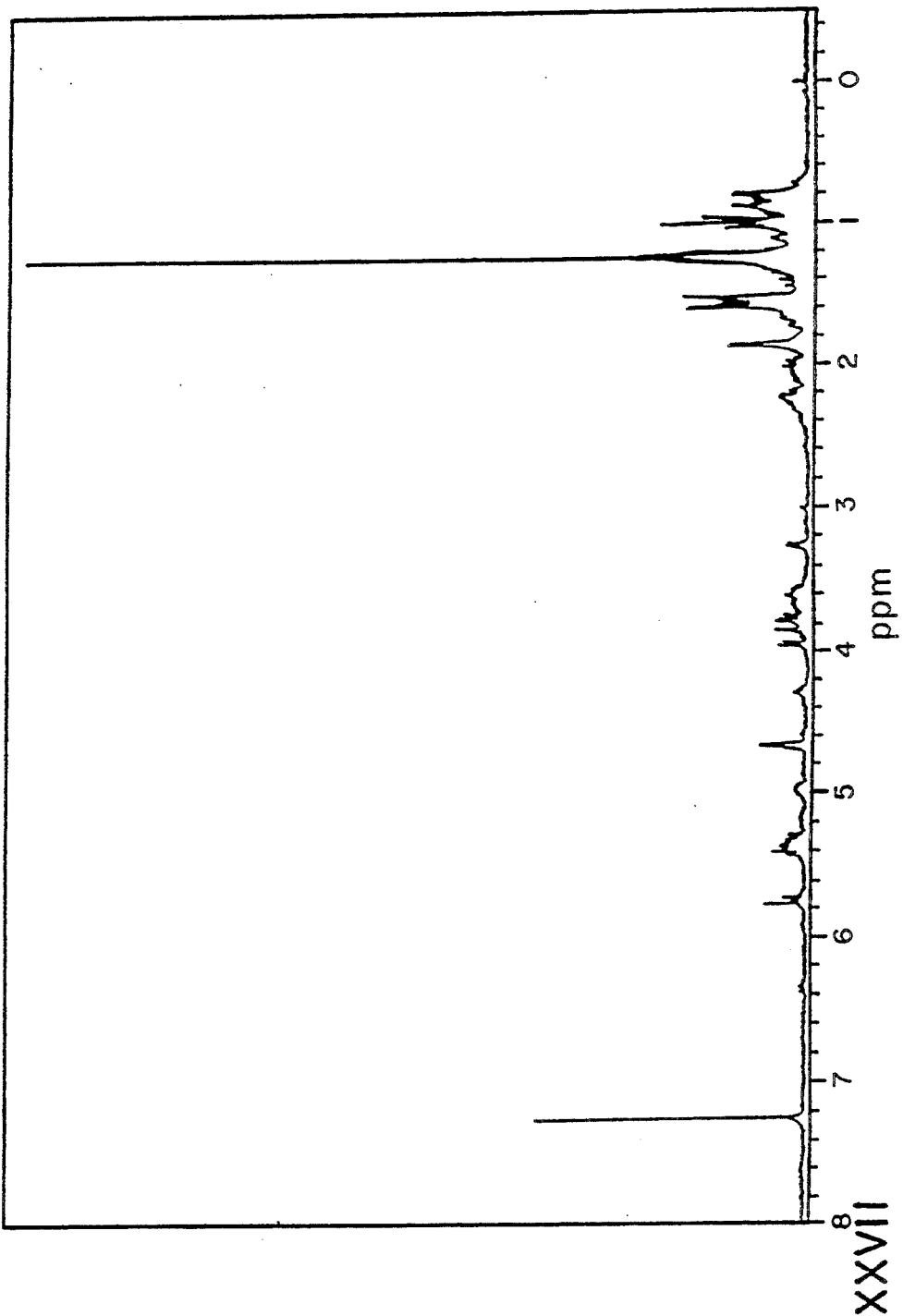

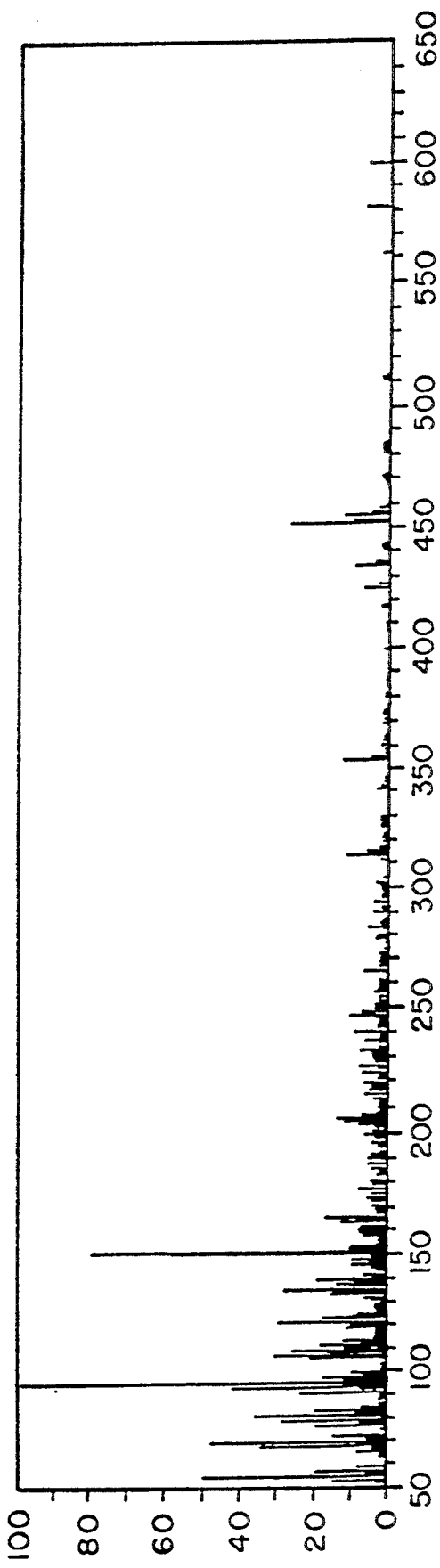
FIG. XXVIII

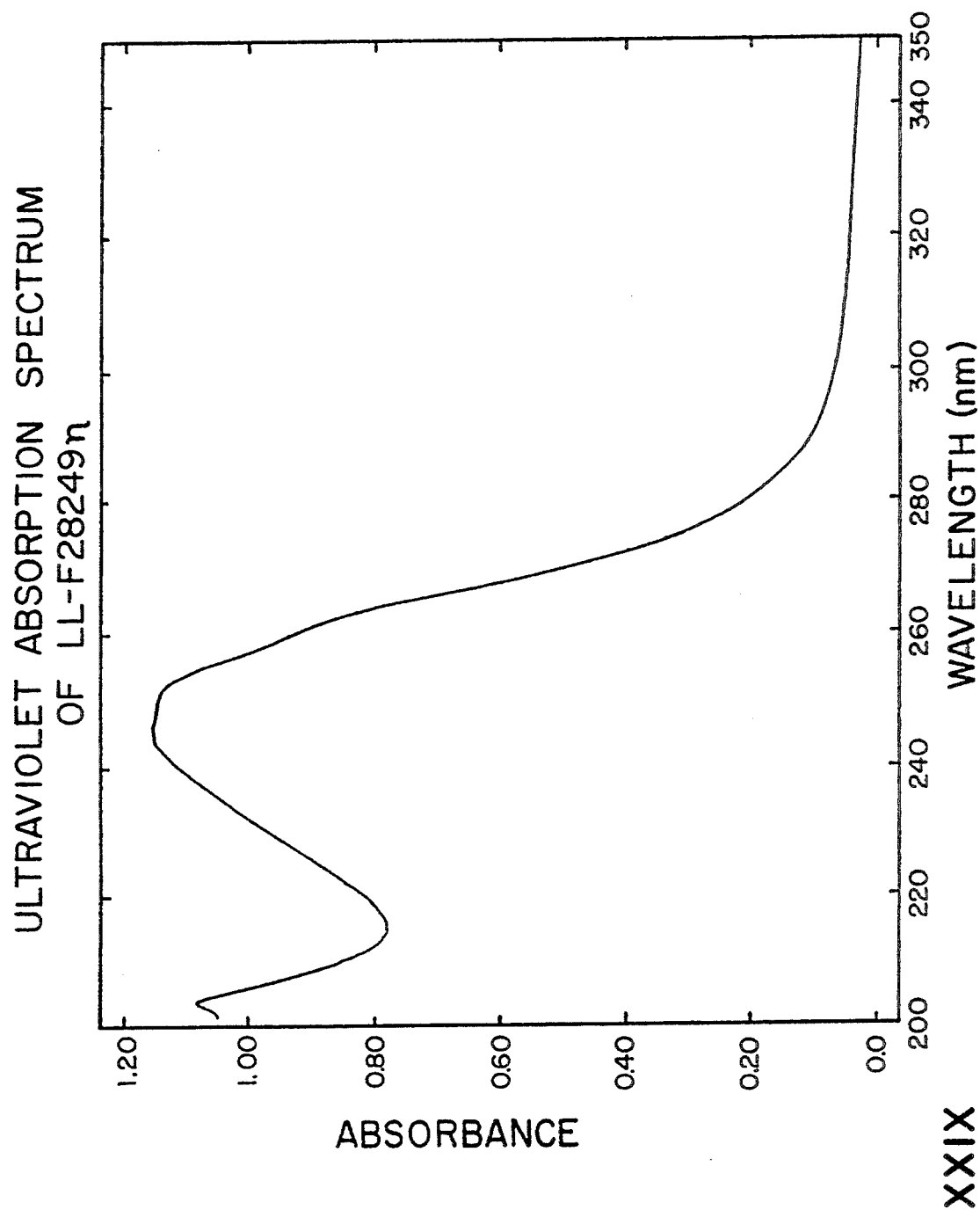
FIG. XXIX

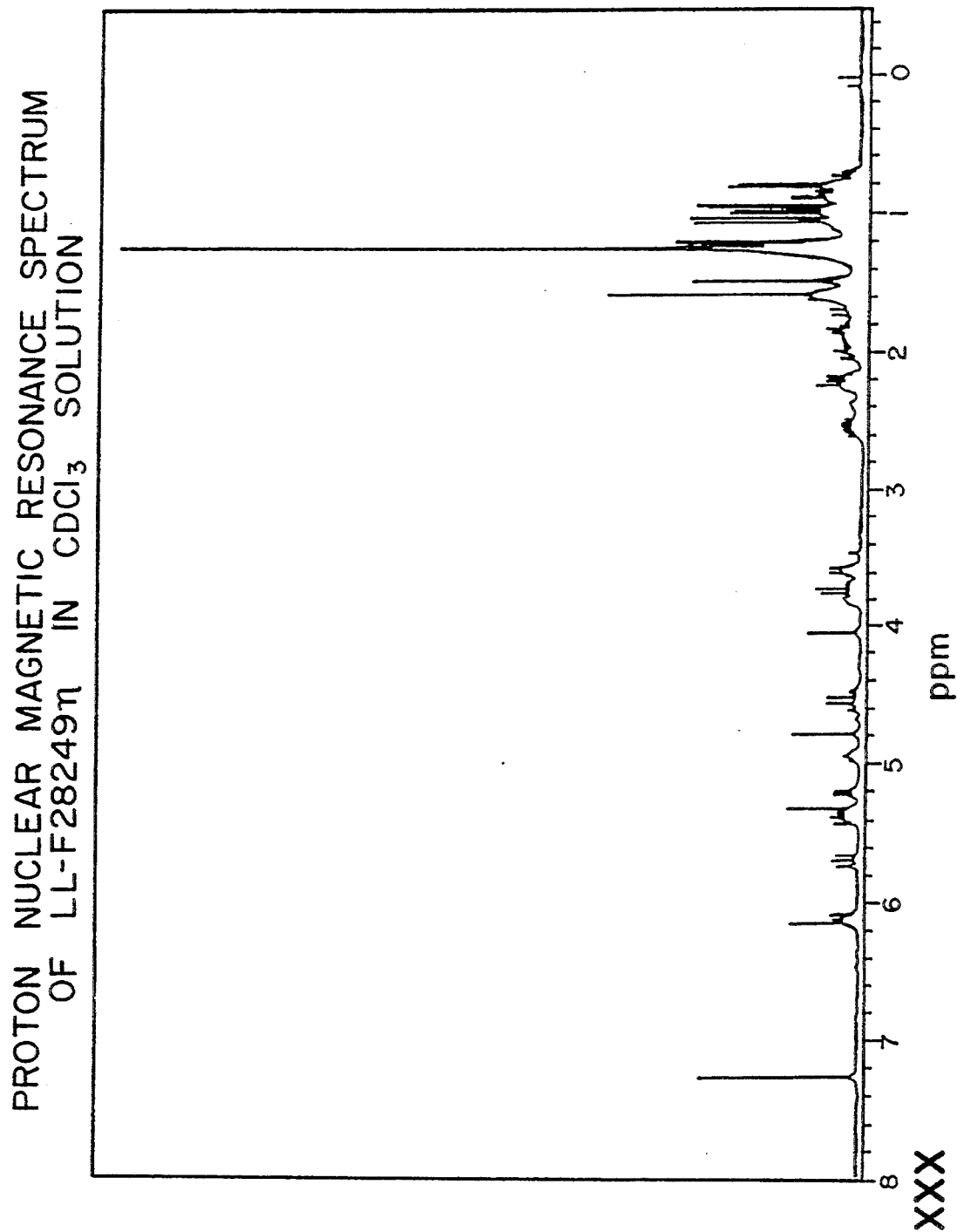
FIG. XXX

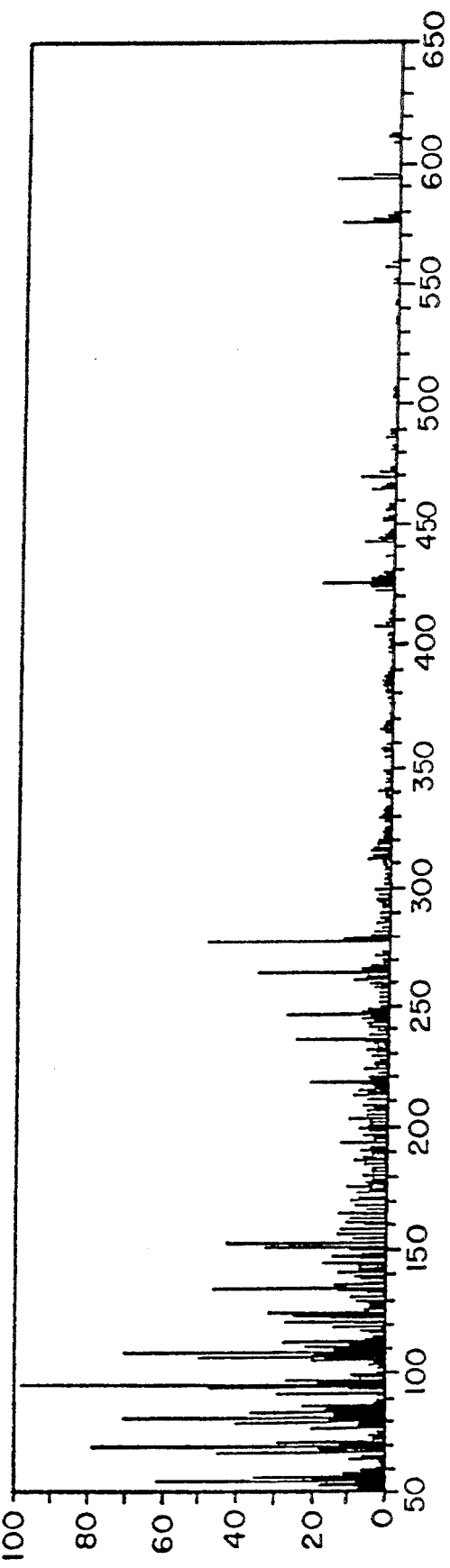
FIG. XXXI

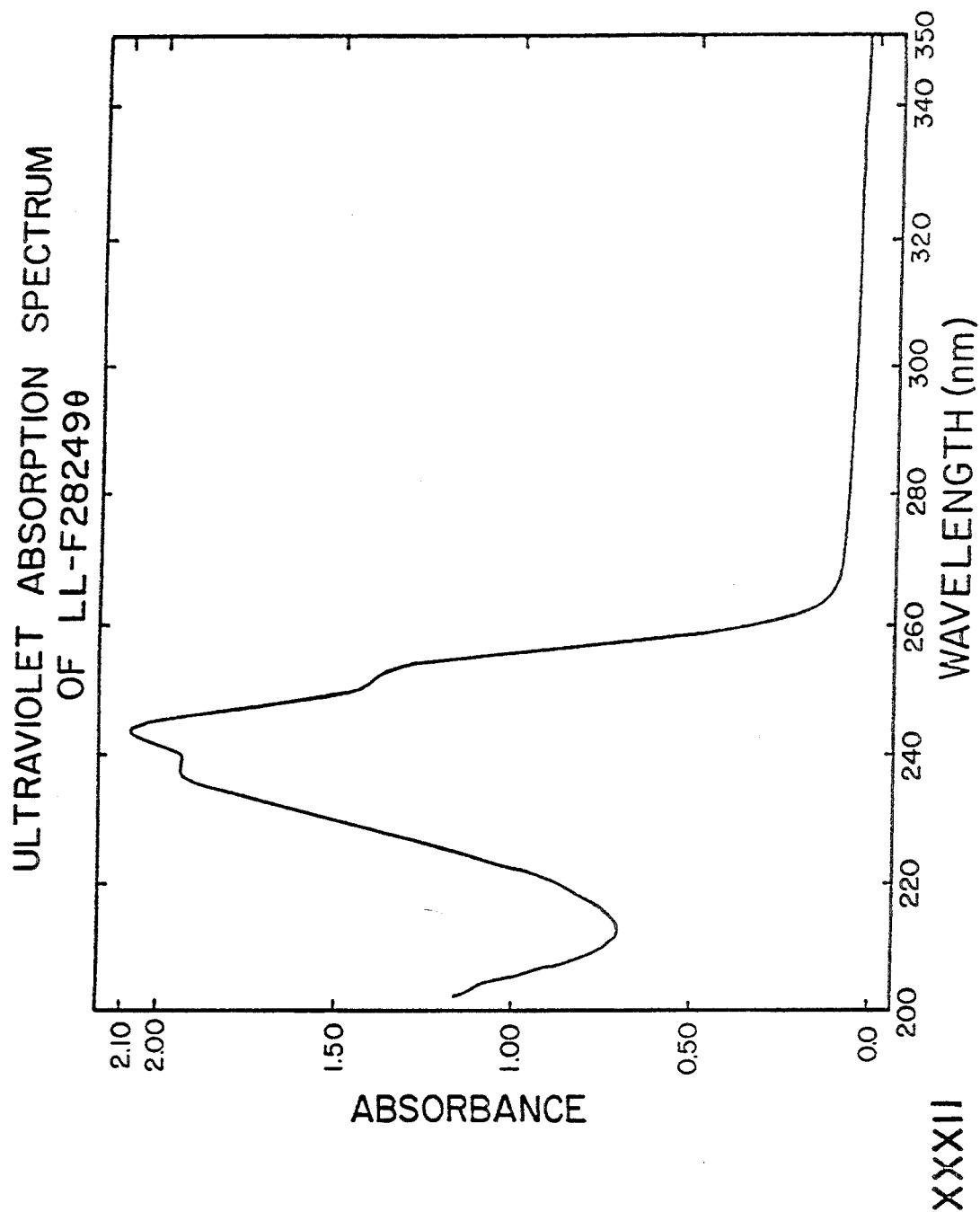

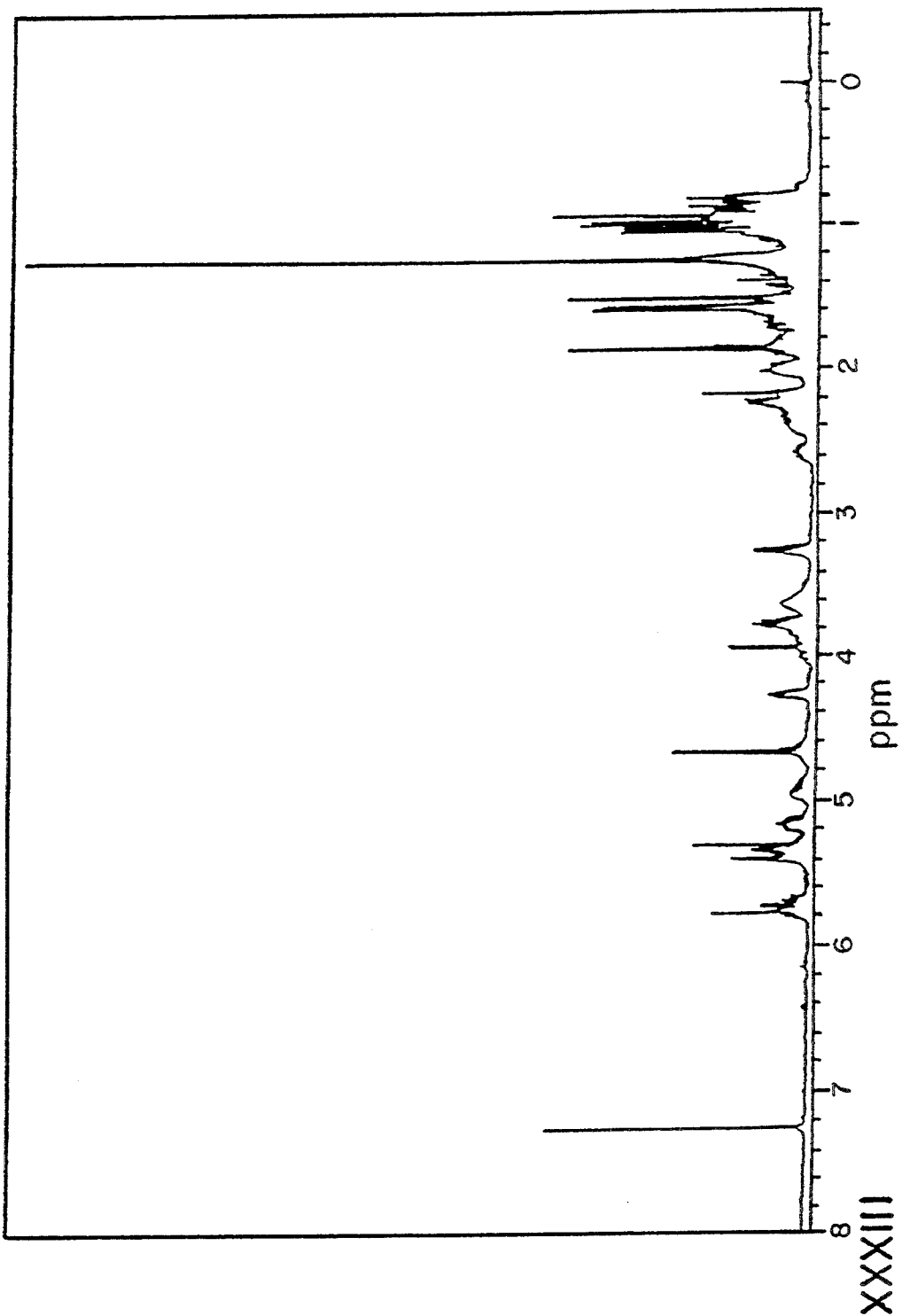
FIG. XXXIII

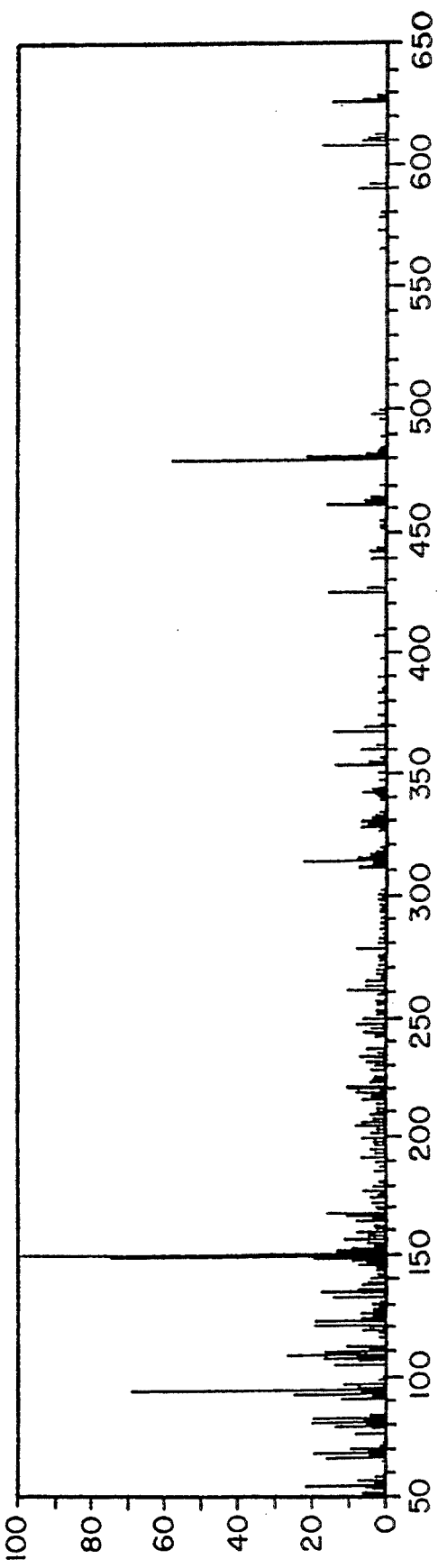
FIG. XXXIV

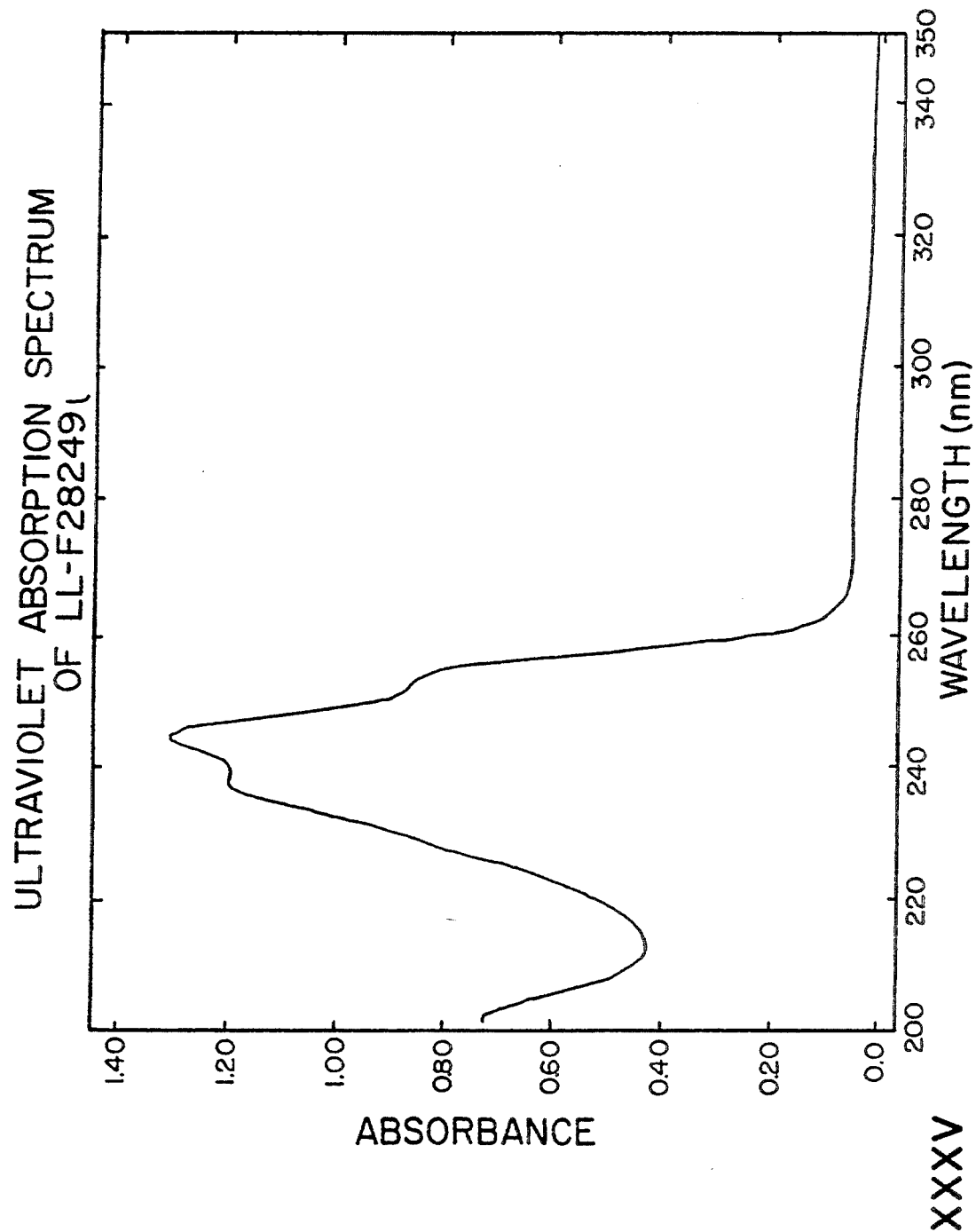
FIG. XXXV

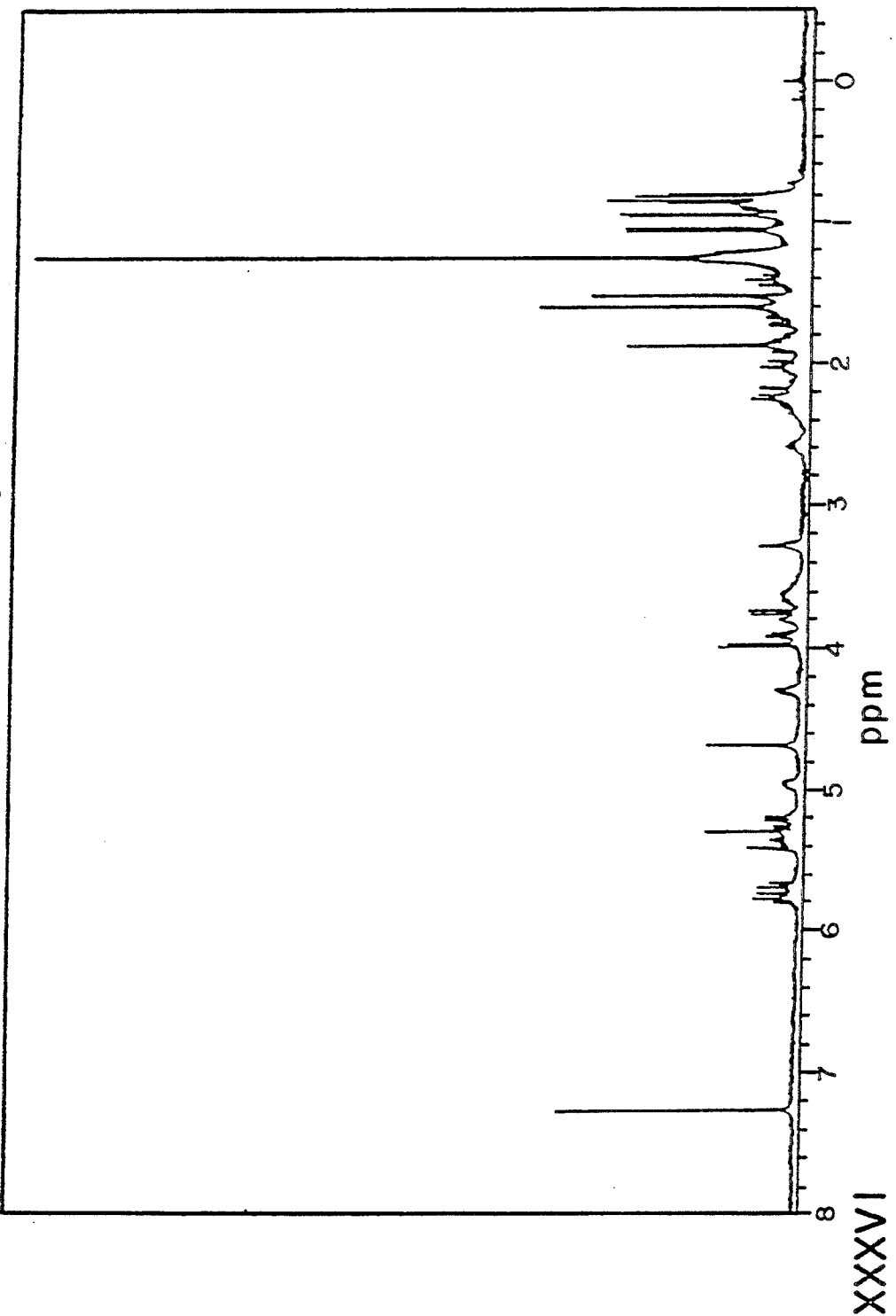
FIG. XXXVI PROTON NUCLEAR MAGNETIC RESONANCE SPECTRUM OF LL-F28249ι IN CDCl₃ SOLUTION

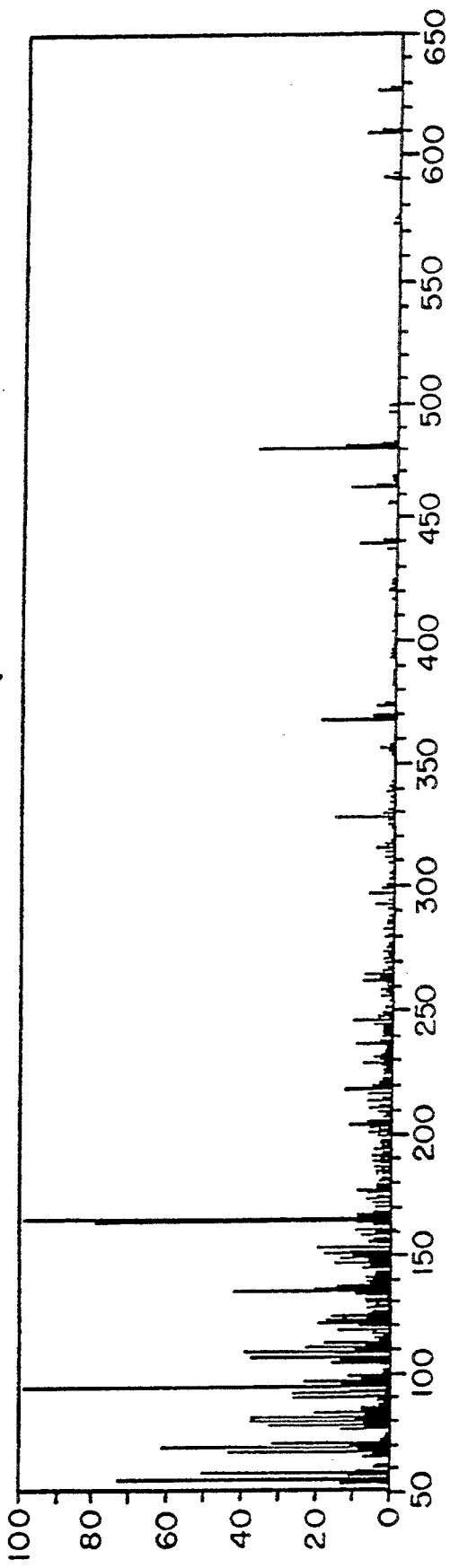
FIG. XXXVII

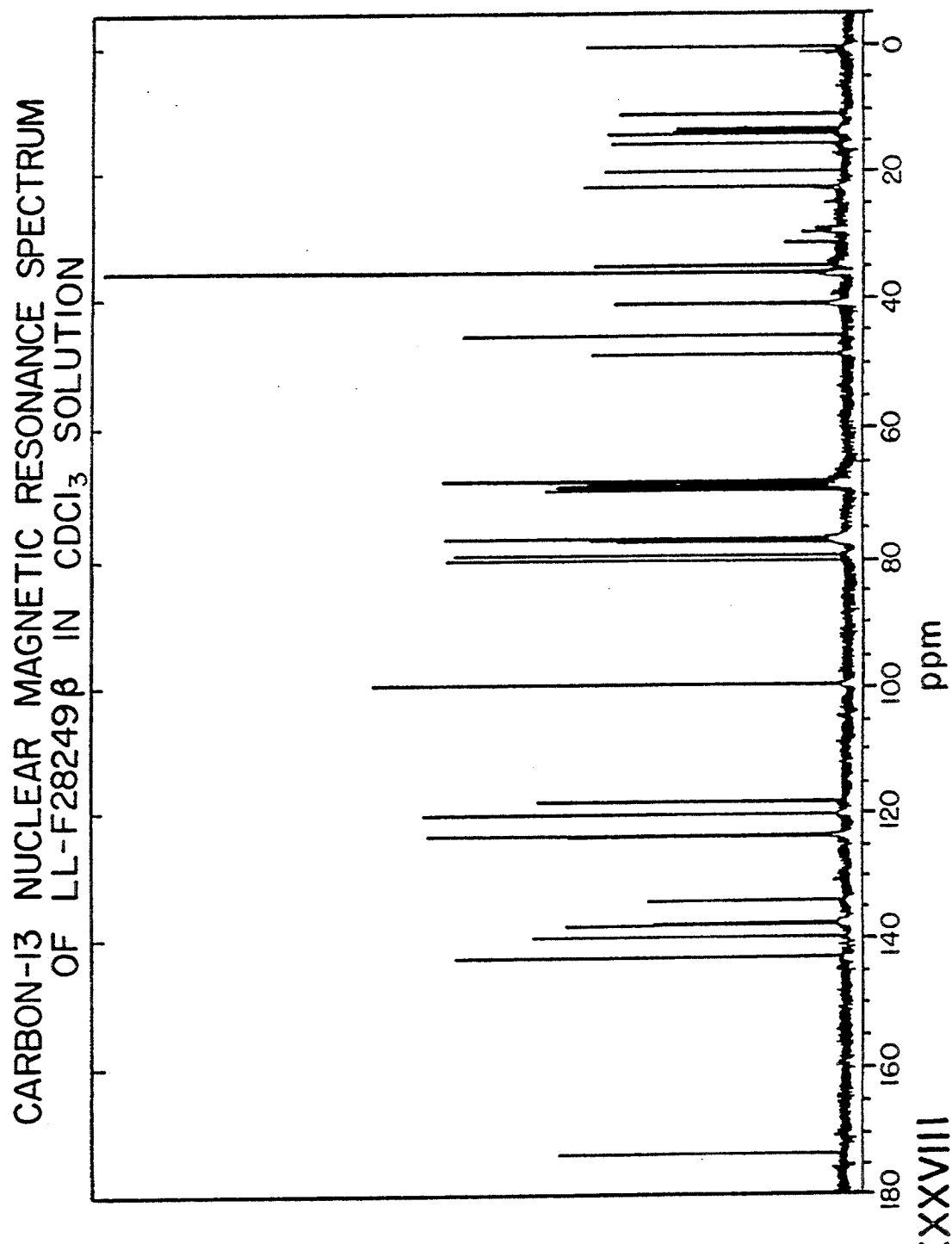
FIG. XXXVIII

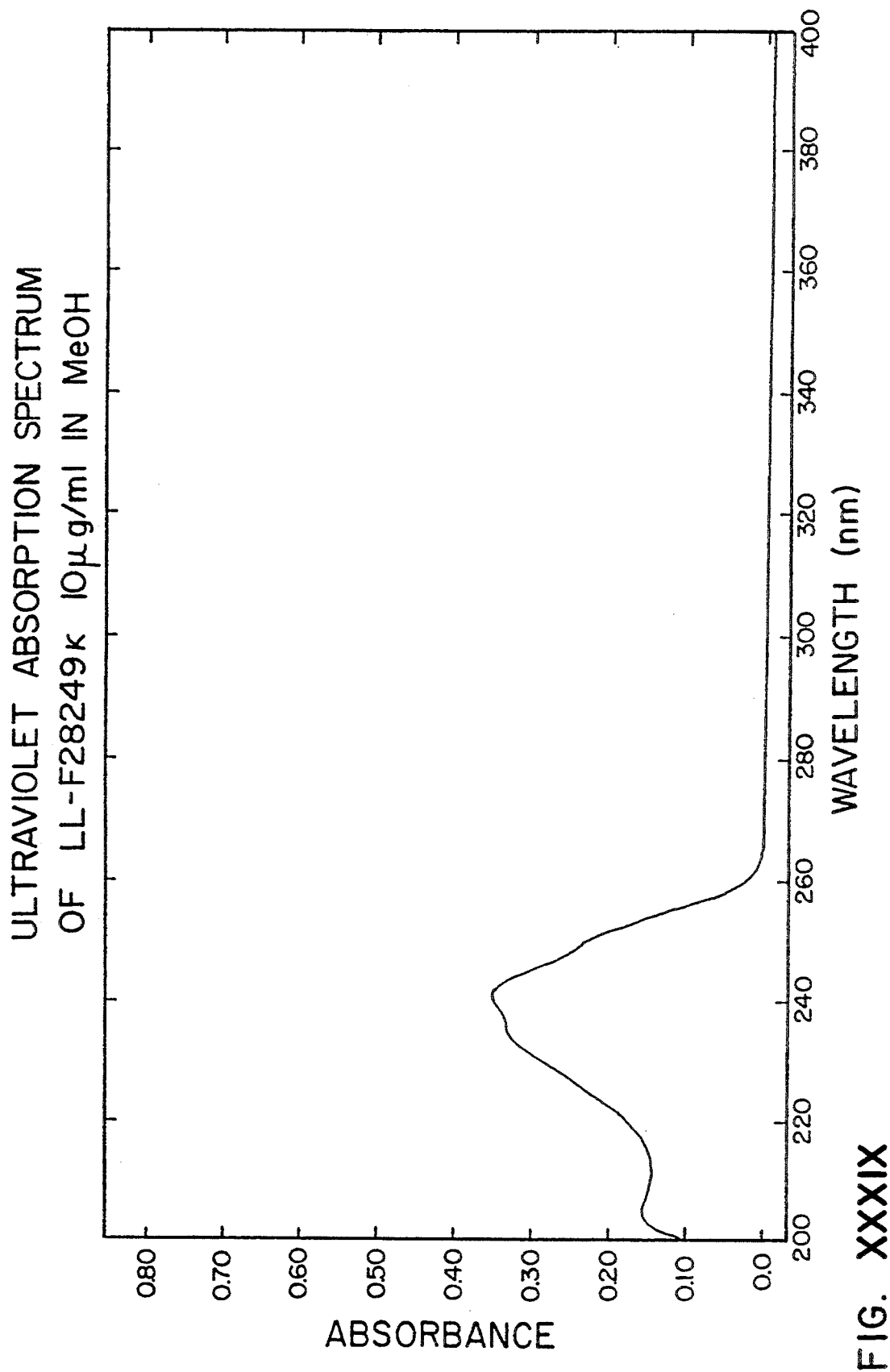

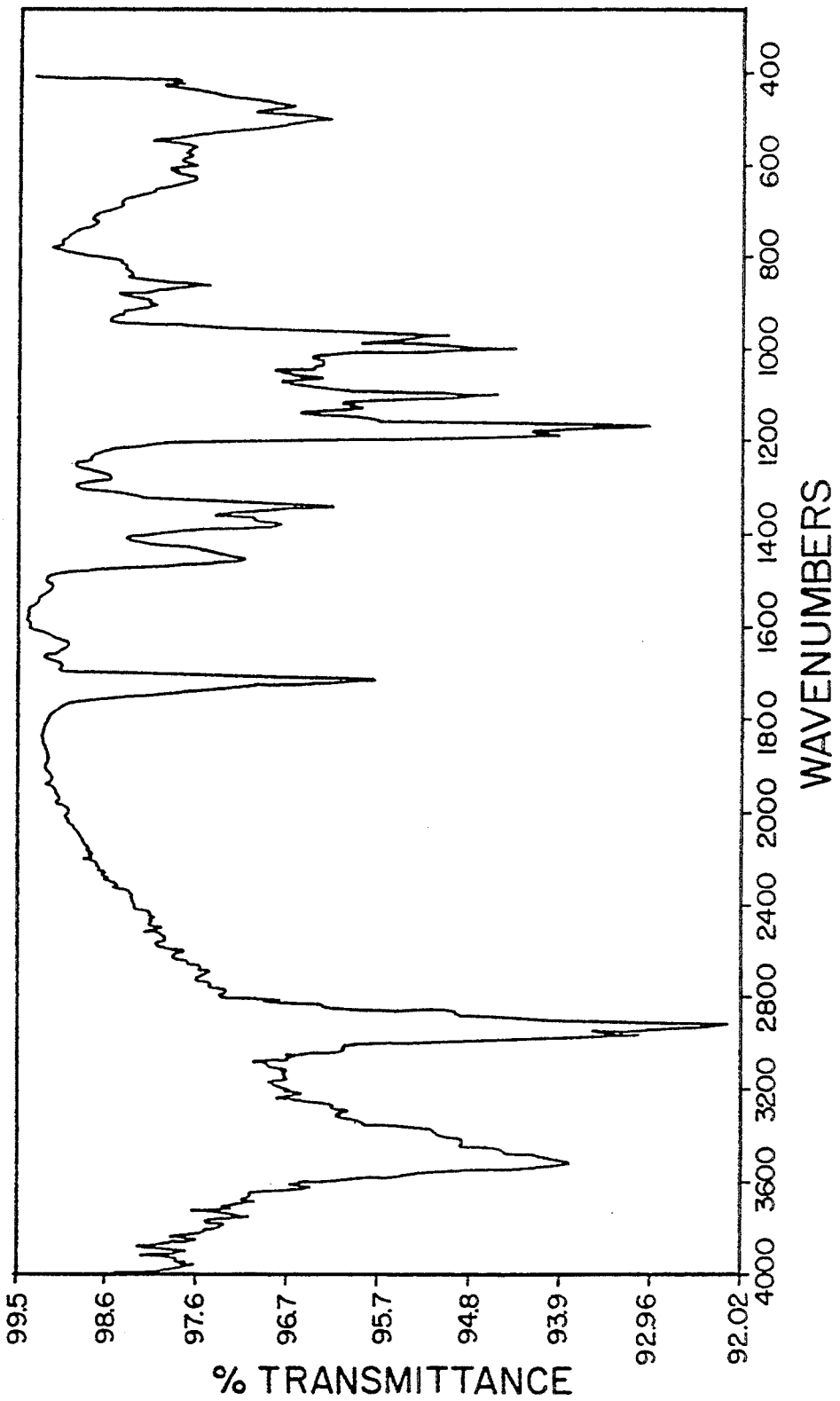
FIG. XL

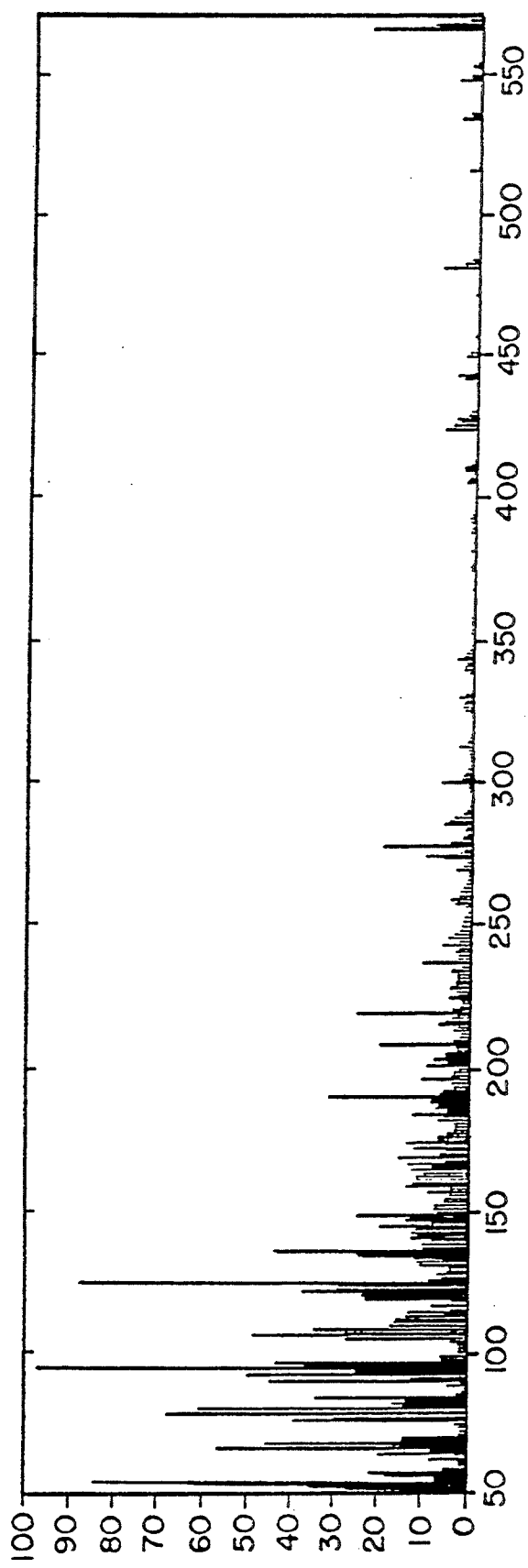
FIG. XLI

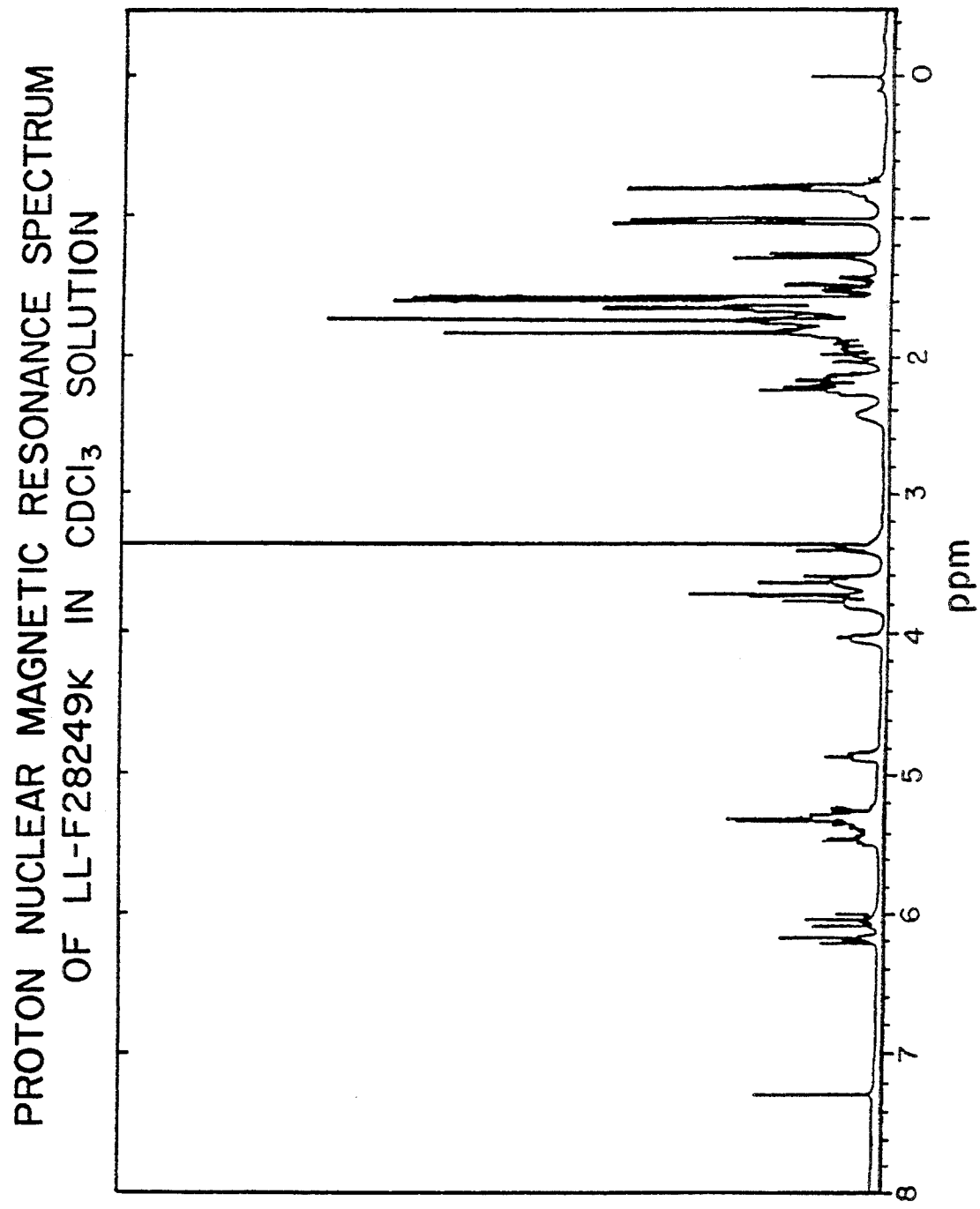
FIG. XLII

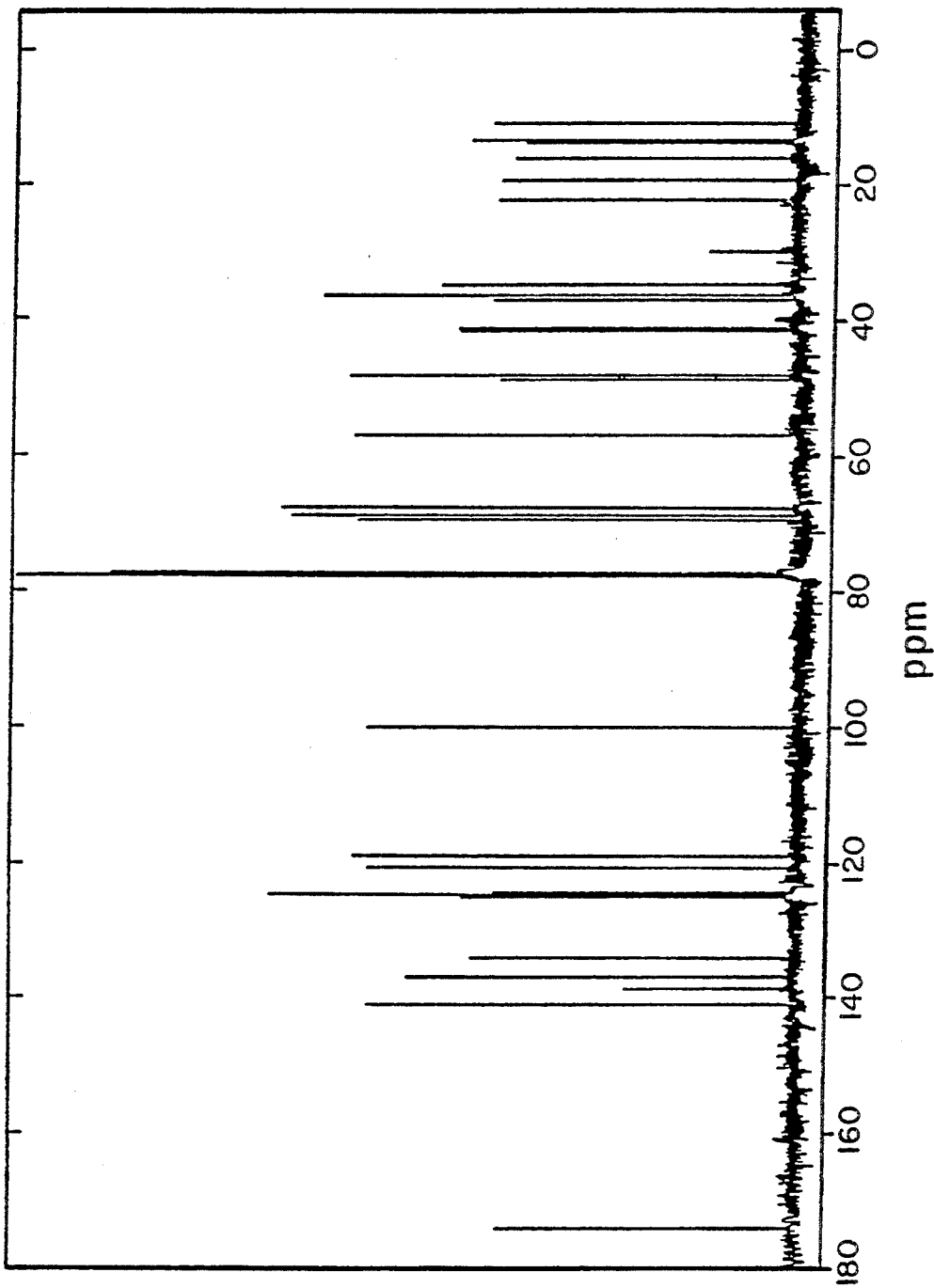
FIG. XLIII

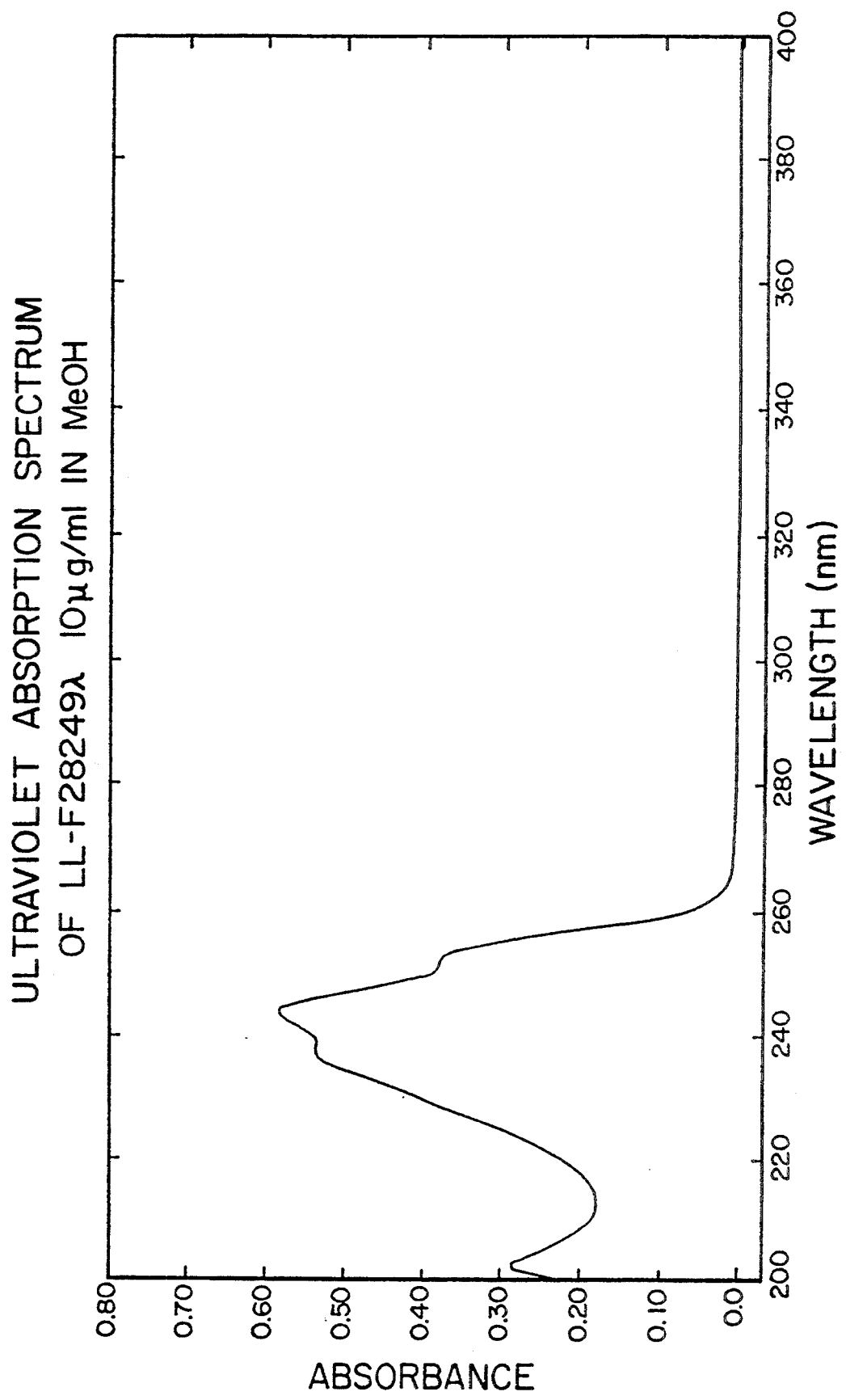
FIG. XLIV

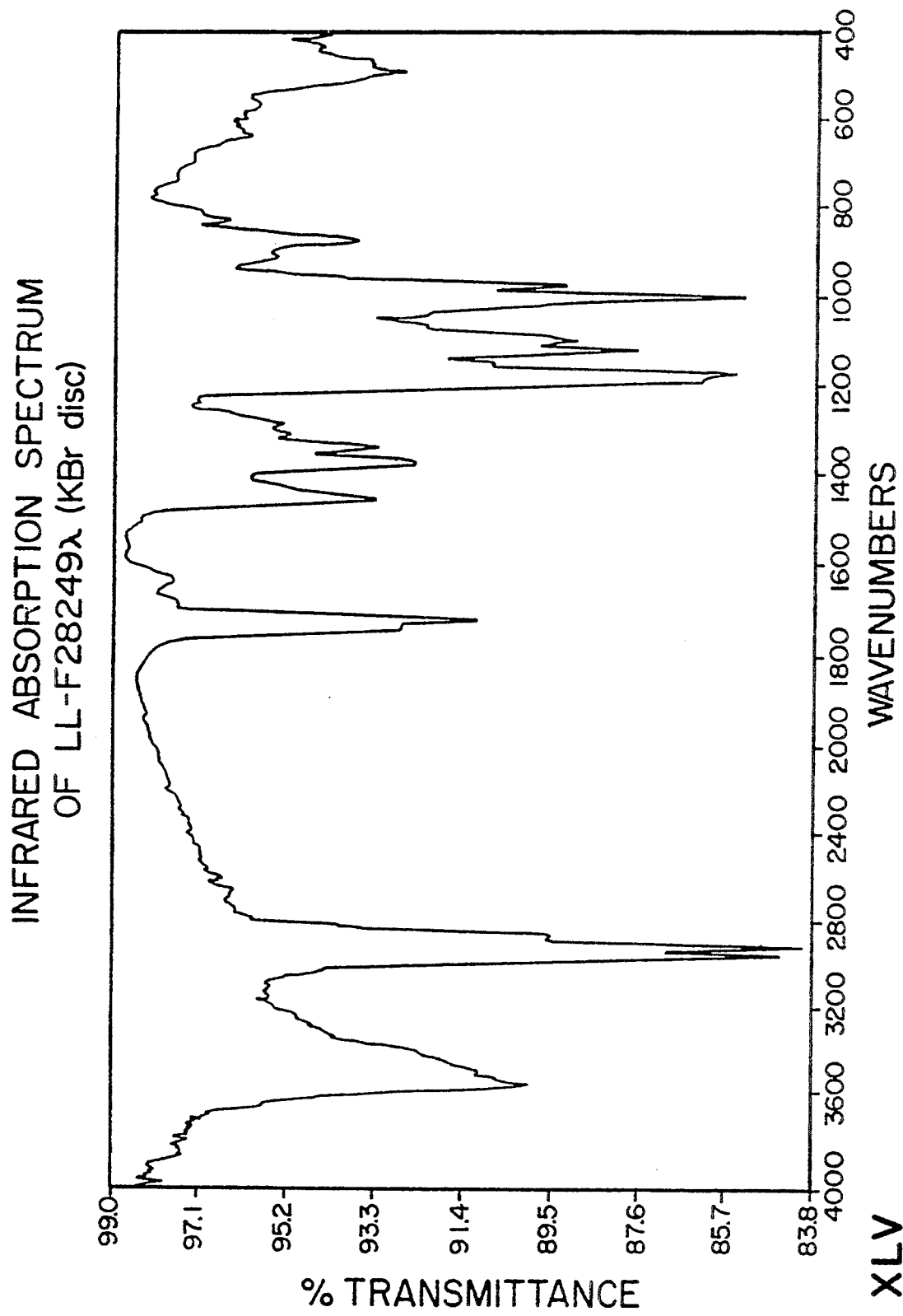

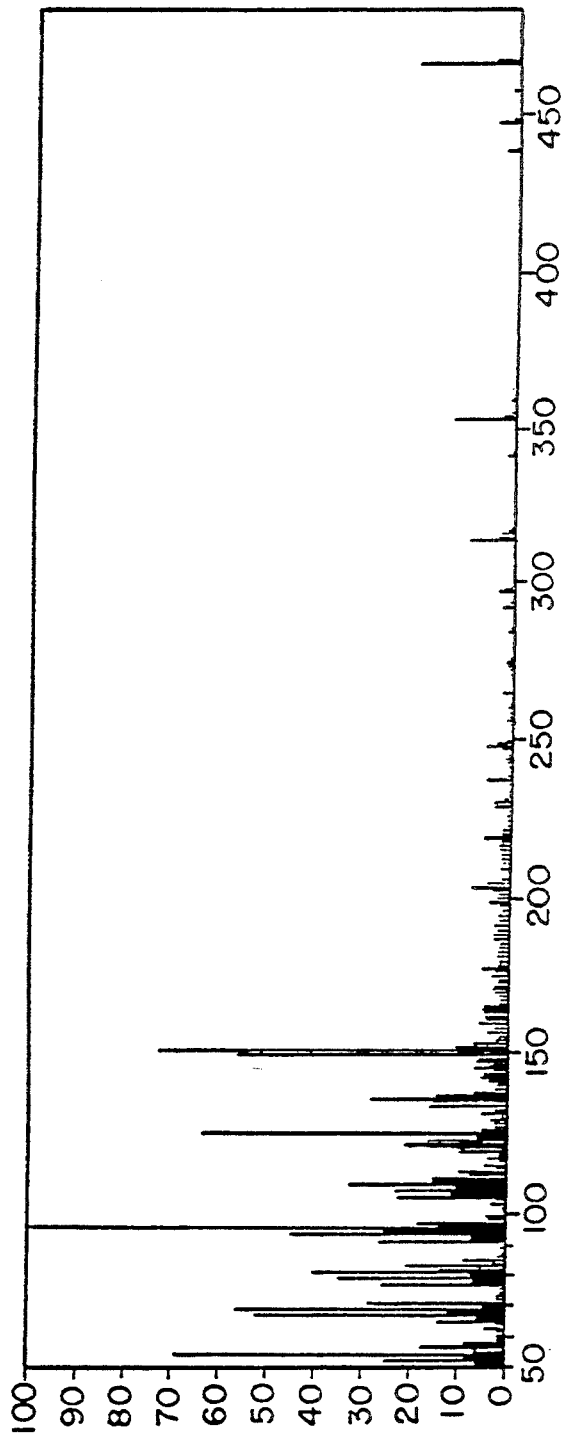
FIG. XLVI

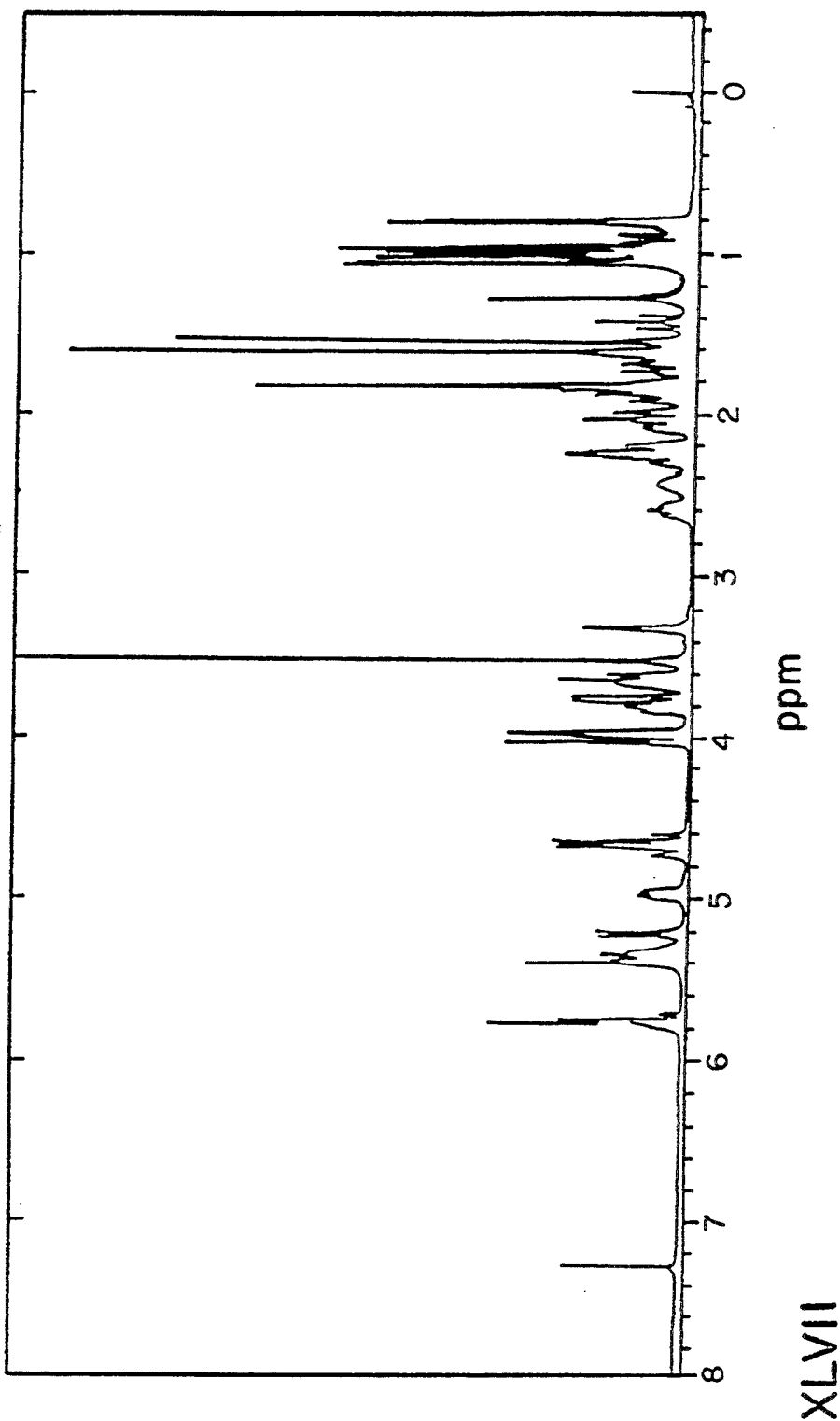
FIG. XLVII

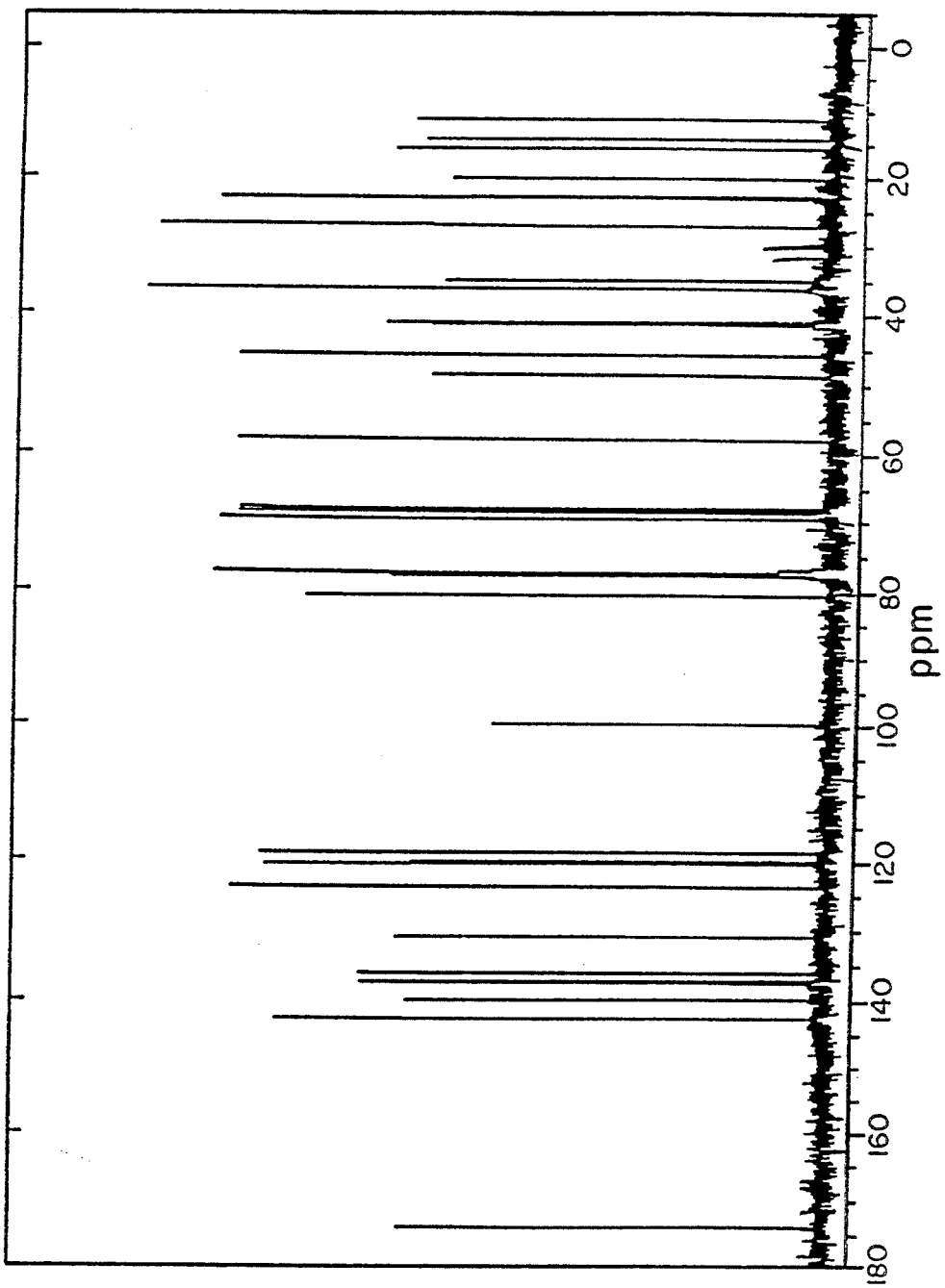
FIG. XLVIII

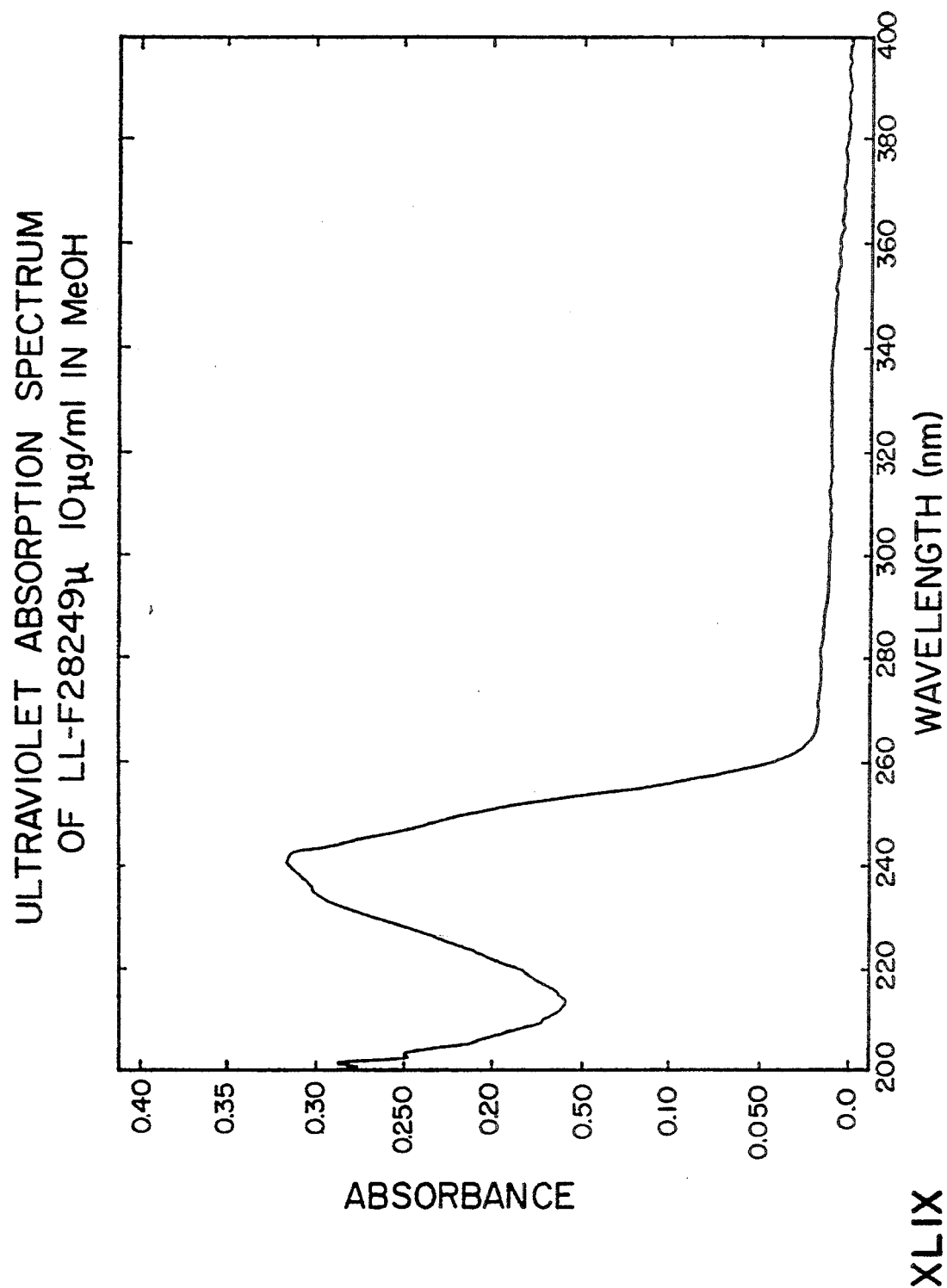
FIG. XLIX

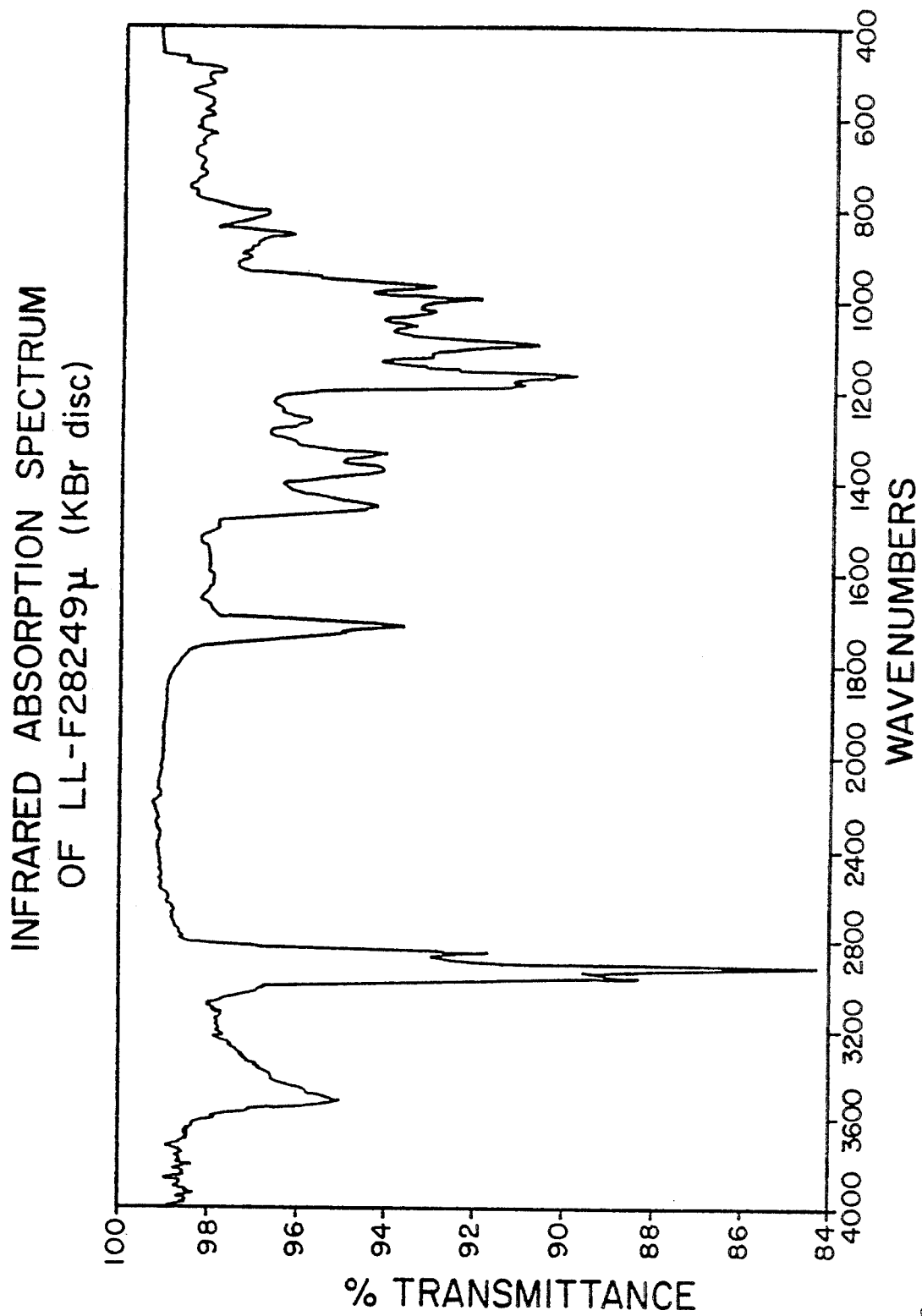

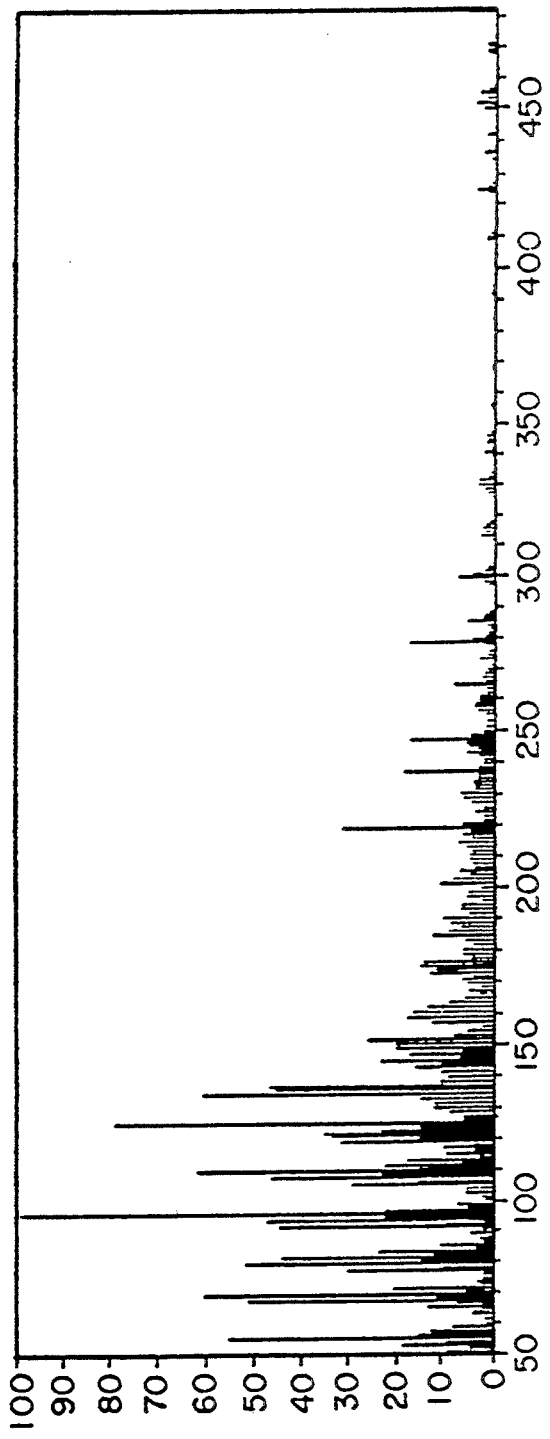
FIG. LI

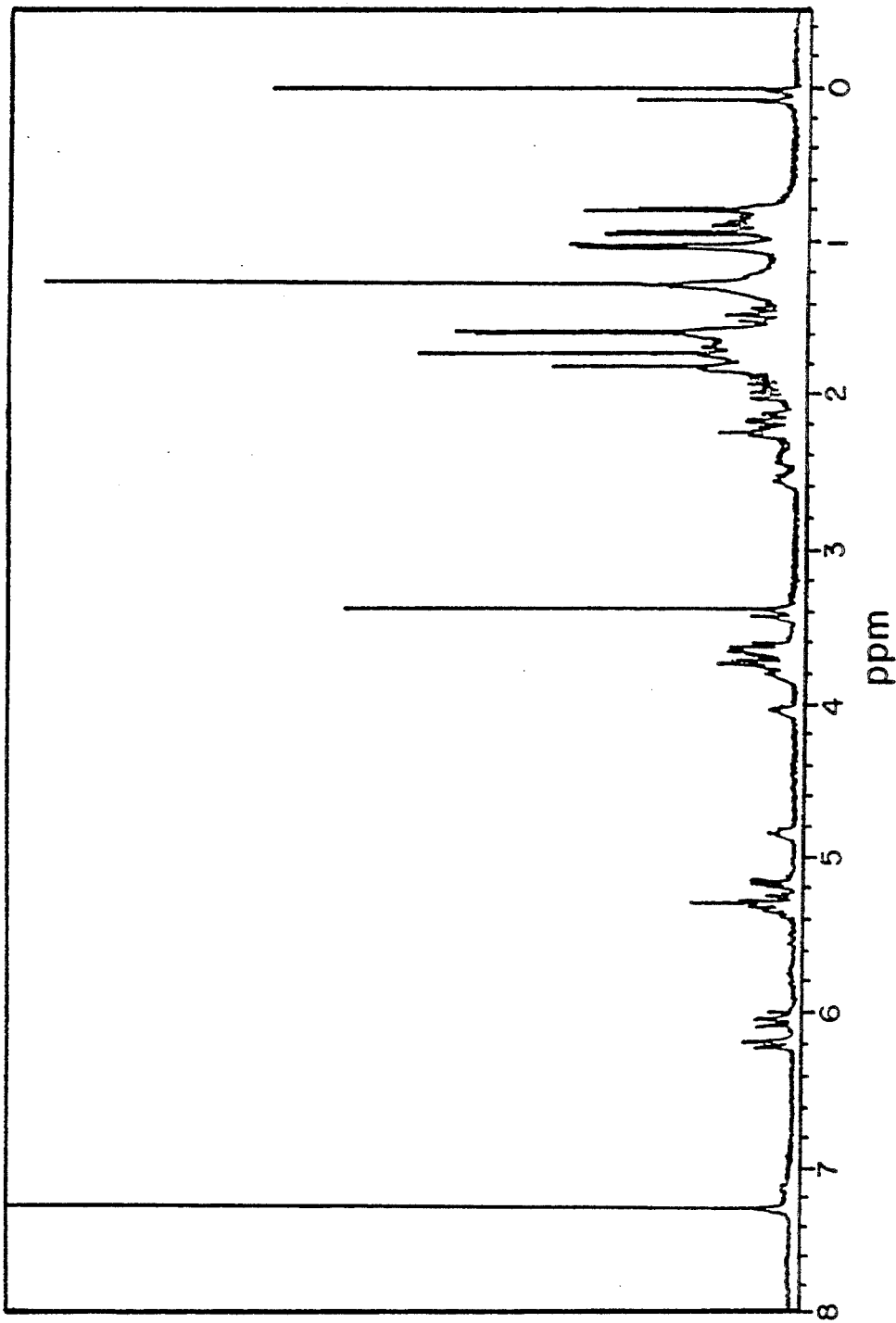
FIG. LII

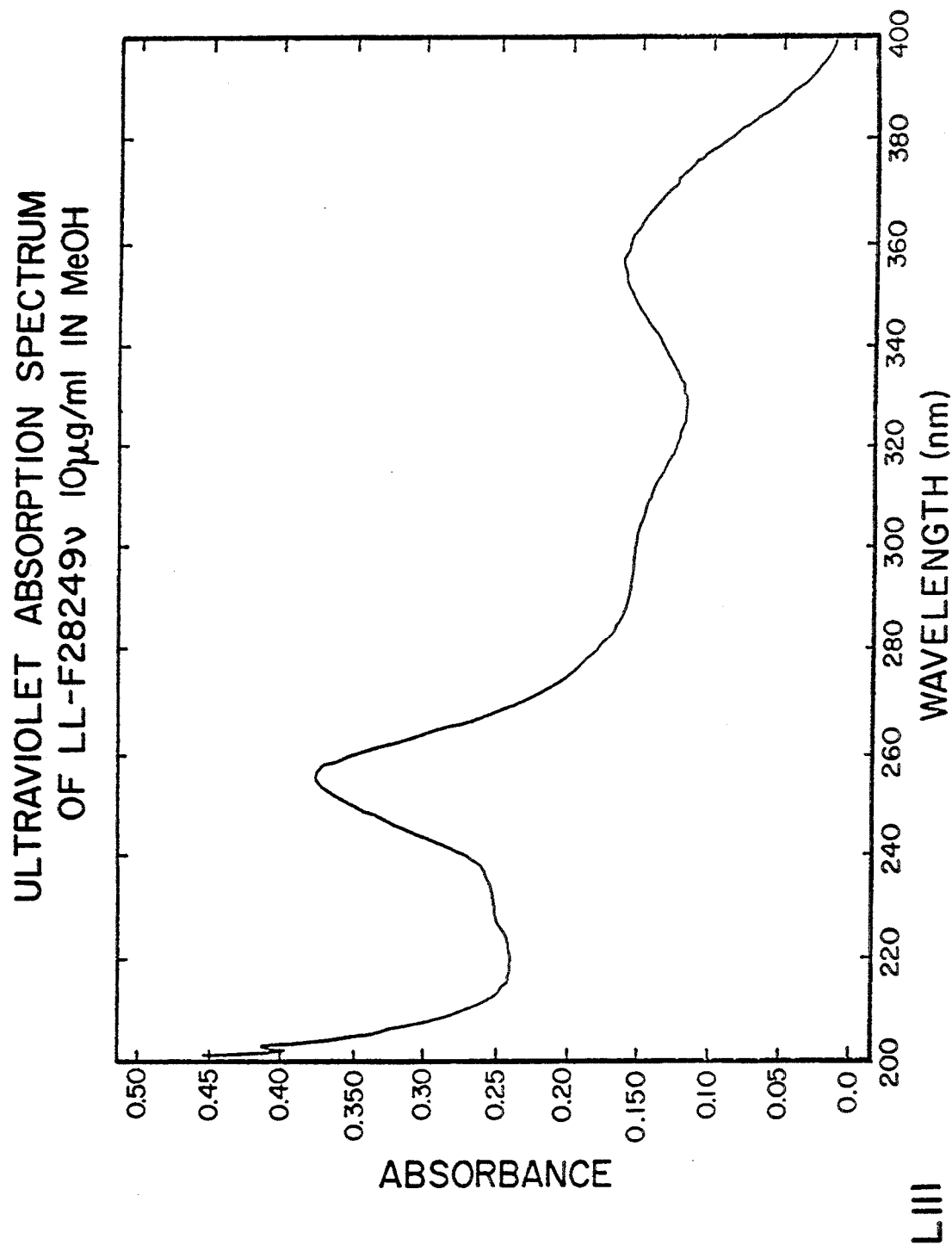
FIG. LIII

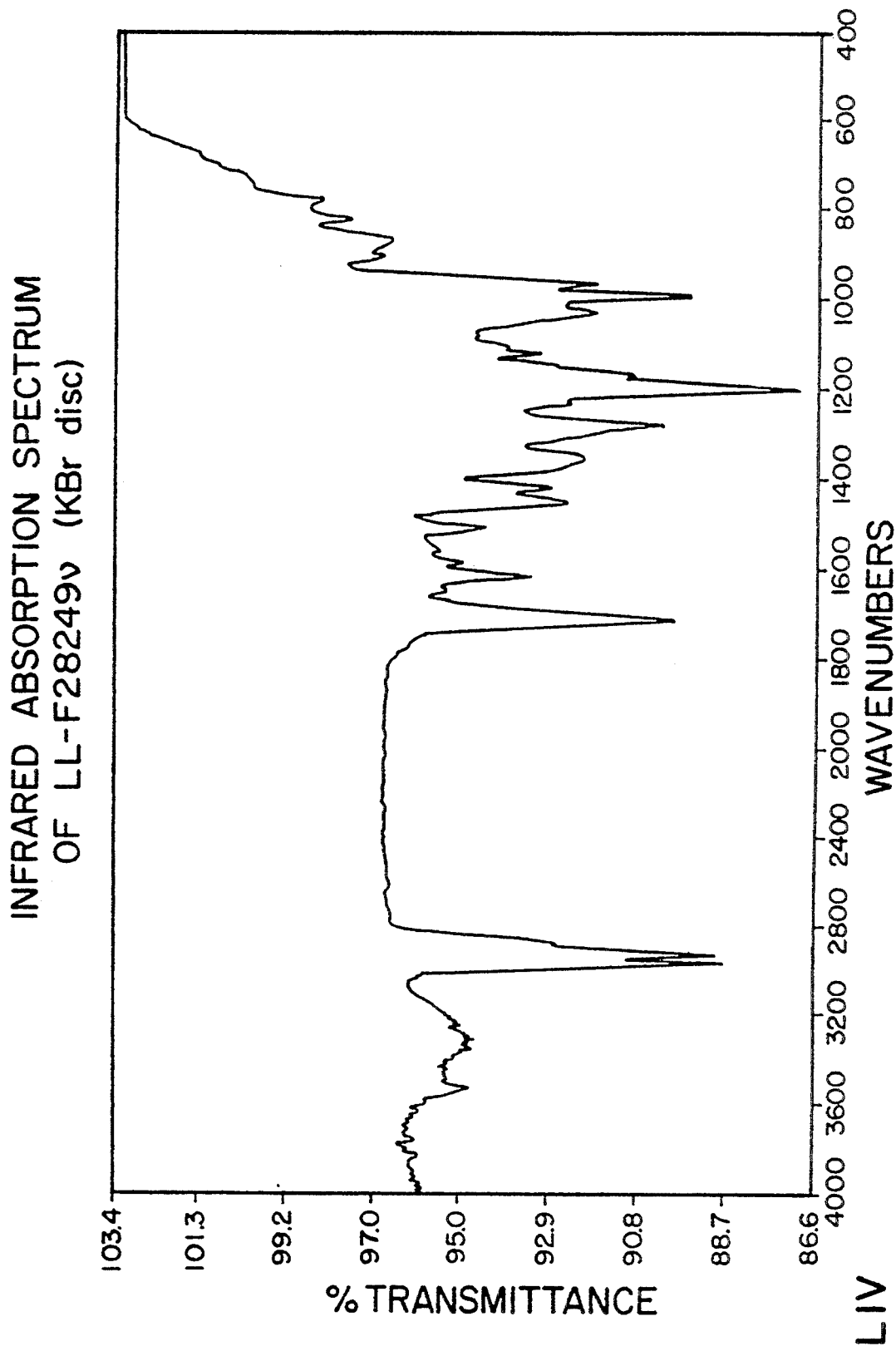

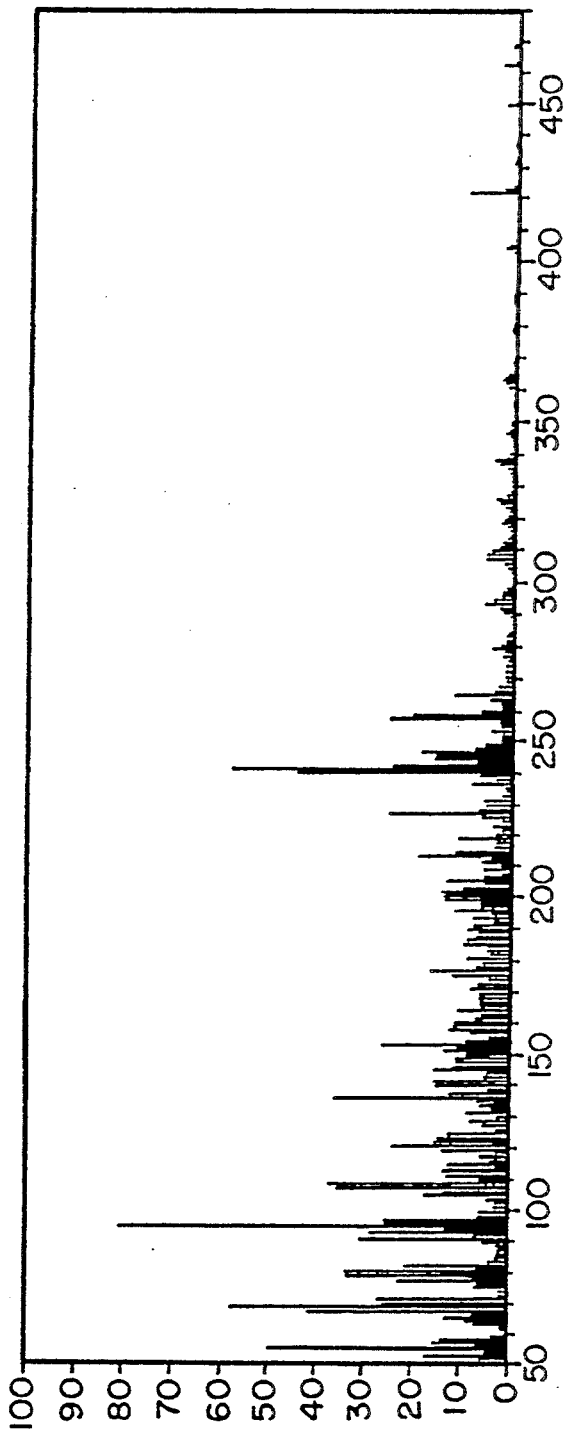
FIG. LV

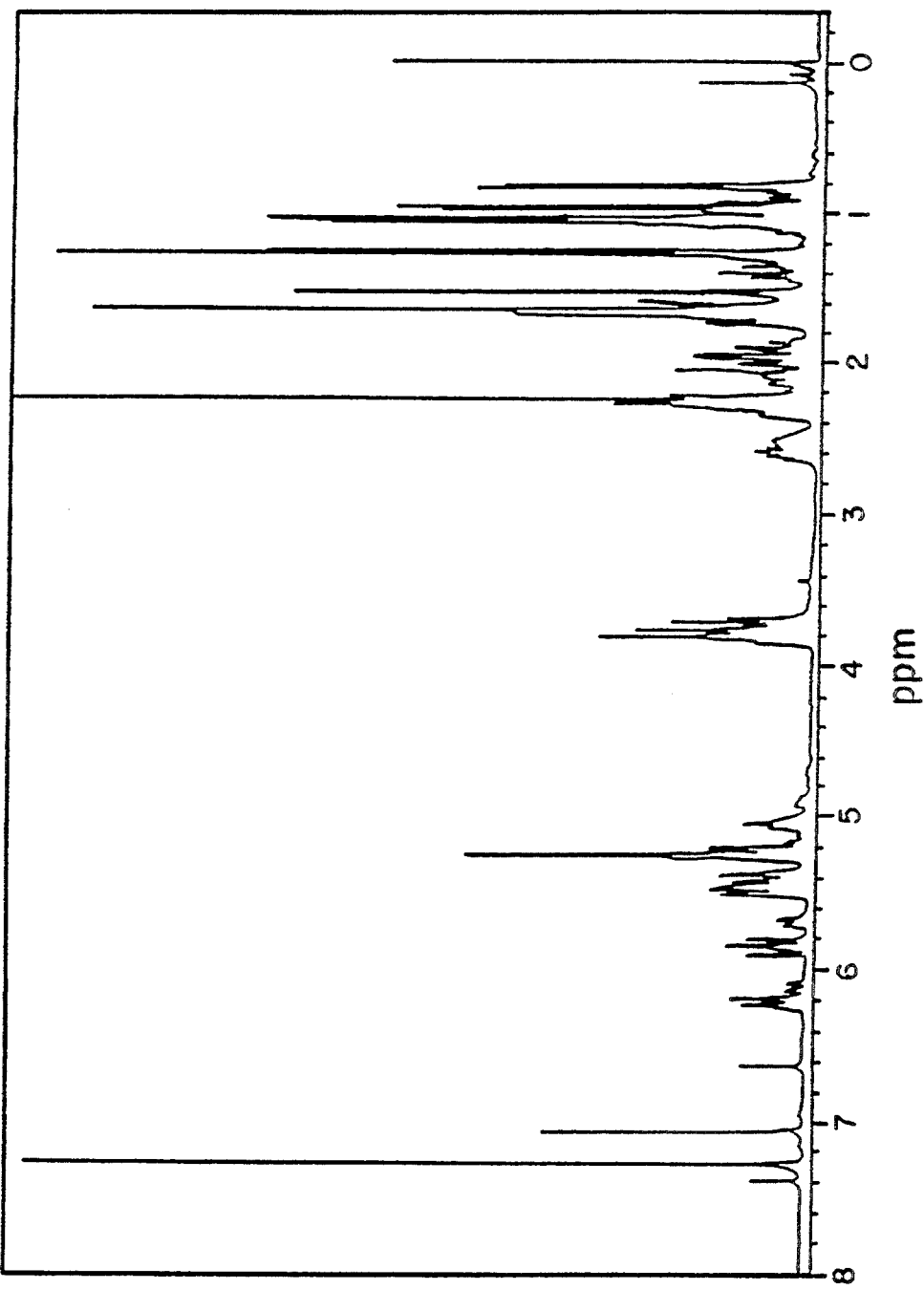
FIG. LVI

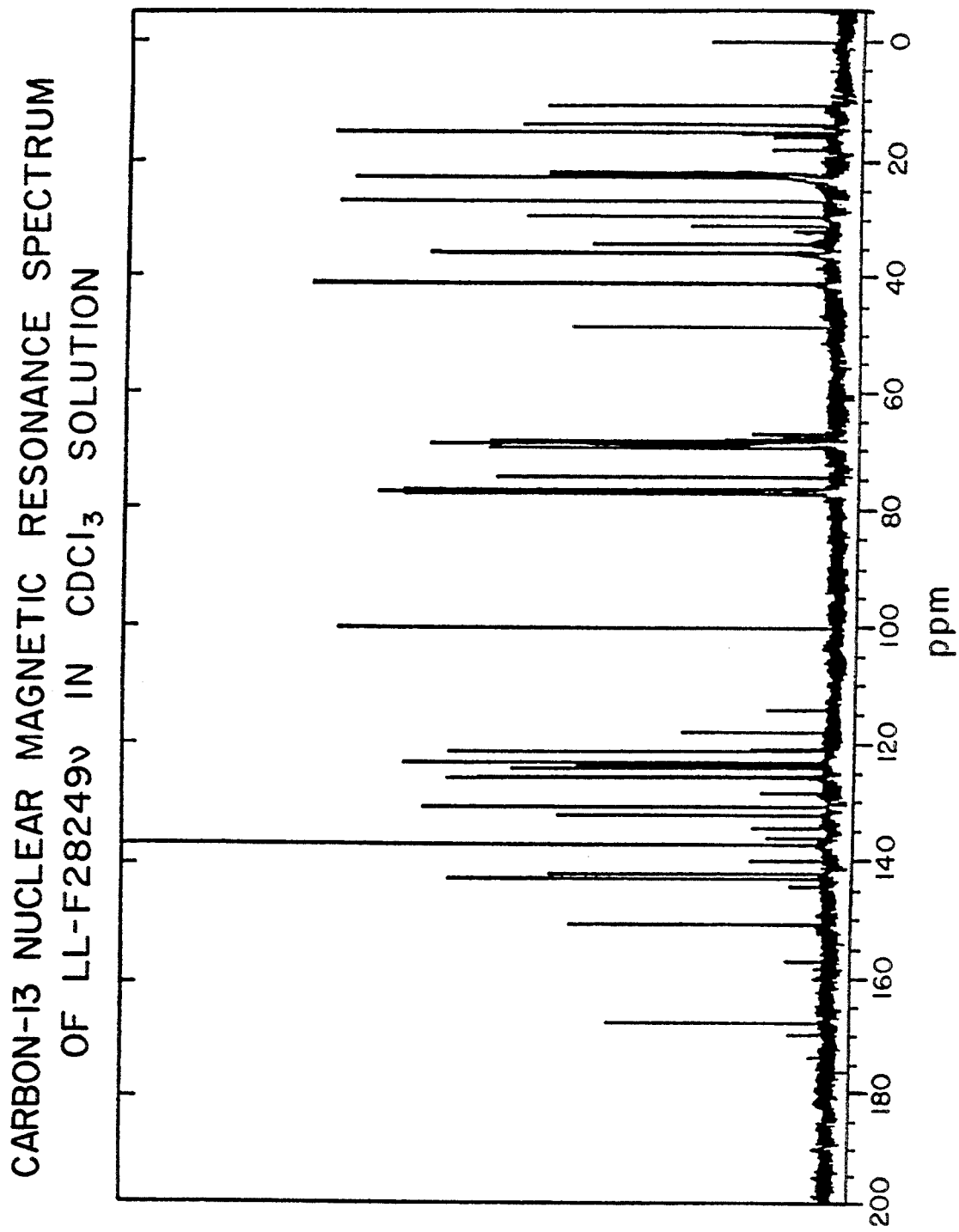
FIG. LVII
CARBON-13 NUCLEAR MAGNETIC RESONANCE SPECTRUM OF LL-F28249ν IN CDCl₃ SOLUTION ND COMPOSITIONS FOR
HELMINTIC, ARTHROPOD ECTOPARASITIC
AND ACARIDAL INFECTIONS WITH NOVEL
AGENTS This application is a division of application Ser. No. 07/712,777, filed on Jun. 10, 1991, now U.S. Pat. No. 5,317,030, which is a continuation of application Ser. No. 06/732,251, filed on May 10, 1985, now U.S. Pat. No. 5,198,464, which, in turn, is a continuation-in-part of application Ser. No. 06/617,649, filed on Jun. 5, 1984, now U.S. Pat. No. 4,869,901.

BACKGROUND OF THE INVENTION

The present invention relates to methods and compositions for preventing, treating or controlling helmintic, arthropod ectoparasitic and acaridal infections in warm-blooded animals by administering thereto an effective amount of the agents (compounds) designated LL-F28249α, β, γ, δ, ε, ξ, η, θ, ι, κ, λ, μ, ν and ω, or mixtures thereof, such as the fermentation broth, or whole mash or the pharmaceutically and pharmacologically-acceptable salts thereof. Plant nematodes also are effectively controlled by use of these agents, mixtures and/or salts. Further, these agents are effective as insecticidal agents, as well.

The diseases described above cause not only devastating effects but also serious economic problems and losses for farmers raising meat-producing animals such as swine, sheep, cattle, goats, rabbits, and poultry. Further, such diseases are a source of great concern for companion animals such as horses, dogs and cats. Although these diseases have been recognized for many years and drugs exist for the treatment and/or prevention of such diseases, the present invention utilizes an entirely new set of active agents, isolated from a previously unknown microorganism, for the prevention, treatment or control of those diseases.

For instance, U.S. Pat. No. 3,950,360, Aoki et al, Apr. 13, 1976, discloses certain antibiotic substances obtained by culturing a Streptomyces microorganism, said compounds being useful as insecticides and acaracides. But as seen from the characteristics identifying such microorganism, the present microorganism is distinct, and its active components are derived from totally different microorganisms. Further, an entire series of U.S. patents relates to certain compounds produced by the fermentation of *Streptomyces avermitilis*, a distinct organism from the present one (U.S. Pat. No. 4,171,314, Chabala et al, Oct. 16, 1979; U.S. Pat. No. 4,199,569, Chabala et al, Apr. 22, 1980; U.S. Pat. No. 4,206,205, Mrozik et al, Jun. 3, 1980; U.S. Pat. No. 4,310,519, Albers-Schonberg, Jan. 12, 1982; U.S. Pat. No. 4,333,925, Buhs et al, Jun. 8, 1982). U.S. Pat. No. 4,423,209, Mrozik, Dec. 27, 1983 relates to the process of converting some of these less desirable components to more preferred ones. However, the present active agents identified as LL-F28249α, β, γ, δ, ε, ξ, η, θ, ι, κ, λ, μ, ν and ω, are derived from the fermentation of a newly discovered and previously uncultivated microorganism. Also, the present compounds and/or the fermentation broth or whole mash of microorganism *Streptomyces cyaneogriseus* ssp. *noncyanogenus* NRRL 15773, plus the pharmaceutically and pharmacologically-acceptable salts thereof (collectively referred to as active ingredient), exhibit excellent and effective treatments and/or prevention of these serious diseases of warm-blooded animals.

The full name of the microorganism LL-F28249, NRRL No. 15773, in terms of genus, species, and subspecies is *Streptomyces cyaneogriseus noncyanogenus*; however, for brevity it is referred to as above written throughout the specification and claims.

The strain is assigned to the genus Streptomyces based upon morphology and cell chemistry (content of the L isomer of diaminopimelic acid). The strain's morphology and physiological data place it close to *S. cyaneogriseus*, as represented by ISP 5534 (ATCC 27426). Then, comparisons of the formation of gray aerial mycelium soluble pigments on media (Table A) and coiled chains of smooth conidia (3–25 spores per chain) were made. The present strain is negative for blue soluble pigment wherein the comparison strain, ISR 5534, is positive. The strains have similar reactions in the ISP carbohydrate utilization tests indicating positive for arabinose, fructose, glucose, rhamnose and xylose, while indicating negative for inositol, mannitol, raffinose and sucrose (ISP 5534 slightly positive). However, the strains differ in several characters (Table B) out of 53 in the Gordon tests. These differences support the creation of a subspecies of *S. cyaneogenseus* for the present microorganism.

SUMMARY OF THE INVENTION

It is, therefore, an object of this invention to provide a novel method for the control of helmintic, arthropod ectoparasitic and acaridal infections in warm-blooded animals, particularly meat-producing animals, such as poultry, cattle, sheep, swine, rabbits, and companion animals such as horses, dogs and cats.

It is also an object of the present invention to provide novel compositions effective for the control of said diseases in warm-blooded animals.

It is a further object of the present invention to provide a novel method and compositions for the control of insect pests. These and further objects will become more apparent by the description of the invention.

It has been discovered that the agents useful in the methods and compositions of the present invention are produced by the fermentation of a nutrient medium containing the strain of microorganism, Streptomyces

TABLE A

Comparison of F 28249 and ISP 5534 on ISP Morphology Test Media (Numbers are from NBS-ISCC)

| Medium | | F 28249 | ISP 5534 |
|---|---|---|---|
| Yeast-Malt (ISP 2) | A.m.[1] | Medium gray (265) | Light to medium gray (264–265) |
| | V.m. | Light tannish (75) Deep yellow-brown | Light tannish-white to blackish-blue (188) |
| | S.p. | Light brown | Light brown |
| Inorganic salts starch | A.m. | Light olive-gray (112 to medium gray (265 | Medium gray (265) |
| | V.m. | Deep gray to black (266–267) | Gray-purplish-blue (204) |
| | S.p. | Grayish-yellowish-brown | None |
| Glycerol-Asparagine (ISP 5) | A.m. | 263 (white) to yellowish-gray (93) | 263 (white) to light gray (264) |
| | V.m. | Black (267) to light olive brown (96) | Gray-purplish-blue (203–204) |
| | S.p. | Slight brownish | Light yellowish-gray |
| Oatmeal (ISP 3) | A.m. | Yellow-gray (93) | None |
| | V.m. | Colorless | Colorless |

TABLE A-continued

Comparison of F 28249 and ISP 5334 on ISP Morphology Test Media (Numbers are from NBS-ISCC)

| Medium | F 28249 | ISP 5334 |
|---|---|---|
| S.p. | Slight yellowish | None |

1 = A.m., aerial mycelium;
V.m. = vegetative mycelium;
S.p. = Soluble pigment

TABLE B

Comparison of Lederle F 28249 with ISP 5534 (Gordon Tests)

| | F28249 | ISP 5534 |
|---|---|---|
| Growth on/at | | |
| Salicin | + | − |
| 10° | − | + |
| 45° | + | − |
| Production of Urease | + | − |
| Decarboxylation of Mucate | − | + |
| Acid Production | | |
| Raffinose | − | + |
| Sucrose | − | + |

Both strains have the following reactions:
Positive
Hydrolysis of casein, hypoxanthine, xanthine, tyrosine, adrenine, potato starch, gelatin, and esculin;
Production of phosphatase
Sensitivity to lysozyme
Decarboxylation of acetate, citrate, lactate, malate, oxalate and propionate
Acid production from arabinose, cellobiose, dextrin, fructose, galactose, glucose, glycerol, lactose, maltose, mannose, α-methyl D-glucoside, rhamnose, salicin, trehalose.
Negative
Production of nitrate reductase
Decarboxylation of benzoate and tartrate
Acid from adanitol, dulcitol, erythritol, inositol, mannitol, sorbitol, β-methyl-D-xyloside.
Growth on 5% NaCl cyaneogriseus noncyanogenus, NRRL 15773. These agents include not only the fermentation broth and whole mash of said microorganism but also include the agents, LL-F29249α, LL-F29249β, LL-F29249γ, LL-F29249δ, LL-F29249ε, LL-F29249ξ, LL-F29249η, LL-F29249θ, LL-F29249ι, LL-F29249κ, LL-F29249λ, LL-F29249μ, LL-F29249υ, and LL-F29249ω. These agents and methods for the preparation thereof are described in U.S. patent application of Guy Thomas Carter, Margaret Jennings Torrey and Michael Greenstein, Ser. No. 617,650, filed Jun. 5, 1984, now abandoned, and incorporated herein by reference thereto and U.S. patent continuation-in-part application of Guy Thomas Carter, Margaret Jennings Tarrey and Michael Greenstein, Ser. No. 732,252, filed concurrently herewith and incorporated herein by reference thereto.

The structure and stereochemistry of LL-F28249 have not ben fully defined, but the proposed structures are shown below. Component LL-F28249ω, is related to Hondamycin (Albimycin) which is disclosed in The Journal of Antibiotics, 22, No. 11, 521–526 (1969).

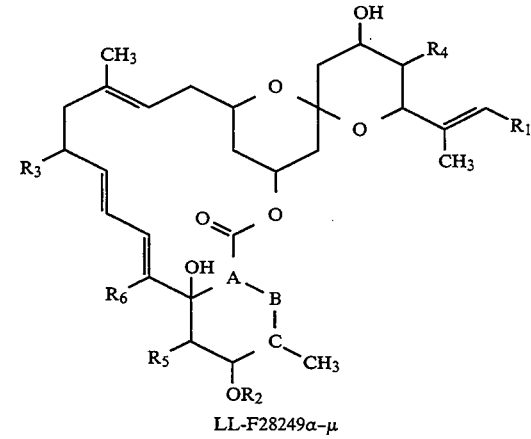

LL-F28249α-μ

| Component | $R_1$ | $R_2$ | $R_3$ | $R_4$ | $R_5$ | $R_6$ | $R_5 + R_6$ | A—B | B—C |
|---|---|---|---|---|---|---|---|---|---|
| LL-F28249α | CH(CH$_3$)$_2$ | H | CH$_3$ | CH$_3$ | | | —O—CH$_2$— | CH—CH | CH=C |
| LL-F28249β | CH$_3$ | H | CH$_3$ | CH$_3$ | | | —O—CH$_2$— | CH—CH | CH=C |
| LL-F28249γ | CH$_3$ | CH$_3$ | CH$_3$ | CH$_3$ | | | —O—CH$_2$— | CH—CH | CH=C |
| LL-F28249δ | CH$_3$ | CH$_3$ | CH$_3$ | CH$_3$ | OH | CH$_2$OH | | CH—CH | CH=C |
| LL-F28249ε | CH(CH$_3$)$_2$ | H | H | CH$_3$ | | | —O—CH$_2$— | CH—CH | CH=C |
| LL-F28249ξ | CH$_2$CH$_3$ | H | CH$_3$ | CH$_3$ | | | —O—CH$_2$— | CH—CH | CH=C |
| LL-F28249η | CH(CH$_3$)$_2$ | H | CH$_3$ | CH$_3$ | | | —O—CH$_2$— | C=CH | CH—CH |
| LL-F28249θ | CH(CH$_3$)$_2$ | H | CH$_3$ | CH$_2$CH$_3$ | | | —O—CH$_2$— | CH—CH | CH=C |
| LL-F28249ι | CH(CH$_3$)$_2$ | H | CH$_2$CH$_3$ | CH$_3$ | | | —O—CH$_2$— | CH—CH | CH=C |
| LL-F28249κ | CH$_3$ | CH$_3$ | CH$_3$ | CH$_3$ | H | CH$_3$ | | CH—CH | CH=C |
| LL-F28249λ | CH(CH$_3$)$_2$ | CH$_3$ | CH$_3$ | CH$_3$ | | | —O—CH$_2$— | CH—CH | CH=C |
| LL-F28249μ | CH(CH$_3$)$_2$ | CH$_3$ | CH$_3$ | CH$_3$ | H | CH$_3$ | | CH—CH | CH=C |

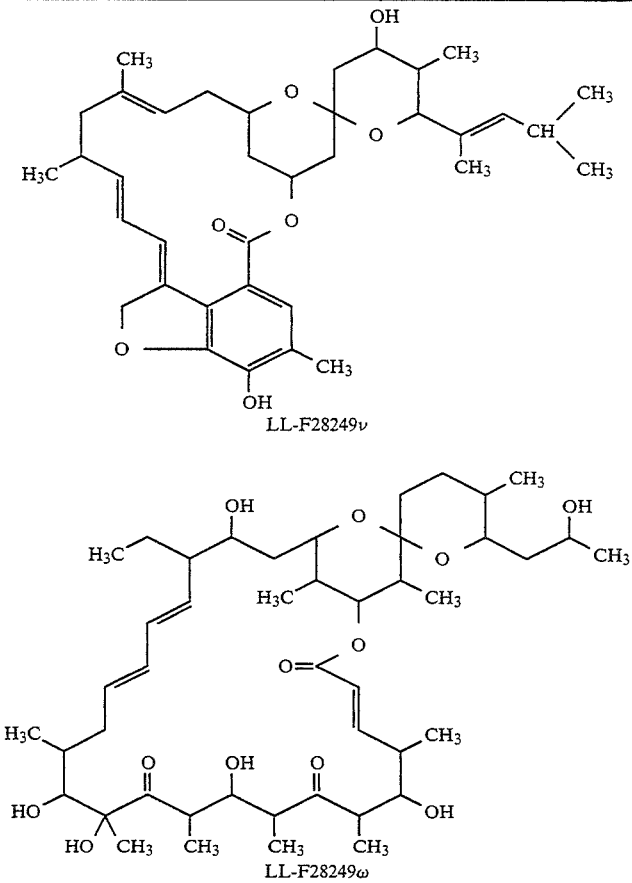

LL-F28249ν

LL-F28249ω

DESCRIPTION OF THE DRAWINGS

FIG. I: Characteristic ultraviolet absorption spectrum of compound designated LL-F28249α, NRRL 15773.

FIG. II: Characteristic infrared absorption spectrum of compound designated LL-F28249α, NRRL 15773.

Figure 1:
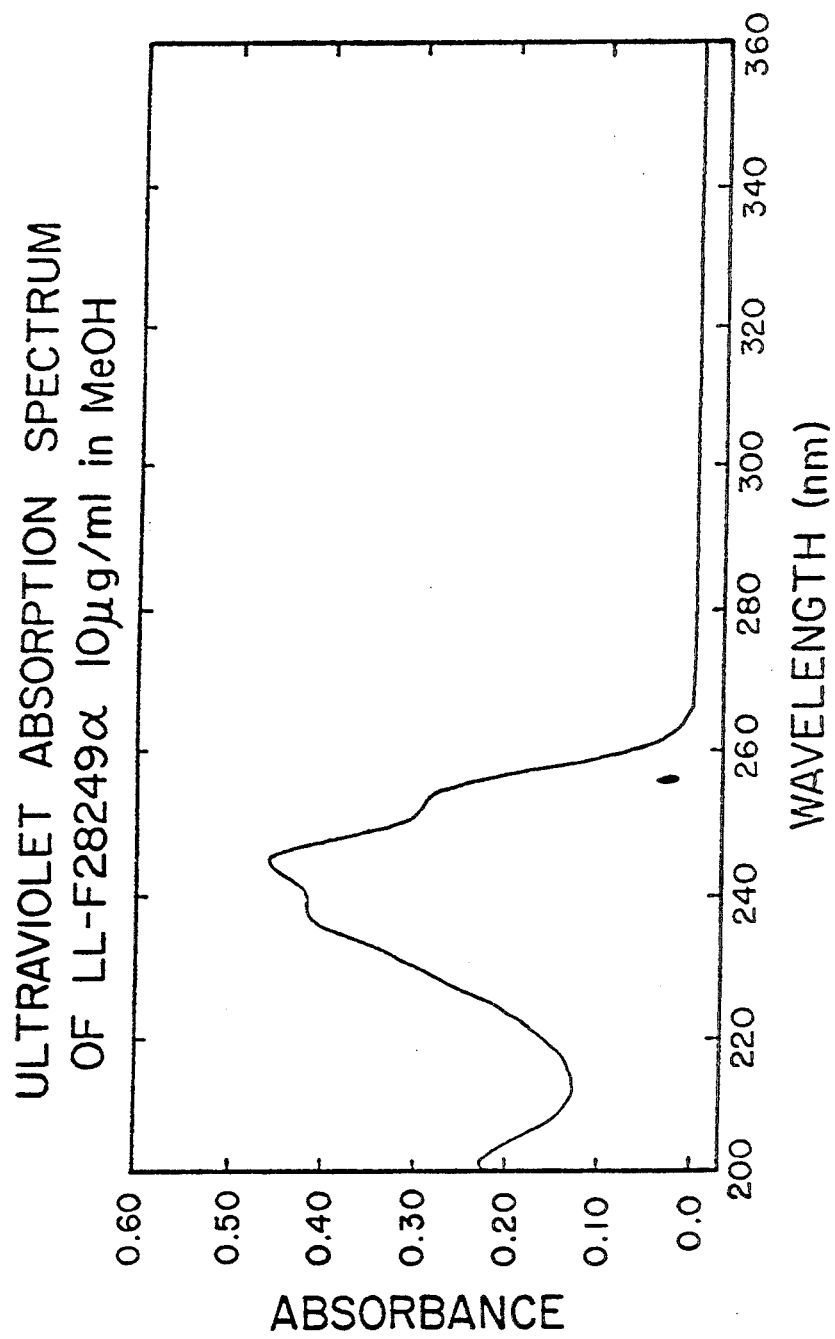

FIG. III: Characteristic proton nuclear magnetic resonance spectrum of compound designated LL-F28249α, NRRL 15773, in CDCl₃ solution.

FIG. IV: Characteristic carbon-13 nuclear magnetic resonance spectrum of compound designated LL-F28249α, NRRL 15773, in CDCl₃ solution.

FIG. V: Characteristic electron impact mass spectrum of compound designated LL-F28249α, NRRL 15773.

FIG. VI: Characteristic ultraviolet absorption spectrum of compound designated LL-F28249β, NRRL 15773.

FIG. VII: Characteristic infrared absorption spectrum of compound designated LL-F28249β, NRRL 15773.

FIG. VIII: Characteristic proton nuclear magnetic resonance spectrum of compound designated LL-F28249β, NRRL 15773, in CDCl₃.

FIG. IX: Characteristic electron impact mass spectrum of compound designated LL-F28249β, NRRL 15773.

FIG. X: Characteristic ultraviolet absorption spectrum of compound designated LL-F28249γ, NRRL 15773.

FIG. XI: Characteristic infrared absorption spectrum of compound LL-F28249γ, NRRL 15773.

FIG. XII: Characteristic proton nuclear magnetic resonance spectrum of compound LL-F28249γ, NRRL 15773, in CDCl₃.

FIG. XIII: Characteristic carbon-13 nuclear magnetic resonance spectrum of compound designated LL-F28249γ, NRRL 15773, in CDCl₃.

FIG. XIV: Characteristic electron impact mass spectrum of compound designated LL-F28249γ, NRRL 15773.

FIG. XV: Characteristic ultraviolet absorption spectrum of compound designated LL-F28249ω, NRRL 15773.

FIG. XVI: Characteristic infrared absorption spectrum of compound designated LL-F28249ω, NRRL 15773.

FIG. XVII: Characteristic proton nuclear magnetic resonance spectrum of compound designated LL-F28249ω, NRRL 15773, in CDCl₃.

FIG. XVIII: Characteristic nuclear magnetic resonance spectrum of compound designated LL-F28249ω, NRRL 15773, in CDCl₃.

FIG. XIX: Characteristic electron impact mass spectrum of compound designated LL-F28249ω, NRRL 15773.

FIG. XX: Characteristic ultraviolet absorption spectrum of compound designated LL-F28249δ, NRRL 15773.

FIG. XXI: Characteristic proton nuclear magnetic resonance spectrum of compound designated LL-F28249δ, NRRL 15773, in CDCl₃.

FIG. XXII: Characteristic electron inpact mass spectrum of compound designated LL-F28249δ, NRRL 15773.

FIG. XXIII: Characteristic ultraviolet absorption spectrum of compound designated LL-F28249ε, NRRL 15773.

FIG. XXIV: Characteristic proton nuclear magnetic resonance spectrum of compound designated LL-F28249ε, NRRL 15773, in CDCl$_3$.

FIG. XXV: Characteristic electron impact mass spectrum of compound designated LL-F28249ε, NRRL 15773.

FIG. XXVI: Characteristic ultraviolet absorption spectrum of compound designated LL-F28249ζ, NRRL 15773.

FIG. XXVII: Characteristic proton nuclear magnetic resonance spectrum of compound designated LL-F28249ζ, NRRL 15773, in CDCl$_3$.

FIG. XXVIII: Characteristic electron impact mass spectrum of compound designated LL-F28249ζ, NRRL 15773.

FIG. XXIX: Characteristic ultraviolet absorption spectrum of compound designated LL-F28249η, NRRL 15773.

FIG. XXX: Characteristic proton nuclear magnetic resonance spectrum of compound designated LL-F28249η, NRRL 15773, in CDCl$_3$.

FIG. XXXI: Characteristic electron impact mass spectrum of compound designated LL-F2824η, NRRL 15773.

FIG. XXXII: Characteristic ultraviolet absorption spectrum of compound designated LL-F28249θ, NRRL 15773.

FIG. XXXIII: Characteristic proton nuclear magnetic resonance spectrum of compound designated LL-F2824900, NRRL 15773, in CDCl$_3$.

FIG. XXXIV: Characteristic electron impact mass spectrum of compound designated LL-F28249θ, NRRL 15773.

FIG. XXXV: Characteristic ultraviolet absorption spectrum of compound designated LL-F28249ι, NRRL 15773.

FIG. XXXVI: Characteristic proton nuclear magnetic resonance spectrum of compound designated LL-F28249ι, NRRL 15773, in CDCl$_3$.

FIG. XXXVII: Characteristic electron impact mass spectrum of compound designated LL-F28249ι, NRRL 15773.

FIG. XXXVIII: Characteristic carbon—13 nuclear magnetic resonance spectrum of compound designated LL-F28249β, NRRL 15773, in CDCl$_3$ solution.

FIG. XXXIX: Characteristic ultraviolet absorption spectrum of compound designated LL-F28249κ, NRRL 15773.

FIG. XL: Characteristic infrared absorption spectrum of compound designated LL-F28249κ, NRRL 15773.

FIG. XLI: Characteristic electron impact mass spectrum of compound designated LL-F28249κ, NRRL 15773.

FIG. XLII: Characteristic proton nuclear magnetic resonance spectrum of compound designated LL-F28249κ, NRRL 15773.

FIG. XLIII: Characteristic carbon—13 nuclear magnetic resonance spectrum of compound designated LL-F28249κ, NRRL 15773.

FIG. XLIV: Characteristic ultraviolet absorption spectrum of compound designated LL-F28249λ, NRRL 15773.

FIG. XLV: Characteristic infrared absorption spectrum of compound designated LL-F28249λ, NRRL 15773.

FIG. XLVI: Characteristic electron impact mass spectrum of compound designated LL-F28249λ, NRRL 15773.

FIG. XLVII: Characteristic proton nuclear magnetic resonance spectrum of compound designated LL-F28249λ, NRRL 15773.

FIG. XLVIII: Characteristic carbon—13 nuclear magnetic resonance spectrum of compound designated LL-F28249λ, NRRL 15773.

FIG. XLVIX: Characteristic ultraviolet absorption spectrum of compound designated LL-F28249μ, NRRL 15773.

FIG. L: Characteristic infrared absorption spectrum of compound designated LL-F28249μ, NRRL 15773.

FIG. LI: Characteristic electron impact mass spectrum of compound designated LL-F28249μ, NRRL 15773.

FIG. LII: Characteristic proton nuclear magnetic resonance spectrum of compound designated LL-F2824μ, NRRL 15773.

FIG. LIII: Characteristic ultraviolet absorption spectrum of compound designated LL-F28249ν, NRRL 15773.

FIG. LIV: Characteristic infrared absorption spectrum of compound designated LL-F28249ν, NRRL 15773.

FIG. LV: Characteristic electron impact mass spectrum of compound designated LL-F28249ν, NRRL 15773.

FIG. LVI: Characteristic proton nuclear magnetic resonance spectrum of compound designated LL-F28249ν, NRRL 15773.

FIG. LVII: Characteristic carbon—13 nuclear magnetic resonance spectrum of compound designated LL-F28249ν, NRRL 15773.

DETAILED DESCRIPTION OF THE INVENTION

It has been discovered that the above-mentioned agents, as well as the fermentation broth and whole mash of said microorganism, are especially effective for controlling helmintic, arthropod ectoparasitic and acaridal infections in meat-producing animals such as cattle, sheep, swine, rabbits, poultry, such as chickens, turkeys, ducks, geese, quail, and pheasants and companion animals.

In practice, the present invention involves the method of preventing, controlling or treating said infections, in warm-blooded animals by administering orally, parenterally, or topically thereto, a prophylactically, pharmaceutically or therapeutically-effective amount of the fermentation broth or whole mash of microorganism *Streptomyces cyaneogriseus noncyanogenus*, NRRL 15773, the fermentation broth or whole mash of said microorganism containing compounds designated LL-F28249α, β, γ, δ, ε, ζ, η, θ, ι, κ, λ, μ, ν and ω, compounds designated as LL-F28249α, LL-F28249β, LL-F28249γ, LL-F28249δ, LL-F28249ε, LL-F28249ζ, LL-F28249η, LL-F28249θ, LL-F28249ι, LL-F28249κ, LL-F28249λ, LL-F28249μ, LL-F28249ν, and LL-F28249ω, as identified and characterized herein, or the pharmaceutically and pharmacologically-acceptable salts thereof (collectively referred to as active ingredient).

Although administration of the compound or fermentation broth/whole mash (hereinafter broth or mash) will generally be most practical in or with the feed or in the drinking water, the above-said compounds, broth or mash, or pharmaceutically and pharmacologically-acceptable salts thereof, may also be administered to individual hosts in the form of tablets, drenches, gels, capsules, or the like, or by injection in the form of a paste, gel, pellet, or solution. These latter methods of administration are, of course, less practical for the treatment of large groups of animals, but they are quite practical for use on a small scale or on an individual basis.

When the agents (antibiotics) LL-F28249$\alpha$, $\beta$, $\gamma$, $\delta$, $\epsilon$, $\zeta$, $\eta$, $\theta$, $\iota$, $\kappa$, $\lambda$, $\mu$, $\nu$ or $\omega$ or the fermentation broth or whole mash of *Streptomyces cyaneogriseus noncyanogenus* NRRL 15773 are used as prophylactic or therapeutic treatments of helmintic, arthropod ectoparasitic and acaridal infections, in animals and poultry, generally about 0.05 ppm to 500.0 ppm, and preferably 0.1 ppm to 300 ppm of the agent or broth or mash above-described, administered in the diet or drinking water of the animal, is effective for preventing, controlling, or treating said infections in those animals.

Medicated feeds useful in the method of the present invention are usually prepared by thoroughly admixing about 0.00001% by weight to about 0.01% by weight of the agent (antibiotic) or above-described broth or mash with a nutritionally-balanced feed, as for example, the feed described in the examples hereinafter.

When using the compounds and/or broth or mash of the present invention for the prevention or control of helminths, arthropod ectoparasites and acarides, the active agent is generally first prepared as an animal feed premix. The premix usually contains a relatively high percentage of the active ingredient and is generally blended with the animal's feed just prior to administration. If desired, the feed premix may also be applied as a top dressing for the animal's daily ration.

Feed premixes or concentrates, useful in the practice of the present invention, may be prepared by admixing about 0.1% to 5.0% by weight of the above-identified agents, broth or mash, or pharmaceutically and pharmacologically-acceptable salts thereof, with about 99.9% to 95% by weight of a suitable carrier or diluent.

Carriers suitable for use to make up the feed supplement compositions include the following: alfalfa meal, soybean meal, cottonseed oil meal, linseed oil meal, sodium chloride, calcium carbonate, calcium sulfate, cornmeal, cane molasses, urea, bone meal, corncob meal, rice hull meal, and the like. The carrier promotes an essentially uniform distribution of the active ingredient in the finished feed into which the supplement is blended. It thus performs an important function by ensuring proper distribution of the active ingredient, i.e., about 0.1 ppm to 100 ppm thereof, throughout the feed. This is equivalent to 0.00001% to 0.01%, by weight, of the active ingredient in the finished feed. In practice, usually one or more pounds of premix is added per ton of feed to obtain the desired level of agent (antibiotic) or broth or mash in the finished feed.

If the supplement or premix is used as a top dressing for feed, it likewise helps to ensure uniformity of distribution of the active ingredient across the top of the dressed feed.

Since the compounds of this invention and their pharmaceutically and pharmacologically-acceptable salts are relatively insoluble in water, it is generally desirable, when administering any such compound in the animal's drinking water, to dissolve the active ingredient in an organic solvent such as methanol, ethanol, acetone, DMSO, oleic acid, linoleic acid, propylene glycol, or the like, and admix with the solution a small amount of surfactant and/or dispersing agent to assure solution and/or dispersion of the active ingredient in the animal's drinking water.

Advantageously, where the treatment of a small number of the larger meat-producing animals is required to control parasitic infection therein, the agents LL-F28249$\alpha$, $\beta$, $\gamma$, $\delta$, $\epsilon$, $\zeta$, $\eta$, $\theta$, $\iota$, $\kappa$, $\lambda$, $\mu$, $\nu$ and $\omega$, broth or mash, or pharmaceutically or pharmacologically-acceptable salts thereof may be orally administered, on a daily basis, to the host animal in the form of a medicated gel.

The active ingredients of the invention have also exhibited nematocidal activity against plant nematodes as demonstrated by effectiveness in controlling the free living soil nematode, *C. elegans*. Compositions containing these active ingredients for controlling plant nematodes can be formulated into either liquids or wettable powders. Liquid compositions include about 5% to 20%, w/w, of the active ingredient (active agent, fermentation broth, whole mash or salts) with appropriate amounts of a solvent such as methanol, ethanol, acetone, acetonitrile, and others, and the remainder water. Wettable powders include about 5% to 20%, w/w, of the active ingredient, about 1% to 10% of surfactant, and inert carriers, such as clays, vermiculite, carbon black or the like. About 0.1 to 1.4 kg per hectare is applied to the foilage of plants, the soil in which they are grown or into the trunks thereof.

These agents also are active as topical insecticides, stomach poisons and systemic insecticides and are especially effective for controlling insects of the orders Lepedoptera, Coleoptera, Homoptera, Deptera and Thysanoptera. Plant mites, acarids, additionally are controlled by the agents of the present invention.

These agents generally are applied as dilute, solid or liquid compositions to the breeding ground, food supply or habitat of such insects and/or acarids. The rate of application to such loci include about 0.01 kg/ha to about 8.0 kg/ha, preferably about 0.05 kg/ha to about 0.5 kg/ha.

Surfactants useful in wettable powders of the present invention include those commonly used for formulations of such wettable powders, preferably alkylbenzene sulfonate sodium salts. Bentonite, clay or mixtures thereof are preferred carriers.

Additionally, the active ingredients of the invention also have demonstrated systemic insecticidal activity against *m. ovinus* in sheep.

In practice, generally about 0.02 mg/kg/day to about 3.0 mg/kg/day is effective for controlling parasitic infections in cattle, sheep, and swine and companion animals. For prolonged use, rates as low as 0.002 mg/kg of body weight/day may be employed.

Also in practice, about 0.1 mg per kg to 100 mg per kg is administered to animals infected with helminths.

The physiochemical characteristics for the $\alpha$, $\beta$, $\gamma$, $\delta$, $\epsilon$, $\zeta$, $\eta$, $\theta$, $\iota$, $\kappa$, $\lambda$, $\mu$, $\nu$ and $\omega$ components of LL-F28249 are described below:

DETAILED DESCRIPTION OF THE INVENTION

The physiochemical characteristics for the α, β, γ, δ, ε, ζ, η, θ, κ, λ, μ, ν and ω components of LL-F28249 are described below:

LL-F28249α:
1) Molecular weight: 612 (FAB-MS);
2) Molecular formula: $C_{36}H_{52}O_8$;
3) Specific optical rotation: $[\alpha]_D^{26} = +133 \pm 3°$ (C 0.3, acetone);
4) Ultraviolet absorption spectrum: as shown in FIG. I $UV_{MAX}^{CH3OH} = 244$ nm (ε 28,000);
5) Infrared absorption spectrum: as shown in FIG. II (KBr disc): 3439, 2960, 2925, 1714, 1454, 1374, 1338, 1171, 1120, 996, 967 cm$^{-1}$;
6) Proton nuclear magnetic resonance spectrum (CDCl$_3$): as shown in FIG. III;
7 Carbon-13 nuclear magnetic resonance spectrum (CDCl$_3$): as shown in FIG. IV and described in Table I; and
8) Electron impact mass spectrum: as shown in FIG. V with accurate mass measurements and proposed elemental compositions indicated in Table II.

LL-F28249β:
1) Molecular weight: 584 (FAB-MS);
2) Molecular formula: $C_{34}H_{48}O_8$;
3) Specific optical rotation: $[\alpha]_D^{26} = +125°$ (C 0.30 acetone).
4) Ultraviolet absorption spectrum: as shown in FIG. VI $UV_{MAX}^{CH3OH} = 244$ nm (ε 25,600);
5) Infrared absorption spectrum: as shown in FIG. VII (KBr disc): 3520, 2910, 1735, 1717, 1450, 1375, 1335, 1180, 1170, 1119, 993, 727 cm$^{-1}$;
6) Proton nuclear magnetic resonance spectrum (CDCl$_3$): as shown in FIG. VIII;
7) Carbon-13 nuclear magnetic resonance spectrum (CDCl$_3$): as shown in FIG. XXXVIII and described in Table II A; and
8) Electron impact mass spectrum: as shown in FIG. IX with accurate mass measurements and proposed elemental compositions indicated in Table III.

LL-F28249γ:
1) Molecular weight: 598 (FAB-MS);
2) Molecular formula: $C_{35}H_{50}O_8$;
3) Specific optical rotation: $[\alpha]_D^{26} = +150 \pm 4°$ (C 0.3, acetone);
4) Ultraviolet absorption spectrum: as shown in FIG. X $UV_{MAX}^{CH3OH} = 244$ nm (ε 27,100);
5) Infrared absorption spectrum: as shown in FIG. XI (KBr disc): 3510, 2910, 1735, 1715, 1452, 1375, 1338, 1182, 1172, 1119, 995 cm$^{-1}$;
6) Proton nuclear magnetic resonance spectrum (CDCl$_3$): as shown in FIG. XII;
7) Carbon-13 nuclear magnetic resonance spectrum (CDCl$_3$): as shown in FIG. XIII and described in Table IV; and
8) Electron impact mass spectrum: as shown in FIG. XIV with accurate mass measurements and proposed elemental compositions indicated in Table V.

LL-F28249ω:
1) Molecular weight: 806 (FAB-MS);
2) Molecular formula: $C_{45}H_{74}O_{12}$;
3) Specific optical rotation: $[\alpha]_D^{26} = -49 \pm 3°$ (C 0.35, methanol);
4) Ultraviolet absorption spectrum: as shown in FIG. XV $UV_{MAX}^{CH3OH} = 225$ nm (ε27,400) 232 nm (ε25,700);
5) Infrared absorption spectrum: as shown in FIG. XVI (KBr disc): 3480, 2965, 2935, 2880, 1703, 1647, 1458, 1380, 1292, 1223, 1135, 1098, 984 cm$^{-1}$;
6) Proton nuclear magnetic resonance spectrum (CDCl$_3$): as shown in FIG. XVII;
7) Carbon-13 nuclear magnetic resonance spectrum (CDCl$_3$): as shown in FIG. XVIII and described in Table VI; and
8) Electron impact mass spectrum: as shown in FIG. XIX with accurate mass measurements and proposed elemental compositions indicated in Table VII.

LL-F28249δ:
1) Molecular weight: 616 (EI-MS)
2) Molecular formula: $C_{35}H_{52}O_9$
3) HPLC retention volume of 14.0 ml in the system indicated in Table VIII;
4) Ultraviolet absorption spectrum (methanol): as shown in FIG. XX;
5) Proton nuclear magnetic resonance spectrum (CDCL$_3$): as shown in FIG. XXI; and
6) Electron impact mass spectrum: as shown in FIG. XXII.

LL-F28249ε:
1) Molecular weight: 598 (EI-MS)
2) Molecular formula: $C_{35}H_{50}O_8$
3) HPLC retention volume of 14.8 ml in the system indicated in Table VIII;
4) Ultraviolet absorption spectrum (methanol): as shown in FIG. XXIII;
5) Proton nuclear magnetic resonance spectrum (CDCl$_3$): as shown in FIG. XXIV; and
6) Electron impact mass spectrum: as shown in FIG. XXV.

LL-F28249ζ:
1) Molecular weight: 598 (EI-MS)
2) Molecular formula: $C_{35}H_{50}O_8$
3) HPLC retention volume of 16.0 ml in the system indicated in Table VIII;
4) Ultraviolet absorption spectrum (methanol): as shown in FIG. XXVI;
5) Proton nuclear magnetic resonance spectrum (CDCL$_3$): as shown in FIG. XXVII; and
6) Electron impact mass spectrum: as shown in FIG. XXVIII.

LL-F28249η:
1) Molecular weight: 612 (EI-MS)
2) Molecular formula: $C_{36}H_{52}O_8$
3) HPLC retention volume of 23.5 ml in the system indicated in Table VIII;
4) Ultraviolet absorption spectrum (methanol): as shown in FIG. XXIX;
5) Proton nuclear magnetic resonance spectrum (CDCl$_3$): as shown in FIG. XXX; and
6) Electron impact mass spectrum: as shown in FIG. XXXI.

LL-F28249θ:
1) Molecular weight: 626 (EI-MS)
2) Molecular formula: $C_{37}H_{54}O_8$
3) HPLC retention volume of 24.5 ml in the system indicated in Table VIII;
4) Ultraviolet absorption spectrum (methanol): as shown in FIG. XXXII;
5) Proton nuclear magnetic resonance spectrum (CDCl$_3$): as shown in FIG. XXXIII; and
6) Electron impact mass spectrum: as shown in FIG. XXXIV.

LL-F28249ι:

1) Molecular weight: 626 (EI-MS)
2) Molecular formula: $C_{37}H_{54}O_8$
3) HPLC retention volume of 26.0 ml in the system indicated in Table VIII;
4) Ultraviolet absorption spectrum (methanol): as shown in FIG. XXXV;
5) Proton nuclear magnetic resonance spectrum (CDCl$_3$): as shown in FIG. XXXVI; and
6) Electron impact mass spectrum: as shown in FIG. XXXVII.

LL-F28249κ:
1) Molecular weight: 584 (EI-MS);
2) Molecular formula: $C_{35}H_{52}O_7$;
3) Specific optical rotation: $[\alpha]^{26}_D = +189°$ —(C 0.165 acetone);
4) Ultraviolet absorption spectrum: as shown in FIG. XXXIX $UV_{MAX}^{CH3OH} = 241$ nm (E20,400);
5) Infrared absorption spectrum: as shown in FIG. XL (KBr disc);
6) Electron impact mass spectrum: as shown in FIG. XLI;
7) Proton nuclear magnetic resonance spectrum (CDCl$_3$); as shown in FIG. XLII; and
8) Carbon-13 nuclear magnetic resonance spectrum (CDCl$_3$); as shown in FIG. XLIII and described in Table IX.

LL-F28249λ:
1) Molecular weight: 626 (FAB-MS);
2) Molecular formula: $C_{37}H_{54}O_8$;
3) Specific optical rotation: $[\alpha]_D^{26} = +145°$ (C, 0.23 acetone);
4) Ultraviolet absorption spectrum: as shown in FIG. XLIV $UV_{MAX}^{CH3OH} = 244$ nm (E30,000);
5) Infrared absorption spectrum: as shown in FIG. XLV (KBr disc);
6) Electron impact mass spectrum: as shown in FIG. XLVI;
7) Proton nuclear magnetic resonance spectrum (CDCl$_3$); as shown in FIG. XLVII; and
8) Carbon-13 nuclear magnetic resonance spectrum (CDCl$_3$); as shown in FIG. XLVIII and described in Table X.

LL-F28249μ:
1) Molecular weight: 612 (EI-MS);
2) Molecular formula: $C_{37}H_{56}O_7$;
3) Ultraviolet absorption spectrum: as shown in FIG. XLIX $UV_{MAX}^{CH3OH} = 241$ nm (E16,800);
4) Infrared absorption spectrum: as shown in FIG. L (KBr disc);
5) Electron impact mass spectrum: as shown in FIG. LI;
6) Proton nuclear magnetic resonance spectrum (CDCl$_3$); as shown in FIG. LII.

LL-F28249υ:
1) Molecular weight: 592 (EI-MS);
2) Molecular formula: $C_{36}H_{48}O_7$;
3) Specific optical rotation: $[\alpha]_D^{26} + 131°$ —(C0.325, acetone);
4) Ultraviolet absorption spectrum: as shown in FIG. LIII $UV_{MAX}^{CH3OH} = 256$ (E20,500); 358(E8,830);
5) Infrared absorption spectrum: as shown in FIG. LIV (KBr disc);
6) Electron impact mass spectrum: as shown in FIG. LV;
7) Proton nuclear maagnetic resonance spectrum (CDCl$_3$); as shown in FIG. LVI; and
8) Carbon-13 nuclear magnetic resonance spectrum (CDCl$_3$); as shown in FIG. LVII, and described in Table XI.

TABLE I

Carbon-13 NMR Data for LL-F28249α

| Carbon | Chemical Shift[1] (ppm) | Proton Substitution |
|---|---|---|
| 1 | 173.4 | q[2] |
| 2 | 142.8 | CH |
| 3 | 139.4 | q |
| 4 | 137.7 | q |
| 5 | 137.3 | q |
| 6 | 137.2 | CH |
| 7 | 130.6 | q |
| 8 | 123.3 | CH |
| 9 | 120.3[3] | CH |
| 10 | 118.0 | CH |
| 11 | 99.7 | q |
| 12 | 80.2 | q |
| 13 | 79.3 | CH |
| 14 | 76.7 | CH |
| 15 | 69.3 | CH |
| 16 | 68.5 | CH |
| 17 | 68.4 | CH$_2$ |
| 18 | 67.8 | CH |
| 19 | 67.7 | CH |
| 20 | 48.4 | CH$_2$ |
| 21 | 45.7 | CH |
| 22 | 41.1 | CH$_2$ |
| 23 | 40.7 | CH$_2$ |
| 24 | 36.1 | CH$_2$ |
| 25 | 36.0 | CH |
| 26 | 3;.9 | CH |
| 27 | 34.7 | CH$_2$ |
| 28 | 26.8 | CH |
| 29 | 22.8[4] | CH$_3$ |
| 30 | 22.2 | CH$_3$ |
| 31 | 19.9 | CH$_3$ |
| 32 | 15.5 | CH$_3$ |
| 33 | 13.9 | CH$_3$ |
| 34 | 11.0 | CH$_3$ |

[1]Downfield from TMS; CDCl$_3$ solution.
q = quaternary carbon.
[3,4]Two unresolved signals.

TABLE II

High Resolution Mass Measurements for LL-F28249α

| m/z | Elemental Composition |
|---|---|
| 612.3705 | $C_{36}H_{52}O_8$ |
| 594.3543 | $C_{36}H_{50}O_7$ |
| 576.3472 | $C_{36}H_{48}O_6$ |
| 484.3211 | $C_{30}H_{44}O_5$ |
| 482.2648 | $C_{29}H_{38}O_6$ |
| 466.3097 | $C_{30}H_{42}O_4$ |
| 448.2987 | $C_{30}H_{40}O_3$ |
| 442.2375 | $C_{26}H_{34}O_6$ |
| 425.2327 | $C_{26}H_{33}O_5$ |
| 354.2181 | $C_{23}H_{30}O_3$ |
| 314.1877 | $C_{20}H_{26}O_3$ |
| 278.1144 | $C_{15}H_{18}O_5$ |
| 265.1786 | $C_{16}H_{25}O_3$ |
| 248.1405 | $C_{15}H_{20}O_3$ |
| 247.1705 | $C_{16}H_{23}O_2$ |
| 237.1838 | $C_{15}H_{25}O_2$ |
| 219.1740 | $C_{15}H_{23}O$ |
| 151.0753 | $C_9H_{11}O_2$ |

TABLE IIa

Carbon-13 NMR Data for LL-F282498

| Carbon | Chemical Shift (ppm)* |
|---|---|
| 1 | 173.3 |
| 2 | 142.6 |
| 3 | 139.5 |
| 4 | 137.7 |
| 5 | 137.3 |
| 6 | 133.9 |

TABLE IIa-continued

Carbon-13 NMR Data for LL-F282498

| Carbon | Chemical Shift (ppm)* |
|---|---|
| 7 | 123.8 |
| 8 | 123.4 |
| 9 | 120.3 |
| 10 | 120.2 |
| 11 | 118.0 |
| 12 | 99.7 |
| 13 | 80.2 |
| 14 | 79.4 |
| 15 | 76.7 |
| 16 | 69.2 |
| 17 | 68.6 |
| 18 | 68.3 |
| 19 | 67.8 |
| 20 | 67.7 |
| 21 | 48.4 |
| 22 | 45.7 |
| 23 | 41.0 |
| 24 | 40.8 |
| 25 | 36.1 |
| 26 | 35.9** |
| 27 | 34.7 |
| 28 | 22.3 |
| 29 | 19.8 |
| 30 | 15.5 |
| 31 | 13.8 |
| 32 | 13.1 |
| 33 | 10.8 |

*Downfield from TMS; $CDCl_3$ solution
**Two unresolved signals

TABLE III

High Resolution Mass Measurements for LL-F282498

| m/s | Elemental Composition |
|---|---|
| 584.3388 | $C_{34}H_{48}O_8$ |
| 566.3306 | $C_{34}H_{46}O_7$ |
| 456.2864 | $C_{28}H_{40}O_5$ |
| 442.2391 | $C_{26}H_{34}O_6$ |
| 438.2780 | $C_{28}H_{38}O_4$ |
| 425.2331 | $C_{26}H_{33}O_5$ |
| 354.2187 | $C_{23}H_{30}O_3$ |
| 314.1858 | $C_{20}H_{26}O_3$ |
| 278.1168 | $C_{15}H_{18}O_5$ |
| 237.1491 | $C_{14}H_{21}O_3$ |
| 219.1380 | $C_{14}H_{19}O_2$ |
| 209.1534 | $C_{13}H_{21}O_2$ |
| 191.1418 | $C_{13}H_{19}O$ |
| 151.0750 | $C_9H_{11}O_2$ |

TABLE IV

Carbon-13 NMR Data for LL-F28249γ

| Carbon | Chemical Shift[1] (ppm) |
|---|---|
| 1 | 173.6 |
| 2 | 142.4 |
| 3 | 139.9 |
| 4 | 137.3 |
| 5 | 136.0 |
| 6 | 134.0 |
| 7 | 123.8 |
| 8 | 123.6 |
| 9 | 120.4 |
| 10 | 119.6 |
| 11 | 118.5 |
| 12 | 99.8 |
| 13 | 80.5 |
| 14 | 77.8 |
| 15 | 77.0 |
| 16 | 76.8 |
| 17 | 69.3 |
| 18 | 68.6 |
| 19 | 68.3 |
| 20 | 67.9 |
| 21 | 57.7 |

TABLE IV-continued

Carbon-13 NMR Data for LL-F28249γ

| Carbon | Chemical Shift[1] (ppm) |
|---|---|
| 22 | 48.5 |
| 23 | 45.8 |
| 24 | 41.2 |
| 25 | 40.8 |
| 26 | 36.2 |
| 27 | 36.1 |
| 28 | 36.0 |
| 29 | 34.8 |
| 30 | 22.3 |
| 31 | 19.9 |
| 32 | 15.5 |
| 33 | 13.8 |
| 34 | 13.1 |
| 35 | 10.8 |

[1]Downfield from TMS; $CDCl_3$ solution.

TABLE V

High Resolution Mass Measurements for LL-F28249γ

| m/s | Elemental Composition |
|---|---|
| 598.3534 | $C_{35}H_{50}O_8$ |
| 580.3422 | $C_{35}H_{48}O_7$ |
| 562.3292 | $C_{35}H_{46}O_6$ |
| 496.2824 | $C_{30}H_{40}O_6$ |
| 484.2440 | $C_{28}H_{36}O_7$ |
| 478.2687 | $C_{30}H_{38}O_5$ |
| 456.2576 | $C_{27}H_{36}O_6$ |
| 438.2772 | $C_{28}H_{38}O_4$ |
| 425.2341 | $C_{26}H_{33}O_5$ |
| 420.2651 | $C_{28}H_{36}O_3$ |
| 354.2199 | $C_{23}H_{30}O_3$ |
| 314.1875 | $C_{20}H_{26}O_3$ |
| 292.1307 | $C_{16}H_{20}O_5$ |
| 288.2075 | $C_{19}H_{28}O_2$ |
| 248.1397 | $C_{15}H_{20}O_3$ |
| 237.1490 | $C_{14}H_{21}O_3$ |
| 219.1382 | $C_{14}H_{19}O_2$ |
| 209.1544 | $C_{13}H_{21}O_2$ |
| 191.1435 | $C_{13}H_{19}O$ |
| 151.0759 | $C_9H_{11}O_2$ |

TABLE VI

Carbon-13 NMR Data for LL-F28249ω

| Carbon | Chemical Shift[1] (ppm) |
|---|---|
| 1 | 220.7 |
| 2 | 219.6 |
| 3 | 165.2 |
| 4 | 148.7 |
| 5 | 133.1 |
| 6 | 132.3 |
| 7 | 132.1 |
| 8 | 130.2 |
| 9 | 122.3 |
| 10 | 100.0 |
| 11 | 82.9 |
| 12 | 75.9 |
| 13 | 73.0 |
| 14 | 72.7 |
| 15 | 72.6 |
| 16 | 72.1 |
| 17 | 69.0 |
| 18 | 67.3 |
| 19 | 63.6 |
| 20 | 51.4 |
| 21 | 46.2 |
| 22 | 45.7 |
| 23 | 42.2[2] |
| 24 | 40.4 |
| 25 | 38.3 |
| 26 | 37.6 |
| 27 | 36.1 |
| 28 | 34.8 |

TABLE VI-continued

Carbon-13 NMR Data for LL-F28249ω

| Carbon | Chemical Shift[1] (ppm) |
|---|---|
| 29 | 33.5 |
| 30 | 30.1 |
| 31 | 26.6 |
| 32 | 25.4 |
| 33 | 24.5 |
| 34 | 23.0 |
| 35 | 21.1 |
| 36 | 17.9 |
| 37 | 14.3 |
| 38 | 14.2 |
| 39 | 12.1 |
| 40 | 11.5 |
| 41 | 10.9 |
| 42 | 8.7 |
| 43 | 8.3 |
| 44 | 5.7 |

[1]Downfield from TMS; $CDCl_3$ solution.
[2]Two unresolved signals.

TABLE VII

High Resolution Mass Measurements for LL-F28249ω

| m/s | Elemental Composition |
|---|---|
| 462.3360 | $C_{28}H_{46}O_5$ |
| 444.3237 | $C_{28}H_{44}O_4$ |
| 425.2534 | $C_{23}H_{37}O_7$ |
| 407.2439 | $C_{23}H_{35}O_6$ |
| 406.3046 | $C_{25}H_{42}O_4$ |
| 387.2895 | $C_{25}H_{39}O_3$ |
| 337.2010 | $C_{19}H_{29}O_5$ |
| 297.2031 | $C_{17}H_{29}O_4$ |
| 279.1944 | $C_{17}H_{27}O_3$ |
| 261.1851 | $C_{17}H_{25}O_2$ |
| 253.1797 | $C_{15}H_{25}O_3$ |
| 235.1697 | $C_{15}H_{23}O_2$ |
| 224.1754 | $C_{14}H_{24}O_2$ |
| 209.1530 | $C_{13}H_{21}O_2$ |
| 207.1744 | $C_{14}H_{23}O$ |
| 184.1458 | $C_{11}H_{20}O_2$ |
| 179.1048 | $C_{11}H_{15}O_2$ |
| 173.1205 | $C_9H_{17}O_3$ |
| 167.1051 | $C_{10}H_{15}O_2$ |
| 155.1069 | $C_9H_{15}O_2$ |

TABLE VIII

HPLC Retention Volumes for LL-F28249α, δ, ε, ζ, η, θ and ι

| Compound | Retention Volume* (ml) |
|---|---|
| LL-F28249α | 19.8 |
| LL-F28249δ | 14.0 |
| LL-F28249ε | 14.8 |
| LL-F28249ζ | 16.0 |
| LL-F28249η | 23.5 |
| LL-F28249θ | 24.5 |
| LL-F28249ι | 26.0 |

*System includes a column 3.9 mm × 30 cm packed with $C_{18}$ reverse phase packing developed with methanol:water (80:20) at 1.0 ml/minute, detection was by absorbance at 254 nm.

TABLE IX

Carbon-13 NMR Data for LL-F28249κ

| Carbon | Chemical Shift (ppm)* |
|---|---|
| 1 | 173.9 |
| 2 | 140.7 |
| 3 | 138.3 |
| 4 | 136.6 |
| 5 | 136.5 |
| 6 | 133.8 |
| 7 | 124.7 |
| 8 | 124.4 |
| 9 | 123.8 |
| 10 | 120.1 |
| 11 | 118.5 |
| 12 | 99.7 |
| 13 | 77.2 |
| 14 | 76.6** |
| 15 | 76.5 |
| 16 | 69.3 |
| 17 | 68.6 |
| 18 | 67.3 |
| 19 | 56.7 |
| 20 | 48.4 |
| 21 | 47.7 |
| 22 | 41.1 |
| 23 | 40.6 |
| 14 | 37.1 |
| 25 | 36.3 |
| 26 | 36.0 |
| 27 | 35.9 |
| 28 | 34.6 |
| 29 | 22.0 |
| 30 | 19.3 |
| 31 | 16.0 |
| 32 | 13.8 |
| 33 | 13.3 |
| 34 | 13.1 |
| 35 | 10.7 |

*Downfield from TMS; $CDCl_3$ solution.
**Coincident with $CDCl_3$ signals.

TABLE X

Carbon-13 NMR Data for LL-F28249λ

| Carbon | Chemical Shift (ppm)* |
|---|---|
| 1 | 173.6 |
| 2 | 142.5 |
| 3 | 139.8 |
| 4 | 137.4 |
| 5 | 137.2 |
| 6 | 136.0 |
| 7 | 130.7 |
| 8 | 123.6 |
| 9 | 120.3 |
| 10 | 119.7 |
| 11 | 118.6 |
| 12 | 99.8 |
| 13 | 80.5 |
| 14 | 77.7 |
| 15 | 77.6 |
| 16 | 76.7 |
| 17 | 69.3 |
| 18 | 68.6 |
| 19 | 68.3 |
| 20 | 67.9 |
| 21 | 57.8 |
| 22 | 48.6 |
| 23 | 45.8 |
| 24 | 41.2 |
| 25 | 40.9 |
| 26 | 36.1** |
| 27 | 36.0 |
| 28 | 34.9 |
| 29 | 26.9 |
| 30 | 23.0** |
| 31 | 22.4 |
| 32 | 20.0 |
| 33 | 15.7 |
| 34 | 14.0 |
| 35 | 11.1 |

*Downfield from TMS; $CDCl_3$ solution.
**Two unresolved signals.

TABLE XI

Carbon-13 NMR Data for LL-F28249υ

| Carbon | Chemical Shift (ppm)* |
|---|---|
| 1 | 167.4 |

TABLE XI-continued

Carbon-13 NMR Data for LL-F28249υ

| Carbon | Chemical Shift (ppm)* |
|---|---|
| 2 | 150.5 |
| 3 | 142.9 |
| 4 | 142.0 |
| 5 | 137.2** |
| 6 | 132.1 |
| 7 | 130.7 |
| 8 | 125.8 |
| 9 | 125.5 |
| 10 | 124.2 |
| 11 | 123.7 |
| 12 | 123.2 |
| 13 | 121.3 |
| 14 | 118.0 |
| 15 | 100.0 |
| 16 | 76.7 |
| 17 | 74.6 |
| 18 | 69.4 |
| 19 | 68.7 |
| 20 | 68.3 |
| 21 | 48.4 |
| 22 | 41.0** |
| 23 | 35.9 |
| 24 | 35.6 |
| 25 | 35.5 |
| 26 | 34.4 |
| 27 | 29.7 |
| 28 | 26.8 |
| 29 | 22.9 |
| 30 | 22.8 |
| 31 | 22.1 |
| 32 | 15.3 |
| 33 | 13.9 |
| 34 | 11.0 |

*Downfield from TMS; $CDCl_3$ solution.
**Two unresolved signals.

TABLE XII

| | Chromatographic Data | |
|---|---|---|
| Component | TLC* Relative Rf | HPLC** Retention Time (minutes) |
| α | 1.00 | 13.8 |
| β | .797 | 9.3 |
| γ | 1.42 | 12.6 |
| δ | .758 | 10.4 |
| ε | 1.06 | 10.9 |
| ζ | 1.12 | 11.5 |
| η | 1.03 | 16.2 |
| θ | 1.27 | 17.3 |
| ι | 1.27 | 18.2 |
| κ | 1.83 | 24.7 |
| λ | 1.56 | 19.1 |
| μ | 1.92 | 38.0 |
| ν | 1.95 | 42.3 |
| ω | .212 | 7.1 |

*Analtech Silica Gel GHLF250μ developed with ethyl acetate:methylene chloride (1:3), detection by charring with $H_2SO_4$.
**Altex Ultrasphere ODS 5μ 4.6 mm × 25 cm developed with 85% methanol in water at 1.0 ml/minute, detection by absorbance at 254 nm.

The new agents designated LL-F28249α, β, γ, δ ε, ζ, η, θ, ι, κ, λ, μ, ν and ω are formed during the cultivation, under controlled conditions of *Streptomyces cyaneogriseus noncyanogenus*, NRRL 15773.

This organism is maintained in the culture collection of the Medical Research Division, American Cyanamid Company, Pearl River, N.Y. as culture number LL-F28249. A viable culture of his new microorganism has been deposited with the Patent Culture Collection Laboratory, Northern Regional Research Center, U.S. Department of Agriculture, Peoria, Ill. 61604, and has been added to its permanent collection. It is freely available to the public in this depository under its accession number NRRL 15773.

For the production of these new agents the present invention is not limited to this particular organism. In fact, it is desired and intended to include the use of naturally-occurring mutants of this organism, as well as induced mutants produced from his organism by various mutagenic means known to those skilled in the art, such as exposure to nitrogen mustard, X-ray radiation, ultraviolet radiation, N'-methyl-N'-nitro-N-nitrosoguanidine, actinophages and the like. It is also desired and intended to include inter- and intraspecific genetic recombinants produced by genetic techniques known to those skilled in the art such as for example, conjugation, transduction and genetic engineering techniques.

General Fermentation Conditions

Cultivation of *Streptomyces cyaneogriseus noncyaneogenus*, NRRL 15773 may be carried out in a wide variety of liquid culture media. Media which are useful for the production of agents LL-F28249α, β, γ, δ, ε, ζ, η, θ, ι, κ, γ, μ, ν and ω include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

Example 1

Inoculum Preparation

A typical medium used to grow the various stages of inoculum was prepared according to the following formula:

| | |
|---|---|
| Dextrose | 1.0% |
| Dextrin | 2.0% |
| Yeast extract | 0.5% |
| NZ amine | 0.5% |
| Calcium carbonate | 0.1% |
| Water qs | 100% |

This medium was sterilized. A 100 ml portion of this sterile medium, in a flask, was inoculated with mycelial scrapings from an agar slant of *Streptomyces cyaneogriseus noncyanogenus* NRRL 15773. The medium was then agitated vigorously on a rotary shaker for 48–72 hours at 28° C. providing primary inoculum. This primary inoculum was then used to inoculate one liter of the above sterile medium, which was then grown aerobically at 28° C. for 48 hours providing secondary inoculum.

Example 2

Fermentation

A fermentation medium of the following formulation was prepared.

| | |
|---|---|
| Dextrin | 1.0% |
| Soya peptone | 1.0% |
| Molasses | 2.0% |

| Calcium carbonate | 0.1% |
| Water qs | 100% |

This medium was sterilized and then a 30 liter portion was inoculated with one liter of secondary inoculum prepared as described in Example 1. The fermentation was conducted at 30° C., with a sterile air flow of 30 liters per minute, backpressure of 8 psig and agitation by an impeller operated at 500 rpm for 91 hours at which time the mash was harvested.

Example 3

Isolation of LL-F28249α, β and γ

A total of 26 liters of whole harvest mash, prepared as described in Example 2 was mixed with 1500 g of diatomaceous earth and filtered. The mycelial cake was washed with 5 liters of water and the filtrate and wash discarded. The mycelial cake was mixed with 10 liters of methanol for one hour, then filtered and washed with 5 liters of methanol. The methanol extract and methanol wash were combined and evaporated to an aqueous residue of about 1-2 liters. This aqueous residue was mixed with twice its volume of methylene chloride and mixed for ½ hour. The methylene chloride phase was separated and then concentrated to a syrup giving 27 g of crude material.

This 27 g of crude material was dissolved in a mixture of methylene chloride and methanol, filtered through cotton and anhydrous sodium sulfate and then evaporated, giving 7.0 g of an oil.

A 170 g portion of silica gel was slurried in 12.5% ethyl acetate in methylene chloride and poured to form a column 2.5×58 cm. The oil was dissolved in 12.5% ethyl acetate in methylene chloride and applied to the column. The column was developed with the same solvent mixture. The mobile phase was run at 1.3 ml/minute initially and 15 minute fractions were collected. The flow rate slowed to about 0.5 ml/minute after 10 fractions, so fractions 1-10 were 20 ml decreasing to about 10 ml uniformly and fractions 11-98 were about 7 ml. At fraction 99 the flow rate was increased to give 25 ml fractions in 10 minutes. A total of 105 fractions were collected. These fractions were tested by thin layer chromatography in ethyl acetate:methylene chloride (1:1).

Fractions 30-54 were combined and evaporated giving 1.08 g of an oil containing LL-F28249γ.

Fractions 55-62 were combined and evaporated giving 150 mg of solid containing LL-F28249α and β.

The 150 mg of solid containing LL-F28249α and β was chromatographed by preparative HPLC using a reverse-phase column (Whatman C8, 2.2×50 cm) developed with 80% (v/v) methanol in water. The flow rate was about 10 ml/minute and 2 minute fractions were collected.

Fractions 58-69 were combined, the methanol was evaporated, t-butanol was added and the mixture was lyophilized, giving 60 mg of pure LL-F28249α.

Fractions 40-43 were combined, the methanol was evaporated and the residual aqueous suspension was extracted with methylene chloride which, upon evaporation, gave 10 mg of pure LL-F28249β.

The 1.08 g of oil containing LL-F28249γ was dissolved in 10% ethyl acetate in methylene chloride and applied to a column (2.5×50 cm) packed with silica gel. The column was developed with 10% ethyl acetate in methylene chloride, eluting at a flow rate of 2 ml/minute and collecting 12 minute fractions. Fractions 19-29 were combined and evaporated to a residue. This residue was purified by preparative reverse-phase chromatography as described for the α and β components. Fractions 55-62 were combined, the methanol was evaporated in vacuo, t-butanol was added and the mixture was lyophilized giving 60 mg of pure LL-F28249δ.

Example 4

Large Scale Fermentation

An inoculum of *Streptomyces cyaneogriseus noncyanogenus*, NRRL 15773 was prepared as described in Example 1, using 100 ml of primary inoculum to produce 10 liters of secondary inoculum.

Two 300 liter fermentations were conducted as described in Example 2 using 10 liters of the above secondary inoculum for each 300 liters of fermentation medium. At the end of 118 hours the mashes were harvested.

Example 5

Isolation of LL-F28249ω

A total of 450 liters of harvest mash from the two 300 liter fermentations described in Example 4 was treated as described in the first portion of Example 3 giving crude material as a syrup.

This syrupy residue was washed with hexane to remove non-polar materials and the remaining 9 g of insoluble material was subjected to Sephadex LH-20 partition chromatography.

The chromatographic column was prepared with 9 liters of Sephadex LH-20, previously swelled in methanol, to form a column 10×110 cm. The column was equilibrated by passing about 4800 ml of mobile phase [methylene chloride:hexane:methanol (10:10:1)] through it at a flow rate of 5 ml/minute. The 9 g of insoluble material was charged onto the column in 50 ml of the mobile phase. An initial forerun of 2150 ml was obtained at a flow rate of 5 ml/minute. The flow rate was then increased to 8 ml/minute and fractions were collected every 45 minutes. Fractions 9-12 were combined and the solvents evaporated in vacuo giving 4.9 g of residue.

This residue was dissolved in a 1:1 mixture of cyclohexane and ethyl acetate and allowed to evaporate slowly at room temperature. The addition of n-hexane gave a precipitate which was collected, giving 3.1 g of solid.

A 3.0 g portion of this solid was further purified by precipitation from 25 ml of methylene chloride using 50 ml of n-hexane.

The precipitate thus obtained was redissolved in 15 ml of methylene chloride and precipitated with 25 ml of n-hexane, giving 510 mg of pure LL-F28249ω.

Example 6

Isolation of LL-F28249δ, ε, ζ, η, θ and ι

Fractions 4-7 from the Sephadex LH-20 column described in Example 5 were combined and the solvents evaporated in vacuo to give 1.9 g of residue.

This residue was chromatographed on a 200 g silica gel column (2.5 cm × 83 cm) using 10% ethyl acetate in methylene chloride as the eluant. The flow rate was approximately 2 ml/minute and fractions were collected every 12 minutes.

Fractions 65–67 and 73–79 were combined together and the solvents were evaporated in vacuo to yield 250 mg of residue.

This 250 mg of residue was subjected to preparative reverse-phase chromatography as described in Example 3 except using 75% methanol in water as the mobile phase. The low rate was about 10 ml/minute. The first 2000 ml portion of eluate was diverted to waste then 72 fractions were collected at 2.0 minute intervals. After diverting another portion of eluate to waste (between 300–400 ml) fractions were collected again but at 2.5 minute intervals.

Fractions were combined as indicated below. The combined fractions were allowed to evaporate in a fume hood overnight, then the components were extracted into methylene chloride. Follwing evaporation of the solvent about 1 mg each of the pure components were obtained.

| Fractions Combined | Compound |
| --- | --- |
| 7–10 | LL-F28249δ |
| 19–22 | LL-F28249ε |
| 28–31 | LL-F28249ζ |
| 81–83 | LL-F28249η |
| 86–88 | LL-F28249θ |
| 93–95 | LL-F28249ι |

Example 7

Isolation of LL-F28249κ, λ, μ and υ

A total of 390 liters of fermentation mash, harvested from fermentations conducted as described in Example 2, was processed essentially as described in the first paragraph of Example 3, giving 120 ml of methylene chloride concentrate. This concentrate was diluted with 200 ml of hexane and chilled overnight at 4° C. The resulting precipitate was removed by filtration and discarded. The filtrate was diluted with 300 ml of hexane. The resulting precipitate (A) was collected by filtration and saved. This filtrate was evaporated to dryness and the oily residue was then dissolved in 200 ml of methylene chloride and diluted with 1700 ml of hexane. The resulting precipitate (B) was collected by filtration and saved. This filtrate was concentrated to an oily residue which was then redissolved in 50 ml of methylene chloride, 950 ml of methanol was added and this solution was stored at 4° C. for 3 days. The resulting precipitate was removed by filtration and discarded. The filtrate was evaporated to dryness and the residue (C) combined with (A) and (B) and subjected to chromatography as follows: The 5.0×109 cm column was slurry-packed with Woelm TSC silica gel in ethyl acetate:-methylene chloride (1:9). The column was developed with the same solvent mixture at a rate of 25 ml/minute. The first 2 liters of effluent were discarded, then sixteen 400 ml fractions were collected.

Fractions 2 and 3 were combined and evaporated giving 3.9 g of oily material (D).

Fractions 4 through 7 were combined and evaporated giving 9.5 g of oily material which was dissolved in hexane and chromatographed on a 2.5×10 cm column slurry-packed with 300 g of Woelm silica gel in ethyl acetate:hexane (1:4). The column was developed with the same solvent system at a rate of 4 ml/minute, collecting fractions at 7 minute intervals.

Fractions 45–54 were combined and evaporated, giving 0.3 g of material (E).

Fractions 63–135 were combined, evaporated to dryness, then redissolved in t-butanol and lyophilized giving 4.6 g of off-white solid (F).

LL-F28249κ and μ

Material (D) and (E) were combined and chromatographed on a 2.5×110 cm column packed with 300 g of Woelm silica gel, developing with ethyl acetate:hexane (1:9). The flow rate was maintained at 4 ml/minute and fractions were collected at 7 minute intervals.

Fractions 67–115 were combined and evaporated to dryness, giving 920 mg of residue (G).

This residue (G) was chromatographed by preparative HPLC using a reverse phase column (Whatman C8, 2.2×50 cm) and developing with 85% (v/v) methanol in water. The flow rate was about 10 ml/minute and fractions were collected at 2.5 minute intervals.

Fractions 33–40 were combined, concentrated to remove the methanol, then extracted with methylene chloride. The residue obtained upon evaporation was dissolved in t-butanol and then lyophilized, giving 60 mg of LLF28249κ.

Fractions 52–58 were similarly processed giving a small quantity of LL-F28249μ.

LL-F28249λ

A one gram portion of material (F) was chromatographed by reverse phase HPLC, as described above, except that 80% (v/v)methanol in water was used as eluent.

Fractions 61–75 were combined and processed as above, giving 100 mg of LL-F28249λ.

LL-F28249υ

A 396 g portion of material essentially the same as material (D) above, was dissolved in 500 ml of methanol and then chilled at 4° for several hours. The resulting precipitate was removed by filtration, washed with cold methanol and discarded. The combined filtrate and wash was evaporated. The residual oil was dissolved in hexane and charged on a 5×50 cm dry-packed silica gel column (Mallinkrodt SilicAR cc-7). The column was eluted with ethyl acetate:hexane (1.5:8.5) at a rate of about 50 ml/minute.

| Fraction | Volume (liters) |
| --- | --- |
| 1 | 1 |
| 2 | 4 |
| 3 | 1 |
| 4 | 2 |

Fraction 3 was evaporated, giving 5.0 g of residue which was purified by preparative reverse phase HPLC (Waters $C_{18}$, 5×60 cm). The column was initially developed with 16 liters of 80% methanol in water (v/v) at 100 ml/minute, then with 6.4 liters of 84% methanol in water (v/v). The first liter of effluent was discarded and then fractions of 400 ml were collected.

Fractions 44–47 were combined and processed as described above, giving 390 mg of LLF28249υ as a pale yellow solid.

Example 8

Anti-nematodal activity of LL-F28249, NRRL 15773

This in vitro assay is designed to utilize the free living nematode *Caenorhabditis elegans* (*C. elegans*) to detect the anti-nematodal activity of fermentation broths against microorganisms from the soil. The assay procedure consists of micropipetting 50 μl of each broth into one of 96 wells of a microculture plate and adding 10 μl of a three to four day-old culture of *C. elegans* (in all stages of development) suspended in *C. briggsae* Maintance Medium. The effects of the fermentation broths are observed and recorded at 48 hours after the initial mixing of broth and nematodes.

LL-F28249, NRRL 15773, broth killed all the adults and markedly reduced the survival and mobility of various larval stages in both the initial and in a replicate assay.

EXAMPLE 9

In vivo anthelmintic activity of LL-F28249, NRRL 15773

This in vivo system is designed to detect potential anthelmintic activity of all fermentation products found to have anti-nematodal action against *C. elegans*. Samples of LL-F28249, NRRL 15773 are mixed into feed, at concentrations of from 0.0031% to 2.0% (31 ppm to 20,000 ppm). Medicated diet containing the varying concentrations of LL-F28249, NRRL 15773 is given to gerbils infected with 400 third-stage larvae of *Trichostrongylus colubriformis*. The medicated feed is fed ad libitum, starting when the infection is seven days old, for three and one-half to four days, at which time the gerbils are necropsied. The intestines are removed and placed in water in an incubator at 45° C. for two hours to allow the parasites to migrate from the tissue. The efficacy of each treatment is determined by counting the number of *T. colubriformis* recovered compared to an untreated control. The results of these experiments, summarized in Table XIII below, demonstrate the anthelmintic activity of LL-F28249 as administered in feed, and when administered as a single oral drench, and by subcutaneous injection.

TABLE XIII

Anthelmintic activity of active ingredients from LL-F28249, NRRL 15773 culture against *Trichostrongylus colubriformis* in the gerbil

F28249

| | With medicated diet. Ad libitum | | | | | |
|---|---|---|---|---|---|---|
| Whole mash (lyophilized) | Conc. (ppm) | 500.0 | 250.0 | 125.0 | 62.5 | |
| | Efficacy % | 100.0 | 98.0 | 88.0 | 40.0 | |
| α | Conc.(ppm) | 20.0 | 0.5 | 0.1 | 0.05 | |
| | Efficacy % | 100.0 | 100.0 | 97.0 | 31.0 | |
| | With single oral drench | | | | | |
| Whole Mash (lyophilized) | Dose (mg/kg) | 200.0 | 100.0 | 50.0 | 25.0 | |
| | Efficacy % | 100.0 | 100.0 | 100.0 | 88.0 | |
| α | Dose (mg/kg) | 10.0 | 0.5 | 0.1 | 0.05 | 0.025 |
| | Efficacy % | 100.0 | 100.0 | 100.0 | 99.0 | 6.0 |
| γ | | — | — | 0.1 | 0.05 | 0.025 |
| | | | | 78.0 | 15.0 | 10.0 |
| ω | | — | — | 0.1 | — | — |
| | With subcutaneous injection | | | | | |
| Whole Mash (lyophilized) | Dose (mg/kg) | 200.0 | 100.0 | 50.0 | 25.0 | |
| | Efficacy % | 100.0 | 100.0 | 100.0 | 70.0 | |
| α | Dose (mg/kg) | 1.0 | 0.2 | 0.1 | | |
| | Efficacy % | 100.0 | 99.5 | 60.0 | | |

EXAMPLE 10

The anthelmintic activity of LL-F28249α against parasitic nematodes in sheep

This experiment is designed to evaluate the activity of LL-F28249α against the economically important parasites of sheep. The sheep are experimentally inoculated with infective larvae of *Haemonchus contortus*, *Ostertagia circumcincta* and *Trichostrongylus coluriformis*, to build up infections against which LL-F28249a will be challenged. Twenty-one days after inoculation, infection levels are determined by standard stoll count nematode counting procedures to determine the number of eggs of each species per gram of feces. The sheep are assigned randomly across three replicates of treatment and control groups based upon nematode egg counts. Twenty-two days after infection the sheep are treated with LL-F28249α using the doses and routes of administration shown in Table XIV below. Seven and eight days after treatment, the sheep are sacrificed and the worms are recovered using standard anthelmintic evaluation procedures. The efficacy of each treatment against each species is determined by comparing the number of worms at the respective dosage rate against the number of worms recovered in the three untreated control animals. The results of these evaluations, summarized in Table XIV below, demonstrate the high degree of effectiveness of LL-F28249α as an anthelmintic agent.

TABLE XIV

Anthelmintic efficacy of F28249α against *Haemonchus, Ostertagia* and *Trichostrongylus* in sheep

| Dose mg/kg | Route of administration | Efficacy (%) against | | |
|---|---|---|---|---|
| | | Haemonchus | Ostertagia | T. colubriformis |
| 1.0 | oral | 100.0 | 100.0 | 99.9 |
| 0.2 | oral | 100.0 | 100.0 | 99.9 |
| 0.1 | oral | 100.0 | 95.4 | 99.9 |
| 1.0 | IM | 100.0 | 100.0 | 100.0 |
| 0.2 | IM | 100.0 | 100.0 | 100.0 |
| | | Mean number of worms recovered (range) | | |
| 0.0 | — | 2683.0 | 881.0 | 16200.0 |

IM = Intermuscular

EXAMPLE 11

Efficacy of antibiotic LL-F28249α against the parasitic insect, *Melophagus ovinus*, (the sheep ked) on sheep This experiment is conducted concurrently on the same sheep used for the determination of anthelmintic activity as reported in Example 10. During the handling of the sheep prior to treatment, said sheep are observed for harbouring of natural infestations of *M. ovinus*. One half of each sheep is inspected for the indications of anti-ectoparasitic activity at necropsy, seven days after treatment.

The left side of each sheep is slowly sheared with electric clippers and inspected for living and dead sheep keds. The degree of infestation is approximated by the numbers of pupae found in the wool during the inspection and are rated 0 through +++, indicating no pupae to many pupae. The number of keds are recorded for each sheep, without knowledge of the treatment levels to eliminate bias. Initially, the keds were scored as alive or dead, but as experience was gained, some keds were scored as moribund because of abnormally-slow behavior.

Although there is a wide variation in the number of keds found on the sheep, the data summarized in Table XV below demonstrate that LL-F28249α is effective against *M. ovinus* and that said agent possesses systemic ectoparasiticide activity. In treated animals the numbers of live keds is effectively reduced and the number of dead keds increased in the intramuscularly-treated sheep.

TABLE XV

Efficacy of agent F28249α against *Melophagus ovinus* on sheep

| Dose mg/kg | Route of administration | Mean number of keds[a] Alive | Dead | % |
|---|---|---|---|---|
| 1.0 | Intramuscular | 1.67 | 1.67 | 78.22 |
| 0.2 | Intramuscular | 1.0 | 4.33 | 86.96 |
| 1.0 | Oral | 7.67 | 0.0 | 0.0 |
| 0.2 | Oral | 2.67 | 3.0 | 65.0 |
| 0.1 | Oral | 22.0 | 1.67 | 0.0 |
| Control | None | 7.67 | .67 | — |

[a]Three sheep per dose

[b]Efficacy % = 100 × $\frac{\text{Mean number in control} - \text{mean number in treated}}{\text{Mean number in control}}$

EXAMPLE 12

Insecticidal activity of the compounds of the invention

The insecticidal activity of the compounds of the present invention against a variety of insects at various concentrations of active ingredient in acetone-water solutions is determined by the following insecticidal test examples. The results of these tests are summarized in Table XVI.

A) *Hellothis virescens*, egg, tobacco budworm.

A young cotton leaf about 7–8 cm long is dipped and agitated in a test suspension for three seconds. Eggs are collected on cheesecloth that is cut into 10–20 mm squares containing about 50–100 eggs (6–30 hours old). A square of cheesecloth with eggs also is dipped in the test suspension and placed on the treated leaf. The combination is placed in the hood to dry. Following this, the combination is placed in an 8 ounce Dixie cup #2168-ST (240 mL, 6 cm tall, top diameter 9.5 cm, bottom diameter 8 cm) containing a 5 cm length of damp dental wick. A clear plastic lid is put on the top of the cup, and the treatments held for three (3) days before mortality counts are made.

B) *Aphis fabae*, mixed instars, bean aphids.

Pots containing single masturtium plant (Tropaeolum sp), about 5 cm tall, are infested with about 100 aphids one day before the test. In a hood, each plant is sprayed with the test suspension for 2 revolutions of a 4 rpm turntable using a #154 DeVilluss atomizer. The pots are set on their side on white enamel trays and held for two (2) days. After that time, mortality estimates of the aphids are made.

C) *Empoasca abrupta*, adult, western potato leafhopper.

A Sieva lima bean leaf about 5 cm long is dipped and agitated in the test suspension for three (3) seconds and then placed in a hood to dry. The leaf is placed in a 100×10 mm petri dish containing a moist filter paper on the bottom of the dish. Ten, adult leafhoppers are added to each dish, and the treatments are kept for three (3) days after which time mortality counts are made.

D) *Trichoplusia ni*, Third-instar larvae, cabbage looper.

The leaves of a Sieva lima bean plant expanded to 7–8 cm in length are dipped and agitated in a test suspension for three (3) seconds and then placed in a hood to dry. A leaf is then excised and placed in a 100×10 mm petri dish containing a damp filter paper on the bottom and ten third-instar larvae are placed therein. The dish is maintained for three (3) days before observations are made of mortality and reduced feeding.

E) *Spodoptera eridanis*, third-instar larvae, southern armyworm.

The leaves of a Sieva lima bean plant expanded to 7–8 cm in length are dipped and agitated in the test suspension for three (3) seconds and placed in a hood to dry. A leaf is then excised and placed in a 100×10 mm petri dish containing a damp filter paper on the bottom and ten (10) third-instar larvae are added. The dish is maintained for five (5) days before observations are made of mortality, reduced feeding or any interference with normal moulting.

F) *Heliothis virescens*, third-instar larvae, tobacco budworm.

Cotton cotyledons are dipped in the test suspension and placed in a hood to dry. The cotyledon is cut into 4 sections, and each section is placed in a 30 ml plastic medicine cup containing a 5–7 mm piece of moist dental wick. One third-instar larvae are added to each cup and a cardboard lid placed on the cup. Treatments are maintained for three (3) days before mortality counts and estimates of reduction in feeding are made.

G) *Musca domestica*, house fly.

The desired concentration of the test compound is added to the standard CSMA alfalfa-bran larval medium. House flies' eggs, 0–4 hours of age, are added to the treated medium. The treated medium is maintained and observations on egg hatch, larval growth and adult emergence are made.

H) *Tribolium confusum*, confused flour beetle.

Confused flour beetles (*Tribolium confusum*) are obtained from laboratory colonies reared on a whole wheat and white flour mixture. For this test, white flour is treated with an acetone solution of the test material using 1 ml of solution per 5 grams of flour in a 30 ml wide-mouth jar. The acetone is evaporated off in a hood overnight. The contents are stirred with a spatula to break up lumps formed by the test solution. The jar is then placed on a VORTES-GENIE ® vibrating mixer to thoroughly mix the test materials throughout the diet. Ten adult confused flour beetles are placed in each jar and the jar loosely capped. After five (5) days to allow oviposition, the beetles are removed and notations made of any mortality. At two (2) and four (4) weeks after initial infestation, observations are made of the number and size of trails produced by the developing larvae throughout the treated flour. Such observations give an indication of delayed growth, kill of eggs or larvae or any other interference in the normal growth pattern. After about nine (9) weeks at 27° C., the adult beetles emerge and the final observations are made by passing the contents of each jar through a 50-mesh screen sieve. These observations include the number of adults, pupae and larvae, as well as examination of the debris which did not pass through the screen in order to determine if there are any dead eggs or neonates.

I) *Tetranychus urticae* (P-resistant strain), 2-spotted spider mite.

Sieva lima bean plants with primary leaves expanded to 7–8 cm are selected and cut back to one plant per pot. A small piece is cut from a leaf taken from the main colony and placed on each leaf of the test plants. This is done about two (2) hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped and agitated in the test formulation for three (3) seconds and set in the hood to dry. Plants are kept for two (2) days before estimates of adult kill are made by using the first leaf. The second leaf is kept on the plant for another five (5) days before observations are made of the kill of eggs and/or newly emerged nymphs.

J) Southern armyworm (*Spodoptera eridania*), third-instar, cut-stem systemic test.

The compound is formulated as an emulsion containing 0.1 gm of the test material, 0.1 gm of a polyethoxylated vegetable oil in 0.4 g water, 10 mL of acetone and 90 mL of water. This is diluted ten-fold with water to give the 100 ppm emulsion for the test. Sieva lima bean plants with just the primary leaves expanded are used in this test. These leaves are cut off at least 2.5 cm above the soil level to avoid contamination with soil bacteria which may cause decay of the stem during the test. The cut stems are placed in the test emulsion. After three (3) days of uptake, a leaf is excised and placed in a 100×10 mm petri dish containing a moist filter paper on the bottom and ten third-instar larvae. Mortality counts and estimates of reduced feeding are made after three (3) days.

K) *Thrips palmi*, thrips.

Heavily infested leaves of cotton seedings are sprayed under field conditions at the desired concentrations. The number of thrips are counted before and after spraying. Percent control is based on these counts.

L) *Tetranychus urticae* (P-resistant strain), two spotted spider mite.

The compound is formulated as an emulsion containing 0.1 gm of the test material, 0.1 gm of a polyethoxylated vegetable oil in 0.4 g water, 10 mL of acetone and 90 mL of water. This is diluted ten-fold with water to give the 100 ppm emulsion for the test. Sieva lima bean plants with just the primary leaves expanded are used in this test. They are cut off at least 2.5 cm above the soil level to avoid contamination with soil bacteria which may cause decay of the stem during the test. The cut stems are placed in the test emulsions. Each leaf is infested with approximately 100 adult mites and maintained for three (3) days at which time mortality counts are made.

2. The method according to claim 1, said method comprising: administering an effective amount of the agent designated LL-F28249α, wherein the substantially pure form:
 (a) has a molecular weight of 612 (FAB-MS);
 (b) has a molecular formula $C_{36}H_{52}O_8$;
 (c) has a specific optical rotation $[\alpha]_D^{26} = +133+3°$ (C, 0.3, acetone);
 (d) has a characteristic ultraviolet absorption spectrum as shown in FIG. I of the attached drawings;
 (e) has a characteristic infrared absorption spectrum (KBr disc) as shown in FIG. II of the attached drawings;
 (f) has a characteristic proton nuclear magnetic resonance spectrum (CDCl$_3$) as shown in FIG. III of the attached drawings;
 (g) has a characteristic carbon-13 nuclear magnetic resonance spectrum (CDCl$_3$) as shown in FIG. IV of the attached drawings; and
 (h) has a characteristic electron impact mass spectrum as shown in FIG. V of the attached drawings.

3. The method according to claim 1, said method comprising: administering an effective amount of the agent designated LL-F28249β, wherein the substantially pure form:
 (a) has a molecular weight of 584 (FAB-MS);
 (b) has a molecular formula $C_{34}H_{48}O_8$;
 (c) has a specific optical rotation $[\alpha]_D^{26} = +125°$ (C, 0.3, acetone);
 (d) has a characteristic ultraviolet absorption spectrum as shown in FIG. VI of the attached drawings;
 (e) has a characteristic infrared absorption spectrum (KBr disc) as shown in FIG. VII of the attached drawings;
 (f) has a characteristic proton nuclear magnetic resonance spectrum (CDCl$_3$) as shown in FIG. VIII of the attached drawings;
 (g) has a characteristic carbon-13 nuclear magnetic

TABLE XVI

| | | | | | | | Confused flour beetle | | | | Plant Systemic Activity | |
|---|---|---|---|---|---|---|---|---|---|---|---|---|
| | | | | | Insecticidal and and Miticidal Activity of F-28,249α and F-28,249γ Percent Mortality | | | | | | | |
| Compound | Concn. in ppm | Cabbage loopers | Southern army-worms | Tobacco but-worms | Tobacco bud-worms eggs | Bean aphid | Western potato leaf hoppers | larvae and/ or pupae | House fly larvae | Thrips | Mites | Southern army-Worms | Mites |
| F-28,249α | 1000 | 100 | 100 | 100 | — | — | 55* | 100 | 100 | 93 | — | — | — |
| F-28,249α | 300 | 100* | — | 100 | 100 | — | 50 | — | 100 | 89 | 100 | — | — |
| F-28,249α | 100 | — | 60* | 100* | 100 | 100 | — | 97 | — | — | 100 | 60 | 100 |
| F-28,249γ | 1000 | — | 40 | 50* | 100 | 100 | 20 | — | — | — | 100 | — | — |
| F-28,249γ | 100 | — | 0 | 0 | 0 | 100 | 0 | — | — | — | 90 | — | — |

*Feeding deterent (anti-feeding properties)

What is claimed is:

1. A method for the control of plant nematodes, said method comprising: applying to the foliage of plants, the soil in which they are grown or into the trunks thereof, a nematocidally-effective amount of an agent designated LL-F28249α, LL-F28249β, LL-F28249γ, LL-F28249δ, LL-F28249ε, LL-F28249ζ, LL-F28249η, LL-F28249θ, LL-F28249ι, LL-F28249κ, LL-F28249λ, LL-F28249μ, LL-F28249ν, and LL-F28249ω; or a pharmaceutically and pharmacologically acceptable salt thereof, wherein the agents have characteristic spectra as shown in FIGS. I–LVII of the attached drawings.

resonance spectrum (CDCl$_3$) as shown in FIG. XXXVIII of the attached drawings; and
 (h) has a characteristic electron impact mass spectrum as shown in FIG. IX of the attached drawings.

4. The method according to claim 1, said method comprising: administering an effective amount of the agent designated LL-F28249γ, wherein the substantially pure form:
 (a) has a molecular weight of 598 (FAB-MS);
 (b) has a molecular formula $C_{35}H_{50}O_8$;
 (c) has a specific optical rotation $[\alpha]_D^{26} = +150+4°$ (C, 0.3, acetone);

(d) has a characteristic ultraviolet absorption spectrum as shown in FIG. X of the attached drawings;

(e) has a characteristic infrared absorption spectrum (KBr disc) as shown in FIG. XI of the attached drawings;

(f) has a characteristic proton nuclear magnetic resonance spectrum (CDCl$_3$) as shown in FIG. XII of the attached drawings;

(g) has a characteristic carbon-13 nuclear magnetic resonance spectrum (CDCl$_3$) as shown in FIG. XIII of the attached drawings; and (h) has a characteristic electron impact mass spectrum as shown in FIG. XIV of the attached drawings.

5. The method according to claim 1, said method comprising: administering an effective amount of the agent designated LL-F28249δ, wherein the substantially pure form:

(a) has a molecular weight of 616 (EI-MS);
(b) has a molecular formula $C_{35}H_{52}O_9$;
(c) has an HPLC retention volume of 14.0 ml;
(d) has a characteristic ultraviolet absorption spectrum (methanol) as shown in FIG. XX of the attached drawings;
(e) has a characteristic proton nuclear magnetic resonance spectrum (CDCl$_3$) as shown in FIG. XXI of the attached drawings; and
(f) has a characteristic electron impact mass spectrum as shown in FIG. XXII of the attached drawings.

6. The method according to claim 1, said method comprising: administering an effective amount of the agent designated LL-F28249ε, wherein the substantially pure form:

(a) has a molecular weight of 598 (EI-MS);
(b) has a molecular formula $C_{35}H_{50}O_8$;
(c) has an HPLC retention volume of 14.8 ml;
(d) has a characteristic ultraviolet absorption spectrum (methanol) as shown in FIG. XXIII of the attached drawings;
e) has a characteristic proton nuclear magnetic resonance spectrum (CDCl$_3$) as shown in FIG. XXIV of the attached drawings; and
f) has a characteristic electron impact mass spectrum as shown in FIG. XXV of the attached drawings.

7. The method according to claim 1, said method comprising: administering an effective amount of the agent designated LL-F28249ζ, wherein the substantially pure form:

(a) has a molecular weight of 598 (EI-MS);
(b) has a molecular formula $C_{35}H_{50}O_8$;
(c) has an HPLC retention volume of 16.0 ml;
(d) has a characteristic ultraviolet absorption spectrum (methanol) as shown in FIG. XXVI of the attached drawings;
e) has a characteristic proton nuclear magnetic resonance spectrum (CDCl$_3$) as shown in FIG. XXVII of the attached drawings; and
(f) has a characteristic electron impact mass spectrum as shown in FIG. XXVIII of the attached drawings.

8. The method according to claim 1, said method comprising: administering an effective amount of the agent designated LL-F28249η, wherein the substantially pure form:

(a) has a molecular weight of 612 (EI-MS);
(b) has a molecular formula $C_{36}H_{52}O_8$;
(c) has an HPLC retention volume of 23.5 ml;
(d) has a characteristic ultraviolet absorption spectrum (methanol) as shown in FIG. XXIX of the attached drawings;
(e) has a characteristic proton nuclear magnetic resonance spectrum (CDCl$_3$) as shown in FIG. XXX of the attached drawings; and
(f) has a characteristic electron impact mass spectrum as shown in FIG. XXXI of the attached drawings.

9. The method according to claim 1, said method comprising: administering an effective amount of the agent designated LL-F28249θ, wherein the substantially pure form:

(a) has a molecular weight of 626 (EI-MS);
(b) has a molecular formula $C_{37}H_{54}O_8$;
(c) has an HPLC retention volume of 24.5 ml;
(d) has a characteristic ultraviolet absorption spectrum (methanol) as shown in FIG. XXXII of the attached drawings;
(e) has a characteristic proton nuclear magnetic resonance spectrum (CDCl$_3$) as shown in FIG. XXXIII of the attached drawings; and
(f) has a characteristic electron impact mass spectrum as shown in FIG. XXXIV of the attached drawings.

10. The method according to claim 1, said method comprising: administering an effective amount of the agent designated LL-F28249ι, wherein the substantially pure form:

(a) has a molecular weight of 626 (EI-MS);
(b) has a molecular formula $C_{37}H_{54}O_8$;
(c) has an HPLC retention volume of 26.0 ml;
(d) has a characteristic ultraviolet absorption spectrum (methanol) as shown in FIG. XXXV of the attached drawings;
(e) has a characteristic proton nuclear magnetic resonance spectrum (CDCl$_3$) as shown in FIG. XXXVI of the attached drawings; and
(f) has a characteristic electron impact mass spectrum as shown in FIG. XXXVII of the attached drawings.

11. The method according to claim 1, said method comprising: administering an effective amount of the agent designated LL-F28249κ, wherein the substantially pure form:

(a) has a molecular weight of 584 (EI-MS);
(b) has a molecular formula $C_{35}H_{52}O_7$;
(c) has a specific optical rotation $[\alpha]_D^{26} = +189°$ (C, 0.165, acetone);
(d) has a characteristic ultraviolet absorption spectrum (methanol) as shown in FIG. XXXIX of the attached drawings;
(e) has a characteristic infrared absorption spectrum (KBr disc) as shown in FIG. XL of the attached drawings;
(f) has a characteristic electron impact mass spectrum as shown in FIG. XLI of the attached drawings;
(g) has a characteristic proton nuclear magnetic resonance spectrum (CDCl$_3$) as shown in FIG. XLII of the attached drawings; and
(h) has a characteristic carbon-13 nuclear magnetic resonance spectrum (CDCl$_3$) as shown in FIG. XLIII of the attached drawings.

12. The method according to claim 1, said method comprising: administering an effective amount of the agent designated LL-F28249λ, wherein the substantially pure form:

(a) has a molecular weight of 626 (FAB-MS);
(b) has a molecular formula $C_{37}H_{54}O_8$;

(c) has a specific optical rotation $[\alpha]_D^{26} = +145°$ (C, 0.23, acetone);

(d) has a characteristic ultraviolet absorption spectrum (methanol) as shown in FIG. XLIV of the attached drawings;

(e) has a characteristic infrared absorption spectrum (KBr disc) as shown in FIG. XLV of the attached drawings;

(f) has a characteristic electron impact mass spectrum as shown in FIG. XLVI of the attached drawings;

(g) has a characteristic proton nuclear magnetic resonance spectrum (CDCl$_3$) as shown in FIG. XLVII of the attached drawings; and (h) has a characteristic carbon-13 nuclear magnetic resonance spectrum (CDCl$_3$) as shown in FIG. XLVIII of the attached drawings.

13. The method according to claim 1, said method comprising: administering an effective amount of the agent designated LL-F28249μ, wherein the substantially pure form:

(a) has a molecular weight of 612 (EI-MS);

(b) has a molecular formula C$_{37}$H$_{56}$O$_7$;

(c) has a characteristic ultraviolet absorption spectrum (methanol) as shown in FIG. XLIX of the attached drawings;

(d) has a characteristic infrared absorption spectrum (KBr disc) as shown in FIG. L of the attached drawings;

(e) has a characteristic electron impact mass spectrum as shown in FIG. LI of the attached drawings; and (f) has a characteristic proton nuclear magnetic resonance spectrum (CDCl$_3$) as shown in FIG. LII of the attached drawings.

14. The method according to claim 1, said method comprising: administering an effective amount of the agent designated LL-F28249υ, wherein the substantially pure form:

(a) has a molecular weight of 592 (EI-MS);

(b) has a molecular formula C$_{36}$H$_{48}$O$_7$;

(c) has a specific optical rotation $[\alpha]_D^{26} = +131°$ (C, 0.325, acetone);

(d) has a characteristic ultraviolet absorption spectrum (methanol) as shown in FIG. LIII of the attached drawings;

(e) has a characteristic infrared absorption spectrum (KBr disc) as shown in FIG. LIV of the attached drawings;

(f) has a characteristic electron impact mass spectrum as shown in FIG. LV of the attached drawings;

(g) has a characteristic proton nuclear magnetic resonance spectrum (CDCl$_3$) as shown in FIG. LVI of the attached drawings; and (h) has a characteristic carbon-13 nuclear magnetic resonance spectrum (CDCl$_3$) as shown in FIG. LVII of the attached drawings.

15. The method according to claim 1, said method comprising: administering an effective amount of the agent designated LL-F28249ω, wherein the substantially pure form:

(a) has a molecular weight of 806 (FAB-MS);

(b) has a molecular formula C$_{45}$H$_{74}$O$_{12}$;

(c) has a specific optical rotation $[\alpha]_D^{26} = -49 \pm 3°$ (C, 0.35, methanol):

(d) has a characteristic ultraviolet absorption spectrum (methanol) as shown in FIG. XV of the attached drawings;

(e) has a characteristic infrared absorption spectrum (KBr disc) as shown in FIG. XVI of the attached drawings;

(f) has a characteristic proton nuclear magnetic resonance spectrum (CDCl$_3$) as shown in FIG. XVII of the attached drawings;

(g) has a characteristic carbon-13 nuclear magnetic resonance spectrum (CDCl$_3$) as shown in FIG. XVIII of the attached drawings; and (h) has a characteristic electron impact mass spectrum as shown in FIG. XIX of the attached drawings.

16. The method according to claim 1, 2, 3, 4, 5, 6, 7, 8, 9, 10, 11, 12, 13, 14, or 15, wherein about 0.1 to 1.4 kg per hectare of active ingredient is applied.

17. A method for the control of plant acarids or insects, said method comprising: applying to the breeding ground, food supply or habitat of the acarids or insects an acaricidally- or insecticidally-effective amount of the fermentation broth or whole mash of microorganism *Streptomyces cyaneogriseus noncyanogenus*, having deposit accession number NRRL 15773, or a mutant thereof.

18. The method according to claim 17, wherein said fermentation broth or whole mash of microorganism *Streptomyces cyaneogriseus noncyanogenus* contains agents designated LL-F28249α, LL-F28249β, LL-F28249γ, LL-F28249δ, LL-F28249ε, LL-F28249ζ, LL-F28249η, LL-F28249θ, LL-F28249ι, LL-F28249κ, LL-F28249λ, LL-F28249μ, LL-F28249υ, and LL-F28249ω; or the pharmaceutically and pharmacologically-acceptable salts thereof, wherein said agents have characteristic spectra as shown in FIGS. I–LVII of the attached drawings.

19. The method according to claim 18, said method comprising: applying an effective amount of the agent designated LL-F28249α, wherein the substantially pure form:

(a) has a molecular weight of 612 (FAB-MS);

(b) has a molecular formula C$_{36}$H$_{52}$O$_8$;

(c) has a specific optical rotation $[\alpha]_D^{26} = +133 \pm 3°$ (C, 0.3, acetone);

(d) has a characteristic ultraviolet absorption spectrum as shown in FIG. I of the attached drawings;

(e) has a characteristic infrared absorption spectrum (KBr disc) as shown in FIG. II of the attached drawings;

(f) has a characteristic proton nuclear magnetic resonance spectrum (CDCl$_3$) as shown in FIG. III of the attached drawings;

(g) has a characteristic carbon-13 nuclear magnetic resonance spectrum (CDCl$_3$) as shown in FIG. IV of the attached drawings; and (h) has a characteristic electron impact mass spectrum as shown in FIG. V of the attached drawings.

20. The method according to claim 18, said method comprising: applying an effective amount of the agent designated LL-F28249β, wherein the substantially pure form:

(a) has a molecular weight of 584 (FAB-MS);

(b) has a molecular formula C$_{34}$H$_{48}$O$_8$;

(c) has a specific optical rotation $[\alpha]_D^{26} = +125°$ (C, 0.3, acetone);

(d) has a characteristic ultraviolet absorption spectrum as shown in FIG. VI of the attached drawings;

(e) has a characteristic infrared absorption spectrum (KBr disc) as shown in FIG. VII of the attached drawings;
(f) has a characteristic proton nuclear magnetic resonance spectrum (CDCl$_3$) as shown in FIG. VIII of the attached drawings;
(g) has a characteristic carbon-13 nuclear magnetic resonance spectrum (CDCl$_3$) as shown in FIG. XXXVIII of the attached drawings; and
(h) has a characteristic electron impact mass spectrum as shown in FIG. IX of the attached drawings.

21. The method according to claim 18, said method comprising: applying an effective amount of the agent designated LL-F28249γ, wherein the substantially pure form:
(a) has a molecular weight of 598 (FAB-MS);
(b) has a molecular formula C$_{35}$H$_{50}$O$_8$;
(c) has a specific optical rotation $[\alpha]_D^{26} = +150 \pm 4°$ (C, 0.3, acetone);
(d) has a characteristic ultraviolet absorption spectrum as shown in FIG. X of the attached drawings;
(e) has a characteristic infrared absorption spectrum (KBr disc) as shown in FIG. XI of the attached drawings;
(f) has a characteristic proton nuclear magnetic resonance spectrum (CDCl$_3$) as shown in FIG. XII of the attached drawings;
(g) has a characteristic carbon-13 nuclear magnetic resonance spectrum (CDCl$_3$) as shown in FIG. XIII of the attached drawings; and
(h) has a characteristic electron impact mass spectrum as shown in FIG. XIV of the attached drawings.

22. The method according to claim 18, said method comprising: applying an effective amount of the agent designated LL-F28249δ, wherein the substantially pure form:
(a) has a molecular weight of 616 (EI-MS);
(b) has a molecular formula C$_{35}$H$_{52}$O$_9$;
(c) has an HPLC retention volume of 14.0 ml;
(d) has a characteristic ultraviolet absorption spectrum (methanol) as shown in FIG. XX of the attached drawings;
(e) has a characteristic proton nuclear magnetic resonance spectrum (CDCl$_3$) as shown in FIG. XXI of the attached drawings; and
(f) has a characteristic electron impact mass spectrum as shown in FIG. XXII of the attached drawings.

23. The method according to claim 18, said method comprising: applying an effective amount of the agent designated LL-F28249ε, wherein the substantially pure form:
(a) has a molecular weight of 598 (EI-MS);
(b) has a molecular formula C$_{35}$H$_{50}$O$_8$;
(c) has an HPLC retention volume of 14.8 ml;
(d) has a characteristic ultraviolet absorption spectrum (methanol) as shown in FIG. XXIII of the attached drawings;
(e) has a characteristic proton nuclear magnetic resonance spectrum (CDCl$_3$) as shown in FIG. XXIV of the attached drawings; and
(f) has a characteristic electron impact mass spectrum as shown in FIG. XXV of the attached drawings.

24. The method according to claim 18, said method comprising: applying an effective amount of the agent designated LL-F28249ζ, wherein the substantially pure form:
(a) has a molecular weight of 598 (EI-MS);
(b) has a molecular formula C$_{35}$H$_{50}$O$_8$;
(c) has an HPLC retention volume of 16.0 ml;
(d) has a characteristic ultraviolet absorption spectrum (methanol) as shown in FIG. XXVI of the attached drawings;
(e) has a characteristic proton nuclear magnetic resonance spectrum (CDCl$_3$) as shown in FIG. XXVII of the attached drawings; and
(f) has a characteristic electron impact mass spectrum as shown in FIG. XXVIII of the attached drawings.

25. The method according to claim 18, said method comprising: applying an effective amount of the agent designated LL-F28249η, wherein the substantially pure form:
(a) has a molecular weight of 612 (EI-MS);
(b) has a molecular formula C$_{36}$H$_{52}$O$_8$;
(c) has an HPLC retention volume of 23.5 ml;
(d) has a characteristic ultraviolet absorption spectrum (methanol) as shown in FIG. XXIX of the attached drawings;
(e) has a characteristic proton nuclear magnetic resonance spectrum (CDCl$_3$) as shown in FIG. XXX of the attached drawings; and
(f) has a characteristic electron impact mass spectrum as shown in FIG. XXXI of the attached drawings.

26. The method according to claim 18, said method comprising: applying an effective amount of the agent designated LL-F28249θ, wherein the substantially pure form:
(a) has a molecular weight of 626 (EI-MS);
(b) has a molecular formula C$_{37}$H$_{54}$O$_8$;
(c) has an HPLC retention volume of 24.5 ml;
(d) has a characteristic ultraviolet absorption spectrum (methanol) as shown in FIG. XXXII of the attached drawings;
(e) has a characteristic proton nuclear magnetic resonance spectrum (CDCl$_3$) as shown in FIG. XXXIII of the attached drawings; and
(f) has a characteristic electron impact mass spectrum as shown in FIG. XXXIV of the attached drawings.

27. The method according to claim 18, said method comprising: applying an effective amount of the agent designated LL-F28249ι, wherein the substantially pure form:
(a) has a molecular weight of 626 (EI-MS);
(b) has a molecular formula C$_{37}$H$_{54}$O$_8$;
(c) has an HPLC retention volume of 26.0 ml;
(d) has a characteristic ultraviolet absorption spectrum (methanol) as shown in FIG. XXXV of the attached drawings;
(e) has a characteristic proton nuclear magnetic resonance spectrum (CDCL$_3$) as shown in FIG. XXXVI of the attached drawings; and
(f) has a characteristic electron impact mass spectrum as shown in FIG. XXXVII of the attached drawings.

28. The method according to claim 18, said method comprising: applying an effective amount of the agent designated LL-F28249κ, wherein the substantially pure form:
(a) has a molecular weight of 584 (EI-MS);
(b) has a molecular formula C$_{35}$H$_{52}$O$_7$;
(c) has a specific optical rotation $[\alpha]_D^{26} = +189°$ (C, 0.165, acetone);

(d) has a characteristic ultraviolet absorption spectrum (methanol) as shown in FIG. XXXIX of the attached drawings;
(e) has a characteristic infrared absorption spectrum (KBr disc) as shown in FIG. XL of the attached drawings;
(f) has a characteristic electron impact mass spectrum as shown in FIG. XLI of the attached drawings;
(g) has a characteristic proton nuclear magnetic resonance spectrum ($CDCl_3$) as shown in FIG. XLII of the attached drawings; and
(h) has a characteristic carbon-13 nuclear magnetic resonance spectrum ($CDCl_3$) as shown in FIG. XLIII of the attached drawings.

29. The method according to claim 18, said method comprising: applying an effective amount of the agent designated LL-F28249λ, wherein the substantially pure form:
(a) has a molecular weight of 626 (FAB-MS);
(b) has a molecular formula $C_{37}H_{54}O_8$;
(c) has a specific optical rotation $[\alpha]_D^{26} = +145°$ (C, 0.23, acetone);
(d) has a characteristic ultraviolet absorption spectrum (methanol) as shown in FIG. XLIV of the attached drawings;
(e) has a characteristic infrared absorption spectrum (KBr disc) as shown in FIG. XLV of the attached drawings;
(f) has a characteristic electron impact mass spectrum as shown in FIG. XLVI of the attached drawings;
(g) has a characteristic proton nuclear magnetic resonance spectrum ($CDCl_3$) as shown in FIG. XLVII of the attached drawings; and
(h) has a characteristic carbon-13 nuclear magnetic resonance spectrum ($CDCl_3$) as shown in FIG. XLVIII of the attached drawings.

30. The method according to claim 18, said method comprising: applying an effective amount of the agent designated LL-F28249μ, wherein the substantially pure form:
(a) has a molecular weight of 612 (EI-MS);
(b) has a molecular formula $C_{37}H_{56}O_7$;
(c) has a characteristic ultraviolet absorption spectrum (methanol) as shown in FIG. XLIX of the attached drawings;
(d) has a characteristic infrared absorption spectrum (KBr disc) as shown in FIG. L of the attached drawings;
(e) has a characteristic electron impact mass spectrum as shown in FIG. LI of the attached drawings; and
(f) has a characteristic proton nuclear magnetic resonance spectrum ($CDCl_3$) as shown in FIG. LII of the attached drawings.

31. The method according to claim 18, said method comprising: applying an effective amount of the agent designated LL-F28249υ, wherein the substantially pure form:
(a) has a molecular weight of 592 (EI-MS);
(b) has a molecular formula $C_{36}H_{48}O_7$;
(c) has a specific optical rotation $[\alpha]_D^{26} = +131°$ (C, 0.325, acetone);
(d) has a characteristic ultraviolet absorption spectrum (methanol) as shown in FIG. LIII of the attached drawings;
(e) has a characteristic infrared absorption spectrum (KBr disc) as shown in FIG. LIV of the attached drawings;

(f) has a characteristic electron impact mass spectrum as shown in FIG. LV of the attached drawings;
(g) has a characteristic proton nuclear magnetic resonance spectrum ($CDCl_3$) as shown in FIG. LVI of the attached drawings; and
(h) has a characteristic carbon-13 nuclear magnetic resonance spectrum ($CDCl_3$) as shown in FIG. LVII of the attached drawings.

32. The method according to claim 18, said method comprising: applying an effective amount of the agent designated LL-F28249ω, wherein the substantially pure form:
(a) has a molecular weight of 806 (FAB-MS);
(b) has a molecular formula $C_{45}H_{74}O_{12}$;
(c) has a specific optical rotation $[\alpha]_D^{26} = -49 + 3°$ (C, 0.35, methanol);
(d) has a characteristic ultraviolet absorption spectrum (methanol) as shown in FIG. XV of the attached drawings;
(e) has a characteristic infrared absorption spectrum (KBr disc) as shown in FIG. XVI of the attached drawings;
(f) has a characteristic proton nuclear magnetic resonance spectrum ($CDCl_3$) as shown in FIG. XVII of the attached drawings;
(g) has a characteristic carbon-13 nuclear magnetic resonance spectrum ($CDCl_3$) as shown in FIG. XVIII of the attached drawings; and
(h) has a characteristic electron impact mass spectrum as shown in FIG. XIX of the attached drawings.

33. The method for the control of plant acarids or insects according to claims 18, 19, 20, 21, 22, 23, 24, 25, 26, 27, 28, 29, 30, 31 or 32, wherein about 0.01 kg per hectare to about 8 kg per hectare of active ingredient is applied to the breeding ground, food supply or habitat of the acarids or insects.

34. A method for protecting a plant from harmful effects of plant nematodes, insects or acarids, said method comprising: applying to the foliage of plants, the soil in which they are grown or into the trunks thereof, a nematocidally-, insecticidally- or acaricidally-effective amount of the fermentation broth or whole mash of microorganism *Streptomyces cyaneogriseus noncyanogenus*, having deposit accession number NRRL 15773, or a mutant thereof.

35. The method according to claim 34, wherein said fermentation broth or whole mash of microorganism *Streptomyces cyaneogriseus noncyanogenus* contains agents designated LL-F28249α, LL-F28249β, LL-F28249γ, LL-F28249δ, LL-F28249ε, LL-F28249ζ, LL-F28249η, LL-F28249θ, LL-F28249ι, LL-F28249κ, LL-F28249λ, LL-F28249μ, LL-F28249υ, and LL-F28249ω; or the pharmaceutically and pharmacologically-acceptable salts thereof, wherein said agents have characteristic spectra as shown in FIGS. I–LVII of the attached drawings.

36. The method according to claim 35, said method comprising: administering an effective amount of the agent designated LL-F28249α, wherein the substantially pure form:
(a) has a molecular weight of 612 (FAB-MS);
(b) has a molecular formula $C_{36}H_{52}O_8$;
(c) has a specific optical rotation $[\alpha]_D^{26} = +133 \pm 3°$ (C, 0.3, acetone);
(d) has a characteristic ultraviolet absorption spectrum as shown in FIG. I of the attached drawings;

(e) has a characteristic infrared absorption spectrum (KBr disc) as shown in FIG. II of the attached drawings;
(f) has a characteristic proton nuclear magnetic resonance spectrum (CDCl$_3$) as shown in FIG. III of the attached drawings;
(g) has a characteristic carbon-13 nuclear magnetic resonance spectrum (CDCl$_3$) as shown in FIG. IV of the attached drawings; and
(h) has a characteristic electron impact mass spectrum as shown in FIG. V of the attached drawings.

37. The method according to claim 35, said method comprising: administering an effective amount of the agent designated LL-F28249β, wherein the substantially pure form:
(a) has a molecular weight of 584 (FAB-MS);
(b) has a molecular formula C$_{34}$H$_{48}$O$_8$;
(c) has a specific optical rotation $[\alpha]_D^{26} = +125°$ (C, 0.3, acetone);
(d) has a characteristic ultraviolet absorption spectrum as shown in FIG. VI of the attached drawings;
(e) has a characteristic infrared absorption spectrum (KBr disc) as shown in FIG. VII of the attached drawings;
(f) has a characteristic proton nuclear magnetic resonance spectrum (CDCl$_3$) as shown in FIG. VIII of the attached drawings;
(g) has a characteristic carbon-13 nuclear magnetic resonance spectrum (CDCl$_3$) as shown in FIG. XXXVIII of the attached drawings; and
(h) has a characteristic electron impact mass spectrum as shown in FIG. IX of the attached drawings.

38. The method according to claim 35, said method comprising: administering an effective amount of the agent designated LL-F28249γ, wherein the substantially pure form:
(a) has a molecular weight of 598 (FAB-MS);
(b) has a molecular formula C$_{35}$H$_{50}$O$_8$;
(c) has a specific optical rotation $[\alpha]_D^{26} = +150+4°$ (C, 0.3, acetone);
(d) has a characteristic ultraviolet absorption spectrum as shown in FIG. X of the attached drawings;
(e) has a characteristic infrared absorption spectrum (KBr disc) as shown in FIG. XI of the attached drawings;
(f) has a characteristic proton nuclear magnetic resonance spectrum (CDCl$_3$) as shown in FIG. XII of the attached drawings;
(g) has a characteristic carbon-13 nuclear magnetic resonance spectrum (CDCl$_3$) as shown in FIG. XIII of the attached drawings; and
(h) has a characteristic electron impact mass spectrum as shown in FIG. XIV of the attached drawings.

39. The method according to claim 35, said method comprising: administering an effective amount of the agent designated LL-F28249δ, wherein the substantially pure form:
(a) has a molecular weight of 616 (EI-MS);
(b) has a molecular formula C$_{35}$H$_{52}$O$_9$;
(c) has an HPLC retention volume of 14.0 ml;
(d) has a characteristic ultraviolet absorption spectrum (methanol) as shown in FIG. XX of the attached drawings;
(e) has a characteristic proton nuclear magnetic resonance spectrum (CDCl$_3$) as shown in FIG. XXI of the attached drawings; and
(f) has a characteristic electron impact mass spectrum as shown in FIG. XXII of the attached drawings.

40. The method according to claim 35, said method comprising: administering an effective amount of the agent designated LL-F28249ε, wherein the substantially pure form:
(a) has a molecular weight of 598 (EI-MS);
(b) has a molecular formula C$_{35}$H$_{50}$O$_8$;
(c) has an HPLC retention volume of 14.8 ml;
(d) has a characteristic ultraviolet absorption spectrum (methanol) as shown in FIG. XXIII of the attached drawings;
(e) has a characteristic proton nuclear magnetic resonance spectrum (CDCl$_3$) as shown in FIG. XXIV of the attached drawings;and
(f) has a characteristic electron impact mass spectrum as shown in FIG. XXV of the attached drawings.

41. The method according to claim 35, said method comprising: administering an effective amount of the agent designated LL-F28249ζ, wherein the substantially pure form:
(a) has a molecular weight of 598 (EI-MS);
(b) has a molecular formula C$_{35}$H$_{50}$O$_8$;
(c) has an HPLC retention volume of 16.0 ml;
(d) has a characteristic ultraviolet absorption spectrum (methanol) as shown in FIG. XXVI of the attached drawings;
(e) has a characteristic proton nuclear magnetic resonance spectrum (CDCl$_3$) as shown in FIG. XXVII of the attached drawings; and
(f) has a characteristic electron impact mass spectrum as shown in FIG. XXVIII of the attached drawings.

42. The method according to claim 35, said method comprising: administering an effective amount of the agent designated LL-F28249η, wherein the substantially pure form:
(a) has a molecular weight of 612 (EI-MS);
(b) has a molecular formula C$_{36}$H$_{52}$O$_8$;
(c) has an HPLC retention volume of 23.5 ml;
(d) has a characteristic ultraviolet absorption spectrum (methanol) as shown in FIG. XXIX of the attached drawings;
(e) has a characteristic proton nuclear magnetic resonance spectrum (CDCl$_3$) as shown in FIG. XXX of the attached drawings; and
(f) has a characteristic electron impact mass spectrum as shown in FIG. XXXI of the attached drawings.

43. The method according to claim 35, said method comprising: administering an effective amount of the agent designated LL-F28249θ, wherein the substantially pure form:
(a) has a molecular weight of 626 (EI-MS);
(b) has a molecular formula C$_{37}$H$_{54}$O$_8$;
(c) has an HPLC retention volume of 24.5 ml;
(d) has a characteristic ultraviolet absorption spectrum (methanol) as shown in FIG. XXXII of the attached drawings;
(e) has a characteristic proton nuclear magnetic resonance spectrum (CDCl$_3$) as shown in FIG. XXXIII of the attached drawings; and
(f) has a characteristic electron impact mass spectrum as shown in FIG. XXXIV of the attached drawings.

44. The method according to claim 35, said method comprising: administering an effective amount of the agent designated LL-F28249ι, wherein the substantially pure form:
(a) has a molecular weight of 626 (EI-MS);
(b) has a molecular formula $C_{37}H_{54}O_8$;
(c) has an HPLC retention volume of 26.0 ml;
(d) has a characteristic ultraviolet absorption spectrum (methanol) as shown in FIG. XXXV of the attached drawings;
(e) has a characteristic proton nuclear magnetic resonance spectrum ($CDCl_3$) as shown in FIG. XXXVI of the attached drawings; and
(f) has a characteristic electron impact mass spectrum as shown in FIG. XXXVII of the attached drawings.

45. The method according to claim 35, said method comprising: administering an effective amount of the agent designated LL-F28249κ, wherein the substantially pure form:
(a) has a molecular weight of 584 (EI-MS);
(b) has a molecular formula $C_{35}H_{52}O_7$;
(c) has a specific optical rotation $[\alpha]_D^{26} = +189°$ (C, 0.165, acetone);
(d) has a characteristic ultraviolet absorption spectrum (methanol) as shown in FIG. XXXIX of the attached drawings;
(e) has a characteristic infrared absorption spectrum (KBr disc) as shown in FIG. XL of the attached drawings;
(f) has a characteristic electron impact mass spectrum as shown in FIG. XLI of the attached drawings;
(g) has a characteristic proton nuclear magnetic resonance spectrum ($CDCl_3$) as shown in FIG. XLII of the attached drawings; and
(h) has a characteristic carbon-13 nuclear magnetic resonance spectrum ($CDCl_3$) as shown in FIG. XLIII of the attached drawings.

46. The method according to claim 35, said method comprising: administering an effective amount of the agent designated LL-F28249λ, wherein the substantially pure form:
(a) has a molecular weight of 626 (FAB-MS);
(b) has a molecular formula $C_{37}H_{54}O_8$;
(c) has a specific optical rotation $[\alpha]_D^{26} = +145°$ (C, 0.23, acetone);
(d) has a characteristic ultraviolet absorption spectrum (methanol) as shown in FIG. XLIV of the attached drawings;
(e) has a characteristic infrared absorption spectrum (KBr disc) as shown in FIG. XLV of the attached drawings;
(f) has a characteristic electron impact mass spectrum as shown in FIG. XLVI of the attached drawings;
(g) has a characteristic proton nuclear magnetic resonance spectrum ($CDCl_3$) as shown in FIG. XLVII of the attached drawings; and
(h) has a characteristic carbon-13 nuclear magnetic resonance spectrum ($CDCl_3$) as shown in FIG. XLVIII of the attached drawings.

47. The method according to claim 35, said method comprising: administering an effective amount of the agent designated LL-F28249μ, wherein the substantially pure form:
(a) has a molecular weight of 612 (EI-MS);
(b) has a molecular formula $C_{37}H_{56}O_7$;
(c) has a characteristic ultraviolet absorption spectrum (methanol) as shown in FIG. XLIX of the attached drawings;
(d) has a characteristic infrared absorption spectrum (KBr disc) as shown in FIG. L of the attached drawings;
(e) has a characteristic electron impact mass spectrum as shown in FIG. LI of the attached drawings; and
(f) has a characteristic proton nuclear magnetic resonance spectrum ($CDCl_3$) as shown in FIG. LII of the attached drawings.

48. The method according to claim 35, said method comprising: administering an effective amount of the agent designated LL-F28249ν, wherein the substantially pure form:
(a) has a molecular weight of 592 (EI-MS);
(b) has a molecular formula $C_{36}H_{48}O_7$;
(c) has a specific optical rotation $[\alpha]_D^{26} = +131°$ (C, 0.325, acetone);
(d) has a characteristic ultraviolet absorption spectrum (methanol) as shown in FIG. LIII of the attached drawings;
(e) has a characteristic infrared absorption spectrum (KBr disc) as shown in FIG. LIV of the attached drawings;
(f) has a characteristic electron impact mass spectrum as shown in FIG. LV of the attached drawings;
(g) has a characteristic proton nuclear magnetic resonance spectrum ($CDCl_3$) as shown in FIG. LVI of the attached drawings; and
(h) has a Characteristic carbon-13 nuclear magnetic resonance spectrum ($CDCl_3$) as shown in FIG. LVII of the attached drawings.

49. The method according to claim 35, said method comprising: administering an effective amount of the agent designated LL-F28249ω, wherein the substantially pure form:
(a) has a molecular weight of 806 (FAB-MS);
(b) has a molecular formula $C_{45}H_{74}O_{12}$;
(c) has a specific optical rotation $[\alpha]_D^{26} = -49+3°$ (C, 0.35, methanol);
(d) has a characteristic ultraviolet absorption spectrum (methanol) as shown in FIG. XV of the attached drawings;
(e) has a characteristic infrared absorption spectrum (KBr disc) as shown in FIG. XVI of the attached drawings;
(f) has a characteristic proton nuclear magnetic resonance spectrum ($CDCl_3$) as shown in FIG. XVII of the attached drawings;
(g) has a characteristic carbon-13 nuclear magnetic resonance spectrum ($CDCl_3$) as shown in FIG. XVIII of the attached drawings; and
(h) has a characteristic electron impact mass spectrum as shown in FIG. XIX of the attached drawings.

* * * * *